US012655199B2

(12) United States Patent
Xu et al.

(10) Patent No.: US 12,655,199 B2
(45) Date of Patent: Jun. 16, 2026

(54) TUMOR THERAPEUTIC AGENT AND USE THEREOF

(71) Applicant: Keymed Biosciences Co., Ltd., Chengdu (CN)

(72) Inventors: Gang Xu, Chengdu (CN); Bo Chen, Chengdu (CN); Ying Wang, Chengdu (CN)

(73) Assignee: Keymed Biosciences Co., Ltd., Chengdu (CN)

( * ) Notice: Subject to any disclaimer, the term of this patent is extended or adjusted under 35 U.S.C. 154(b) by 1247 days.

(21) Appl. No.: 17/604,735

(22) PCT Filed: Apr. 15, 2020

(86) PCT No.: PCT/CN2020/084991
§ 371 (c)(1),
(2) Date: Oct. 18, 2021

(87) PCT Pub. No.: WO2020/211792
PCT Pub. Date: Oct. 22, 2020

(65) Prior Publication Data
US 2022/0372112 A1 Nov. 24, 2022

(30) Foreign Application Priority Data
Apr. 19, 2019 (CN) .......................... 201910315634.9

(51) Int. Cl.
*C07K 16/00* (2006.01)
*A61P 35/00* (2006.01)
*C07K 16/28* (2006.01)

(52) U.S. Cl.
CPC ............ *C07K 16/005* (2013.01); *A61P 35/00* (2018.01); *C07K 16/28* (2013.01); *C07K 2317/24* (2013.01); *C07K 2317/55* (2013.01); *C07K 2317/732* (2013.01)

(58) Field of Classification Search
CPC ................ A61P 35/00; C07K 2317/24; C07K 2317/732
See application file for complete search history.

(56) References Cited

U.S. PATENT DOCUMENTS

2019/0233511 A1 8/2019 Wang et al.

FOREIGN PATENT DOCUMENTS

| | | |
|---|---|---|
| AU | 2017294276 A1 | 2/2019 |
| CN | 105073776 | 11/2015 |
| WO | 2013167153 A1 | 11/2013 |
| WO | WO 2013/167259 | 11/2013 |
| WO | 2014075788 A1 | 5/2014 |
| WO | 2014127785 A1 | 8/2014 |

OTHER PUBLICATIONS

Zhou et. al. (Targeting Claudin-18.2 for cancer therapy: updates from 2024 ASCO annual meeting. Journal of Hematology and Oncology. vol. 17, article No. 73) (Year: 2024).*
Brummel et al., "Probing the combining site of an anti-carbohydrate antibody by saturation-mutagenesis: role of the heavy-chain CDR3 residues," Biochemistry. (1993) 32(4): 1180-1187.
Burks et al., "In vitro scanning saturation mutagenesis of an antibody binding pocket," Proc Natl Acad Sci U S A. (1997) 94(2): 412-417.
Carrillo et al., "The Multiple Sequence Alignment Problem in Biology," Siam J Appl Math. 48(5); 1073-1082.
Englebienne, "Use of colloidal gold surface plasmon resonance peak shift to infer affinity constants from the interactions between protein antigens and antibodies specific for single or multiple epitopes," Analyst. (1998) 123; 1599-1603.
International Search Report and Written Opinion mailed Jul. 28, 2020, directed to International Application No. PCT/CN2020/084991; 23 pages.
Kobayashi et al., "Tryptophan H33 plays an important role in pyrimidine (6-4) pyrimidone photoproduct binding by a high-affinity antibody," Protein Engineering (1999) 12(10); 879-884.
Marasco et al., "Design, intracellular expression, and activity of a human anti-human immunodeficiency virus type 1 gp120 single-chain antibody," Proc Natl Acad Sci U S A. (1993) 90(16): 7889-7893.
Nelson et al., "Demystified . . . Monoclonal antibodies," Mol Pathol. (2000) 53(3): 111-117.
Rich et al., "Advances in surface plasmon resonance biosensor analysis," Curr Opin Biotechnol. (2000) 11(1): 54-61.
Smith et al., "Demystified . . . recombinant antibodies," J Clin Pathol. (2004) 57(9): 912-917.
Singh et al., "Anti-claudin 18.2 antibody as new targeted therapy for advanced gastric cancer," Journal of Hematology & Oncology (2017) 10:105.
European Search Report, dated Nov. 7, 2022, for European Patent Application No. 20791781.6. (7 pages).
Lin et al., "Anti-Human Claudin-18.2 Monoclonal Antibody As Cancer Therapeutics," Poster, retrieved at URL=https://accurusbio.com/web/image/Anti-CLDN18.2%20Poster%20AACR%20TII.111918%20pdf.pdf, Mar. 20, 2019. (1 page).
Türeci et al., "Characterization of zolbetuximab in pancreatic cancer models," Oncoimmunology 8(1):e1523096, 2019 [Published online Nov. 10, 2018]. (10 pages).

* cited by examiner

*Primary Examiner* — Misook Yu
(74) *Attorney, Agent, or Firm* — McDonnell Boehnen Hulbert & Berghoff LLP

(57) ABSTRACT

Provided is an antibody that recognizes a tight junction protein 18.2, a preparation method therefor, and a use thereof.

20 Claims, 7 Drawing Sheets
Specification includes a Sequence Listing.

SEQUENCE LISTING

<160> NUMBER OF SEQ ID NOS: 276

<210> SEQ ID NO 1
<211> LENGTH: 118
<212> TYPE: PRT
<213> ORGANISM: Homo sapiens

<400> SEQUENCE: 1

```
Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Thr Phe
            20                  25                  30

Gly Ile Asn Trp Val Arg Gln Arg Pro Glu Gln Gly Leu Glu Trp Ile
        35                  40                  45

Gly Trp Ile Phe Pro Gly Asp Gly Ser Ile Lys Tyr Asn Glu Lys Phe
    50                  55                  60
```

```
Lys Gly Lys Ala Thr Leu Thr Thr Asp Lys Ser Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg Phe Tyr Tyr Gly Asn Ser Phe Val Ser Trp Gly Gln Gly Thr
            100                 105                 110

Leu Val Thr Val Ser Ala
        115

<210> SEQ ID NO 2
<211> LENGTH: 10
<212> TYPE: PRT
<213> ORGANISM: Homo sapiens

<400> SEQUENCE: 2

Gly Tyr Thr Phe Thr Thr Phe Gly Ile Asn
1               5                   10

<210> SEQ ID NO 3
<211> LENGTH: 17
<212> TYPE: PRT
<213> ORGANISM: Homo sapiens

<400> SEQUENCE: 3

Trp Ile Phe Pro Gly Asp Gly Ser Ile Lys Tyr Asn Glu Lys Phe Lys
1               5                   10                  15

Gly

<210> SEQ ID NO 4
<211> LENGTH: 9
<212> TYPE: PRT
<213> ORGANISM: Homo sapiens

<400> SEQUENCE: 4

Phe Tyr Tyr Gly Asn Ser Phe Val Ser
1               5

<210> SEQ ID NO 5
<211> LENGTH: 354
<212> TYPE: DNA
<213> ORGANISM: Homo sapiens

<400> SEQUENCE: 5
caggttcagc tgcagcagtc tggagctgaa ctggtaaagc ctggggcttc agtgaagttg      60
tcctgcaagg cttctggcta cacattcaca acttttggta taaactgggt gaggcagagg     120
cctgaacagg gacttgaatg gattggatgg atttttcctg gagatggtag tattaagtac     180
aatgagaagt tcaagggcaa ggccacactg actacagaca atcctccag tacagcctac      240 atgcagatca gcagtttgac atctgaggac tcggctgtct atttctgtgc aaggttctac     300
tatggtaact cctttgtttc ctggggccaa gggactctgg tcactgtctc tgca           354

<210> SEQ ID NO 6
<211> LENGTH: 113
<212> TYPE: PRT
<213> ORGANISM: Homo sapiens

<400> SEQUENCE: 6

Asp Ile Val Met Thr Gln Ser Pro Ser Ser Leu Ala Val Thr Ala Gly
1               5                   10                  15
```

-continued

```
Glu Lys Val Thr Met Thr Cys Lys Ser Ser Gln Ser Leu Leu Asn Ser
             20                  25                  30

Gly Asn Gln Lys Asn Tyr Leu Thr Trp Tyr Gln Arg Pro Gly Gln
         35                  40                  45

Pro Pro Lys Leu Leu Leu Tyr Trp Ala Ser Thr Arg Glu Ser Gly Val
     50                  55                  60

Pro Asp Arg Phe Thr Gly Ser Gly Ser Gly Thr Asp Phe Ala Leu Thr
65                  70                  75                  80

Ile Thr Ser Val Gln Ala Glu Asp Leu Ala Val Tyr Tyr Cys Gln Asn
                 85                  90                  95

Asp Tyr Thr Tyr Pro Phe Thr Phe Gly Ser Gly Thr Lys Leu Glu Ile
             100                 105                 110

Lys
```

```
<210> SEQ ID NO 7
<211> LENGTH: 17
<212> TYPE: PRT
<213> ORGANISM: Homo sapiens

<400> SEQUENCE: 7

Lys Ser Ser Gln Ser Leu Leu Asn Ser Gly Asn Gln Lys Asn Tyr Leu
1               5                   10                  15

Thr
```

```
<210> SEQ ID NO 8
<211> LENGTH: 7
<212> TYPE: PRT
<213> ORGANISM: Homo sapiens

<400> SEQUENCE: 8

Trp Ala Ser Thr Arg Glu Ser
1               5
```

```
<210> SEQ ID NO 9
<211> LENGTH: 9
<212> TYPE: PRT
<213> ORGANISM: Homo sapiens

<400> SEQUENCE: 9

Gln Asn Asp Tyr Thr Tyr Pro Phe Thr
1               5
```

```
<210> SEQ ID NO 10
<211> LENGTH: 339
<212> TYPE: DNA
<213> ORGANISM: Homo sapiens

<400> SEQUENCE: 10
gacattgtga tgacacagtc tccatcctcc ctggctgtga ctgcaggaga gaaggtcact      60
atgacctgca agtccagtca gagtctgtta aacagtggaa atcaaaagaa ctacttgacc     120
tggtaccaac agagaccagg gcagcctcct aaacttttgc tctactgggc atccactagg     180
gaatctgggg tccctgatcg cttcacaggc agtggatctg gaacagattt cgctctcacc     240
atcaccagtg tgcaggctga agacctggca gtttattact gtcagaatga ttatacttat     300
ccattcacgt tcggctcggg gacaaagttg gaaataaaa                            339
```

```
<210> SEQ ID NO 11
<211> LENGTH: 118
<212> TYPE: PRT
```

<213> ORGANISM: Homo sapiens

<400> SEQUENCE: 11

Gln Val Gln Leu Gln Gln Ser Gly Arg Glu Val Val Arg Pro Gly Thr
1               5                   10                  15

Ser Val Lys Val Ser Cys Lys Pro Ser Gly Tyr Ala Phe Thr Asn Tyr
            20                  25                  30

Leu Ile Asp Trp Val Lys Gln Arg Pro Gly Gln Gly Leu Glu Trp Ile
            35                  40                  45

Gly Gly Ile Asn Pro Gly Ser Gly Asp Thr Val Tyr Asn Glu Lys Phe
        50                  55                  60

Lys Ala Lys Ala Thr Leu Thr Ala Asp Lys Ser Ser Met Thr Ala Asn
65                  70                  75                  80

Met Gln Leu Ser Ser Leu Thr Ser Asp Asp Ser Ala Val Tyr Phe Cys
                85                  90                  95

Ala Arg Arg Val Arg Gly Asn Ser Phe Asp Ser Trp Gly Gln Gly Thr
                100                 105                 110

Leu Val Thr Val Ser Ala
        115

<210> SEQ ID NO 12
<211> LENGTH: 10
<212> TYPE: PRT
<213> ORGANISM: Homo sapiens

<400> SEQUENCE: 12

Gly Tyr Ala Phe Thr Asn Tyr Leu Ile Asp
1               5                   10

<210> SEQ ID NO 13
<211> LENGTH: 17
<212> TYPE: PRT
<213> ORGANISM: Homo sapiens

<400> SEQUENCE: 13

Gly Ile Asn Pro Gly Ser Gly Asp Thr Val Tyr Asn Glu Lys Phe Lys
1               5                   10                  15

Ala

<210> SEQ ID NO 14
<211> LENGTH: 9
<212> TYPE: PRT
<213> ORGANISM: Homo sapiens

<400> SEQUENCE: 14

Arg Val Arg Gly Asn Ser Phe Asp Ser
1               5

<210> SEQ ID NO 15
<211> LENGTH: 354
<212> TYPE: DNA
<213> ORGANISM: Homo sapiens

<400> SEQUENCE: 15
caggtccagc tgcagcagtc tggacgtgag gtggtaaggc ctgggacttc agtgaaggtg      60
tcctgcaagc cttctggata cgccttcact aattacttga tagactgggt aaaacagagg     120
cctggacagg gccttgagtg gattggaggg attaatcctg gaagtggtga cactgtgtac     180
aatgagaagt tcaaggccaa ggcaacactg actgcagaca atcctccat gactgccaac      240

-continued atgcagctca gcagcctgac atctgatgac tctgcggtct atttctgcgc aagaagggtc        300
cgtggtaatt cgtttgattc ctggggccaa gggactctgg tcactgtctc tgca        354

<210> SEQ ID NO 16
<211> LENGTH: 113
<212> TYPE: PRT
<213> ORGANISM: Homo sapiens

<400> SEQUENCE: 16

Asp Ile Gln Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Arg Asn Tyr Leu Thr Trp Tyr Gln Gln Lys Thr Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Asn
                85                  90                  95

Asn Tyr Tyr Tyr Pro Leu Thr Phe Gly Ala Gly Thr Lys Leu Glu Ile
            100                 105                 110

Lys

<210> SEQ ID NO 17
<211> LENGTH: 17
<212> TYPE: PRT
<213> ORGANISM: Homo sapiens

<400> SEQUENCE: 17

Lys Ser Ser Gln Ser Leu Leu Asn Ser Gly Asn Gln Arg Asn Tyr Leu
1               5                   10                  15

Thr

<210> SEQ ID NO 18
<211> LENGTH: 7
<212> TYPE: PRT
<213> ORGANISM: Homo sapiens

<400> SEQUENCE: 18

Trp Ala Ser Thr Arg Glu Ser
1               5

<210> SEQ ID NO 19
<211> LENGTH: 9
<212> TYPE: PRT
<213> ORGANISM: Homo sapiens

<400> SEQUENCE: 19

Gln Asn Asn Tyr Tyr Tyr Pro Leu Thr
1               5

<210> SEQ ID NO 20
<211> LENGTH: 339
<212> TYPE: DNA
<213> ORGANISM: Homo sapiens

<400> SEQUENCE: 20
gacattcaga tgacccagtc tccatcctcc ctgactgtga cagcaggaga gaaggtcact        60

```
atgagctgca agtccagtca gagtctgtta aacagtggaa atcaaaggaa ctacttgacc      120
tggtaccagc agaaacagg gcagcctcct aaactgttga tctactgggc atccactagg      180
gaatctgggg tccctgatcg cttcacaggc agtggatctg gaactgattt cactctcacc      240
atcaacagtg tgcaggctga agacctggca gtttattact gtcagaataa ttattattat      300
ccgctcacgt tcggtgctgg gaccaagctg gaaataaaa                            339
```

```
<210> SEQ ID NO 21
<211> LENGTH: 117
<212> TYPE: PRT
<213> ORGANISM: Homo sapiens

<400> SEQUENCE: 21

Glu Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Gly Val Ser Trp Ile Arg Gln Pro Pro Gly Lys Gly Leu Glu Trp Leu
        35                  40                  45

Gly Ala Ile Trp Ala Gly Gly Asn Thr Asn Tyr Asn Ser Ala Leu Met
    50                  55                  60

Ser Arg Leu Ser Ile Arg Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Val Gly Tyr Gly Asn Ser Phe Ala Asn Trp Gly Gln Gly Thr Leu
            100                 105                 110

Val Thr Val Ser Ala
        115
```

```
<210> SEQ ID NO 22
<211> LENGTH: 10
<212> TYPE: PRT
<213> ORGANISM: Homo sapiens

<400> SEQUENCE: 22

Gly Phe Ser Leu Thr Asn Tyr Gly Val Ser
1               5                   10
```

```
<210> SEQ ID NO 23
<211> LENGTH: 16
<212> TYPE: PRT
<213> ORGANISM: Homo sapiens

<400> SEQUENCE: 23

Ala Ile Trp Ala Gly Gly Asn Thr Asn Tyr Asn Ser Ala Leu Met Ser
1               5                   10                  15
```

```
<210> SEQ ID NO 24
<211> LENGTH: 9
<212> TYPE: PRT
<213> ORGANISM: Homo sapiens

<400> SEQUENCE: 24

Val Gly Tyr Gly Asn Ser Phe Ala Asn
1               5
```

```
<210> SEQ ID NO 25
<211> LENGTH: 352
```

```
<212> TYPE: DNA
<213> ORGANISM: Homo sapiens

<400> SEQUENCE: 25
gaggtccagc tgaaggagtc aggacctggc ctggtggcgc cctcacagag cctgtccatc      60
acttgcactg tctctgggtt ttcattgacc aactatggtg tttcctggat tcgccagcct     120
ccaggaaagg gtctggagtg gctgggagca atatgggctg gtggaaacac aaattataat     180
tcggctctca tgtccagact gagcatcagg aaagacaatt ccaagagcca agttttctta     240
aaaatgaaca gtctccaaac tgatgacaca gccatgtact actgtgccag agtagggtat     300
ggtaactcgt ttgctaactg gggccaaggg actctggtca ctgtctctgc ag            352

<210> SEQ ID NO 26
<211> LENGTH: 113
<212> TYPE: PRT
<213> ORGANISM: Homo sapiens

<400> SEQUENCE: 26

Asp Ile Val Met Thr Gln Ser Pro Ser Ser Leu Thr Val Thr Ala Gly
1               5                   10                  15

Glu Lys Val Thr Leu Ser Cys Lys Ser Ser Gln Thr Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asn Tyr Phe Tyr Pro Leu Thr Phe Gly Ala Gly Thr Arg Leu Glu Ile
            100                 105                 110

Lys

<210> SEQ ID NO 27
<211> LENGTH: 17
<212> TYPE: PRT
<213> ORGANISM: Homo sapiens

<400> SEQUENCE: 27

Lys Ser Ser Gln Thr Leu Leu Asn Ser Gly Asn Gln Lys Asn Tyr Leu
1               5                   10                  15

Thr

<210> SEQ ID NO 28
<211> LENGTH: 7
<212> TYPE: PRT
<213> ORGANISM: Homo sapiens

<400> SEQUENCE: 28

Trp Ala Ser Thr Arg Glu Ser
1               5

<210> SEQ ID NO 29
<211> LENGTH: 9
<212> TYPE: PRT
<213> ORGANISM: Homo sapiens

<400> SEQUENCE: 29
```

```
Gln Asn Asn Tyr Phe Tyr Pro Leu Thr
1               5
```

```
<210> SEQ ID NO 30
<211> LENGTH: 339
<212> TYPE: DNA
<213> ORGANISM: Homo sapiens

<400> SEQUENCE: 30
gacattgtga tgacacagtc tccatcctcc ctgactgtga cagcaggaga gaaggtcact       60
ctgagctgca agtccagtca gactctgtta aacagtggaa atcaaaagaa ctacttgacg      120
tggtaccagc agaaaccagg gcagcctcct aaactgttga tctactgggc atccactagg      180
gaatctgggg tccctgatcg cttcacaggc agtggatctg gaacagattt cactctcacc      240
atcagcagcg tgcaggctga agacctggca gtttattact gtcagaataa ttattttat       300 ccgctcacgt tcggtgctgg gaccagactg gaaataaaa                            339
```

```
<210> SEQ ID NO 31
<211> LENGTH: 118
<212> TYPE: PRT
<213> ORGANISM: Homo sapiens

<400> SEQUENCE: 31

Glu Val Gln Leu Gln Gln Ser Gly Arg Glu Val Val Arg Pro Gly Thr
1               5                   10                  15

Ser Val Lys Val Ser Cys Lys Pro Ser Gly Tyr Ala Phe Thr Asn Tyr
                20                  25                  30

Leu Ile Asp Trp Val Lys Gln Arg Pro Gly Gln Gly Leu Glu Trp Ile
            35                  40                  45

Gly Gly Ile Asn Pro Gly Ser Gly Asp Thr Val Tyr Asn Glu Arg Phe
        50                  55                  60

Lys Asp Lys Ala Thr Leu Thr Ala Asp Lys Ser Ser Ser Ser Ala Asn
65                  70                  75                  80

Met Gln Leu Ser Ser Leu Thr Ser Asp Asp Ser Ala Val Tyr Phe Cys
                85                  90                  95

Ala Arg Arg Val Arg Gly Asn Ser Phe Asp Ser Trp Gly Gln Gly Thr
                100                 105                 110

Leu Val Thr Val Ser Ala
        115
```

```
<210> SEQ ID NO 32
<211> LENGTH: 10
<212> TYPE: PRT
<213> ORGANISM: Homo sapiens

<400> SEQUENCE: 32

Gly Tyr Ala Phe Thr Asn Tyr Leu Ile Asp
1               5                   10
```

```
<210> SEQ ID NO 33
<211> LENGTH: 17
<212> TYPE: PRT
<213> ORGANISM: Homo sapiens

<400> SEQUENCE: 33

Gly Ile Asn Pro Gly Ser Gly Asp Thr Val Tyr Asn Glu Arg Phe Lys
1               5                   10                  15

Asp
```

-continued

<210> SEQ ID NO 34
<211> LENGTH: 9
<212> TYPE: PRT
<213> ORGANISM: Homo sapiens

<400> SEQUENCE: 34

Arg Val Arg Gly Asn Ser Phe Asp Ser
1               5

<210> SEQ ID NO 35
<211> LENGTH: 354
<212> TYPE: DNA
<213> ORGANISM: Homo sapiens

<400> SEQUENCE: 35
gaggtccagc tgcagcagtc tggacgtgag gtggtaaggc ctgggacttc agtgaaggtg      60
tcctgcaagc cttctggata cgccttcact aattacttga tagactgggt taaacagagg     120
cctggacagg gccttgagtg gattggaggg attaatcctg aagtggtga cactgtgtac     180 aatgagaggt tcaaggacaa ggcaacactg actgcagaca atcctccag ctctgccaac     240 atgcagctca gcagcctgac atctgatgac tctgcggtct atttctgcgc aagaagggtc     300
cgtggtaatt cgtttgattc ctggggccaa gggactctgg tcactgtctc tgca          354

<210> SEQ ID NO 36
<211> LENGTH: 113
<212> TYPE: PRT
<213> ORGANISM: Homo sapiens

<400> SEQUENCE: 36

Asp Ile Val Met Thr Gln Ser Pro Ser Ser Leu Thr Val Thr Ala Gly
1               5                  10                  15

Gln Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Lys Asp Phe Thr Leu Thr
65                  70                  75                  80

Ile Ser Ser Val Gln Ala Glu Asp Leu Ala Val Phe Tyr Cys Gln Asn
                85                  90                  95

Asn Tyr Phe Tyr Pro Leu Thr Phe Gly Ala Gly Thr Lys Leu Glu Leu
            100                 105                 110

Lys

<210> SEQ ID NO 37
<211> LENGTH: 17
<212> TYPE: PRT
<213> ORGANISM: Homo sapiens

<400> SEQUENCE: 37

Lys Ser Ser Gln Ser Leu Leu Asn Ser Gly Asn Gln Lys Asn Tyr Leu
1               5                  10                  15

Thr

<210> SEQ ID NO 38
<211> LENGTH: 7

```
<212> TYPE: PRT
<213> ORGANISM: Homo sapiens

<400> SEQUENCE: 38

Trp Ala Ser Thr Arg Glu Ser
1               5

<210> SEQ ID NO 39
<211> LENGTH: 9
<212> TYPE: PRT
<213> ORGANISM: Homo sapiens

<400> SEQUENCE: 39

Gln Asn Asn Tyr Phe Tyr Pro Leu Thr
1               5

<210> SEQ ID NO 40
<211> LENGTH: 339
<212> TYPE: DNA
<213> ORGANISM: Homo sapiens

<400> SEQUENCE: 40
gacattgtga tgactcagtc tccatcctcc ctaactgtga cagcaggaca gaaggtcact        60
atgagctgca agtccagtca gagtctgtta aacagtggaa atcaaaagaa ctacttgacc       120
tggtaccagc agaaaccggg gcagcctcct aaactgttga tctactgggc atccactagg       180
gaatctgggg tccctgatcg cttcacaggc agtgggtctg gaaaagattt cactctcacc       240
atcagcagtg tgcaggctga agacctggca gttttttact gtcagaataa ttattttttat      300 ccgctcacgt tcggtgctgg gaccaagctg gagctgaaa                              339

<210> SEQ ID NO 41
<211> LENGTH: 118
<212> TYPE: PRT
<213> ORGANISM: Homo sapiens

<400> SEQUENCE: 41

Glu Val Lys Leu Val Glu Ser Gly Gly Gly Leu Val Arg Pro Gly Gly
1               5                   10                  15

Ser Leu Lys Val Ser Cys Ala Ala Ser Gly Ile Thr Phe Ser Arg Tyr
                20                  25                  30

Ala Ile Ser Trp Val Arg Gln Thr Pro Glu Lys Arg Leu Glu Trp Val
            35                  40                  45

Ala Thr Ile Ser Ser Gly Asp Ser Tyr Thr Tyr Tyr Leu Asp Ser Val
        50                  55                  60

Lys Gly Arg Phe Thr Ile Ser Arg Asp Asp Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Gly Arg Leu Gly Tyr Gly Asn Ala Met Asp Tyr Trp Gly Gln Gly Thr
            100                 105                 110

Ser Val Thr Val Ser Ser
        115

<210> SEQ ID NO 42
<211> LENGTH: 10
<212> TYPE: PRT
<213> ORGANISM: Homo sapiens

<400> SEQUENCE: 42
```

-continued

```
Gly Ile Thr Phe Ser Arg Tyr Ala Ile Ser
1               5                   10

<210> SEQ ID NO 43
<211> LENGTH: 16
<212> TYPE: PRT
<213> ORGANISM: Homo sapiens

<400> SEQUENCE: 43

Thr Ile Ser Ser Gly Asp Ser Tyr Thr Tyr Tyr Leu Asp Ser Val Lys
1               5                   10                  15

<210> SEQ ID NO 44
<211> LENGTH: 9
<212> TYPE: PRT
<213> ORGANISM: Homo sapiens

<400> SEQUENCE: 44

Leu Gly Tyr Gly Asn Ala Met Asp Tyr
1               5

<210> SEQ ID NO 45
<211> LENGTH: 354
<212> TYPE: DNA
<213> ORGANISM: Homo sapiens

<400> SEQUENCE: 45
gaggtgaagc tggtggagtc tgggggaggc ttagtgaggc ctggagggtc cctgaaagtg        60
tcctgtgcag cctctggaat cactttcagt cgctatgcca tatcttgggt tcgccagact       120
ccggagaaga ggctggagtg ggtcgcaact attagtagcg gtgatagtta cacctactat       180
ttggacagtg tgaaggggcg attcaccatc tccagagacg atgccaagaa caccctgtat       240
ctgcaaatga gcagtctgag gtctgaggac acggccatgt attactgtgg aagactgggg       300
tatggtaatg ctatggacta ctggggtcaa ggaacctcag tcaccgtctc ctca            354

<210> SEQ ID NO 46
<211> LENGTH: 113
<212> TYPE: PRT
<213> ORGANISM: Homo sapiens

<400> SEQUENCE: 46

Asn Ile Met Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys

<210> SEQ ID NO 47
<211> LENGTH: 17
```

-continued

```
<212> TYPE: PRT
<213> ORGANISM: Homo sapiens

<400> SEQUENCE: 47

Lys Ser Ser Gln Ser Leu Leu Asn Ser Gly Asn Gln Lys Asn Tyr Leu
1               5                   10                  15

Thr

<210> SEQ ID NO 48
<211> LENGTH: 7
<212> TYPE: PRT
<213> ORGANISM: Homo sapiens

<400> SEQUENCE: 48

Trp Ala Ser Thr Arg Glu Ser
1               5

<210> SEQ ID NO 49
<211> LENGTH: 9
<212> TYPE: PRT
<213> ORGANISM: Homo sapiens

<400> SEQUENCE: 49

Gln Asn Asp Tyr Ser Tyr Pro Leu Thr
1               5

<210> SEQ ID NO 50
<211> LENGTH: 339
<212> TYPE: DNA
<213> ORGANISM: Homo sapiens

<400> SEQUENCE: 50
aacattatga tgacacagtc tccatcctcc ctgactgtga cagcaggaga gaaggtcact      60
atgagctgca agtccagtca gagtctgtta aacagtggaa atcaaaagaa ctacttgacc     120
tggtaccagc agaaaccagg gcagcctcct aaactgttga tctactgggc atccactagg     180
gaatctgggg tccctgatcg cttcacaggc agtggatctg gaacagattt cactctcacc     240
atcagcagtg tgcaggctga agacctggca gtttattact gtcagaatga ttatagttat     300
cctctcacgt tcggtgctgg gaccaagctg gaaatcaaa                            339

<210> SEQ ID NO 51
<211> LENGTH: 118
<212> TYPE: PRT
<213> ORGANISM: Homo sapiens

<400> SEQUENCE: 51

Glu Val Gln Leu Val Glu Ser Gly Gly Gly Leu Val Lys Pro Gly Gly
1               5                   10                  15

Ser Leu Lys Leu Ser Cys Ala Val Ser Gly Phe Thr Ile Asn Asn Tyr
            20                  25                  30

Gly Met Ser Trp Val Arg Gln Thr Pro Glu Lys Arg Leu Glu Trp Val
        35                  40                  45

Ala Thr Ile Ile Gly Gly Gly Ser Ser Thr Tyr Tyr Pro Asp Ser Leu
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Val Arg Leu Tyr Phe Gly Asn Ser Phe Ala Tyr Trp Gly Gln Gly Thr
```

```
              100             105             110

Leu Val Thr Val Ser Ala
        115

<210> SEQ ID NO 52
<211> LENGTH: 10
<212> TYPE: PRT
<213> ORGANISM: Homo sapiens

<400> SEQUENCE: 52

Gly Phe Thr Ile Asn Asn Tyr Gly Met Ser
1               5               10

<210> SEQ ID NO 53
<211> LENGTH: 16
<212> TYPE: PRT
<213> ORGANISM: Homo sapiens

<400> SEQUENCE: 53

Thr Ile Ile Gly Gly Gly Ser Ser Thr Tyr Tyr Pro Asp Ser Leu Lys
1               5               10              15

<210> SEQ ID NO 54
<211> LENGTH: 9
<212> TYPE: PRT
<213> ORGANISM: Homo sapiens

<400> SEQUENCE: 54

Leu Tyr Phe Gly Asn Ser Phe Ala Tyr
1               5

<210> SEQ ID NO 55
<211> LENGTH: 354
<212> TYPE: DNA
<213> ORGANISM: Homo sapiens

<400> SEQUENCE: 55
gaggtgcagc tggtggagtc tggggggaggc ttagtgaagc ctggagggtc cctgaaactc      60
tcctgtgcag tctctggatt cactatcaat aactatggca tgtcttgggt tcgccagact      120
ccggagaaga ggctggagtg ggtcgcaacc attattggtg gtggtagttc cacctactat      180
cctgacagtt tgaaggggcg attcaccatc tccagacaca tgccaagaa caacctgtac      240 ctgcaaatga gcagtctgag gtctgaggac acggccttgt attactgtgt aagactctac      300
tttggtaact cctttgctta ctggggccaa gggactctgg tcactgtctc tgca           354

<210> SEQ ID NO 56
<211> LENGTH: 113
<212> TYPE: PRT
<213> ORGANISM: Homo sapiens

<400> SEQUENCE: 56

Asp Ile Val Met Thr Gln Ser Pro Ser Ser Leu Thr Val Thr Ala Gly
1               5               10              15

Glu Lys Val Thr Val Ser Cys Lys Ser Ser Gln Ser Leu Asn Ser
            20              25              30

Gly Asn Gln Arg Asn Tyr Leu Thr Trp Tyr Gln Gln Lys Pro Gly Gln
        35              40              45

Pro Pro Lys Leu Leu Ile Tyr Trp Ala Ser Thr Arg Glu Ser Gly Val
    50              55              60

Pro Asp Arg Phe Thr Gly Ser Gly Ser Gly Thr Asp Phe Thr Leu Thr
```

-continued

```
          65                  70                  75                  80
Ile Ser Ser Val Gln Ala Glu Asp Leu Ala Val Tyr Tyr Cys Gln Asn
                    85                  90                  95

Asn Tyr Phe Tyr Pro Leu Thr Phe Gly Ala Gly Thr Lys Leu Glu Leu
                100                 105                 110

Lys
```

<210> SEQ ID NO 57
<211> LENGTH: 17
<212> TYPE: PRT
<213> ORGANISM: Homo sapiens

<400> SEQUENCE: 57

```
Lys Ser Ser Gln Ser Leu Ser Asn Ser Gly Asn Gln Arg Asn Tyr Leu
1               5                   10                  15

Thr
```

<210> SEQ ID NO 58
<211> LENGTH: 7
<212> TYPE: PRT
<213> ORGANISM: Homo sapiens

<400> SEQUENCE: 58

```
Trp Ala Ser Thr Arg Glu Ser
1               5
```

<210> SEQ ID NO 59
<211> LENGTH: 9
<212> TYPE: PRT
<213> ORGANISM: Homo sapiens

<400> SEQUENCE: 59

```
Gln Asn Asn Tyr Phe Tyr Pro Leu Thr
1               5
```

<210> SEQ ID NO 60
<211> LENGTH: 339
<212> TYPE: DNA
<213> ORGANISM: Homo sapiens

<400> SEQUENCE: 60

```
gacattgtga tgactcagtc tccatcctct ctgactgtga cagcaggaga gaaggtcact      60
gtgagctgca agtccagtca gagtctgtca aacagtggaa atcaaaggaa ctacttgacc     120
tggtaccagc agaaaccagg gcagcctcct aaactgttga tctactgggc atccactagg     180
gaatctgggg tccctgatcg cttcacaggc agtggatctg gaacagattt cactctcacc     240
atcagcagtg tgcaggctga agacctggca gtttattact gtcagaataa ttattttat      300 ccgctcacgt tcggtgctgg gaccaagctg gagctgaaa                            339
```

<210> SEQ ID NO 61
<211> LENGTH: 118
<212> TYPE: PRT
<213> ORGANISM: Homo sapiens

<400> SEQUENCE: 61

```
Gln Val Gln Leu Gln Gln Ser Gly Ala Glu Leu Val Lys Pro Gly Tyr
1               5                   10                  15

Ser Val Lys Leu Ser Cys Lys Ala Ser Gly Tyr Thr Phe Thr Asn Phe
                20                  25                  30
```

```
Gly Ile Asn Trp Val Arg Gln Arg Pro Glu Lys Gly Leu Glu Trp Ile
        35                  40                  45

Gly Trp Ile Phe Pro Gly Asp Gly Thr Thr Lys Tyr Asn Glu Asn Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Phe Tyr Tyr Gly Asn Ser Phe Val Asn Trp Gly Gln Gly Thr
            100                 105                 110

Leu Val Thr Val Ser Ala
        115
```

```
<210> SEQ ID NO 62
<211> LENGTH: 10
<212> TYPE: PRT
<213> ORGANISM: Homo sapiens

<400> SEQUENCE: 62

Gly Tyr Thr Phe Thr Asn Phe Gly Ile Asn
1               5                   10
```

```
<210> SEQ ID NO 63
<211> LENGTH: 16
<212> TYPE: PRT
<213> ORGANISM: Homo sapiens

<400> SEQUENCE: 63

Trp Ile Phe Pro Gly Asp Gly Thr Thr Lys Tyr Asn Glu Asn Phe Lys
1               5                   10                  15
```

```
<210> SEQ ID NO 64
<211> LENGTH: 9
<212> TYPE: PRT
<213> ORGANISM: Homo sapiens

<400> SEQUENCE: 64

Phe Tyr Tyr Gly Asn Ser Phe Val Asn
1               5
```

```
<210> SEQ ID NO 65
<211> LENGTH: 355
<212> TYPE: DNA
<213> ORGANISM: Homo sapiens

<400> SEQUENCE: 65
caggttcagc tgcaacagtc tggagctgaa ctggtcaagc ctgggtattc agtgaagttg      60
tcctgcaagg cttctggcta caccttcaca aattttggta taaactgggt gaggcagagg     120
cctgaaaagg gacttgagtg gattggatgg atttttcctg gagatggcac tactaaatac     180
aatgagaact tcaagggtaa ggccacactg acaacagaca atcctccag cacagcctac      240 atgcagctca gcaggctgac atctgaagac tctgctgtct atttctgtgc aaggttctac     300
tacggtaact cctttgttaa ctggggccaa gggactctgg tcactgtctc tgcag         355
```

```
<210> SEQ ID NO 66
<211> LENGTH: 113
<212> TYPE: PRT
<213> ORGANISM: Homo sapiens

<400> SEQUENCE: 66
```

Asp Ile Val Met Thr Gln Ser Pro Ser Ser Leu Thr Val Thr Ala Gly
1               5                   10                  15

Glu Lys Val Thr Leu Ser Cys Lys Ser Ser Gln Thr Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile His Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asn Tyr Phe Tyr Pro Leu Thr Phe Gly Ala Gly Thr Lys Leu Glu Ile
                100                 105                 110

Lys

<210> SEQ ID NO 67
<211> LENGTH: 17
<212> TYPE: PRT
<213> ORGANISM: Homo sapiens

<400> SEQUENCE: 67

Lys Ser Ser Gln Thr Leu Leu Asn Ser Gly Asn Gln Lys Asn Tyr Leu
1               5                   10                  15

Thr

<210> SEQ ID NO 68
<211> LENGTH: 7
<212> TYPE: PRT
<213> ORGANISM: Homo sapiens

<400> SEQUENCE: 68

Trp Ala Ser Thr Arg Glu Ser
1               5

<210> SEQ ID NO 69
<211> LENGTH: 9
<212> TYPE: PRT
<213> ORGANISM: Homo sapiens

<400> SEQUENCE: 69

Gln Asn Asn Tyr Phe Tyr Pro Leu Thr
1               5

<210> SEQ ID NO 70
<211> LENGTH: 339
<212> TYPE: DNA
<213> ORGANISM: Homo sapiens

<400> SEQUENCE: 70
gacattgtga tgacacagtc tccatcctcc ctgactgtga cagcaggaga gaaggtcact      60
ctgagctgca agtccagtca gactctgtta aacagtggaa atcaaaagaa ctacttgacg     120
tggtaccagc agaaaccggg gcagcctcct aaactgttga tccactgggc atccactagg     180
gaatctgggg tccctgatcg cttcacaggc agtggatctg gaacagattt cactctcacc     240
atcagcagtg tgcaggctga agacctggca gtttattact gtcagaataa ttattttttat     300 ccgctcacgt tcggtgctgg gaccaagctg gaaatcaaa                            339

```
<210> SEQ ID NO 71
<211> LENGTH: 117
<212> TYPE: PRT
<213> ORGANISM: Homo sapiens

<400> SEQUENCE: 71

Gln Val Gln Leu Gln Gln Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Gly Val Ser Trp Ile Arg Gln Pro Pro Gly Lys Gly Leu Glu Trp Leu
        35                  40                  45

Gly Ala Ile Trp Ala Gly Gly Asn Thr Asn Tyr Asn Ser Ala Leu Met
    50                  55                  60

Ser Arg Leu Ser Ile Arg Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Val Gly Tyr Gly Asn Ser Phe Ala Asn Trp Gly Gln Gly Thr Leu
            100                 105                 110

Val Thr Val Ser Ala
        115

<210> SEQ ID NO 72
<211> LENGTH: 10
<212> TYPE: PRT
<213> ORGANISM: Homo sapiens

<400> SEQUENCE: 72

Gly Phe Ser Leu Thr Asn Tyr Gly Val Ser
1               5                   10

<210> SEQ ID NO 73
<211> LENGTH: 16
<212> TYPE: PRT
<213> ORGANISM: Homo sapiens

<400> SEQUENCE: 73

Ala Ile Trp Ala Gly Gly Asn Thr Asn Tyr Asn Ser Ala Leu Met Ser
1               5                   10                  15

<210> SEQ ID NO 74
<211> LENGTH: 9
<212> TYPE: PRT
<213> ORGANISM: Homo sapiens

<400> SEQUENCE: 74

Val Gly Tyr Gly Asn Ser Phe Ala Asn
1               5

<210> SEQ ID NO 75
<211> LENGTH: 351
<212> TYPE: DNA
<213> ORGANISM: Homo sapiens

<400> SEQUENCE: 75
caggtccagc tgcagcagtc aggacctggc ctggtggcgc cctcacagag cctgtccatc        60
acttgcactg tctctgggtt ttcattgacc aactatggtg tttcctggat tcgccagcct       120
ccaggaaagg gtctggagtg gctgggagca atatgggctg ttggaaacac aaattataat       180
tcggctctca tgtccagact gagcatcagg aaagacaatt ccaagagcca agtttttctta       240
```

-continued aaaatgaaca gtctccaaac tgatgacaca gccatgtact actgtgccag agtagggtat          300
ggtaactcgt ttgctaactg gggccaaggg actctggtca ctgtctctgc a          351

<210> SEQ ID NO 76
<211> LENGTH: 113
<212> TYPE: PRT
<213> ORGANISM: Homo sapiens

<400> SEQUENCE: 76

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Leu Arg Asn Tyr Leu Thr Trp Tyr Gln Gln Lys Pro Gly Arg
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asn Tyr Phe Tyr Pro Leu Thr Phe Gly Ala Gly Thr Lys Leu Glu Leu
            100                 105                 110

Lys

<210> SEQ ID NO 77
<211> LENGTH: 17
<212> TYPE: PRT
<213> ORGANISM: Homo sapiens

<400> SEQUENCE: 77

Lys Ser Ser Gln Ser Leu Leu Asn Ser Gly Asn Leu Arg Asn Tyr Leu
1               5                   10                  15

Thr

<210> SEQ ID NO 78
<211> LENGTH: 7
<212> TYPE: PRT
<213> ORGANISM: Homo sapiens

<400> SEQUENCE: 78

Trp Ala Ser Thr Arg Glu Ser
1               5

<210> SEQ ID NO 79
<211> LENGTH: 9
<212> TYPE: PRT
<213> ORGANISM: Homo sapiens

<400> SEQUENCE: 79

Gln Asn Asn Tyr Phe Tyr Pro Leu Thr
1               5

<210> SEQ ID NO 80
<211> LENGTH: 339
<212> TYPE: DNA
<213> ORGANISM: Homo sapiens

<400> SEQUENCE: 80

-continued

```
gacattgtga tgacacagtc tccatcctcc ctgactgtga cagcaggaga gaaggtcact      60
atgagctgca agtccagtca gagtctgtta aacagtggaa atctaaggaa ctacttgacc     120
tggtaccagc agaaaccagg gcggcctcct aaactgttga tctactgggc atccactagg     180
gaatctgggg tccctgatcg cttcacaggc agtggatctg ggacagattt cactctcacc     240
atcagcagtg tgcaggctga agacctggca gtttattact gtcagaataa ttattttttat    300 ccgctcacgt tcggtgctgg gaccaagctg gagctgaaa                            339
```

<210> SEQ ID NO 81
<211> LENGTH: 118
<212> TYPE: PRT
<213> ORGANISM: Homo sapiens

<400> SEQUENCE: 81

```
Glu Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Ile Asn Trp Val Lys Gln Ala Pro Gly Lys Gly Leu Lys Trp Met
        35                  40                  45

Gly Trp Ile Asn Pro Asn Thr Gly Glu Thr Thr Tyr Ala Glu Glu Phe
    50                  55                  60

Lys Gly Arg Phe Ala Leu Ser Trp Lys Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Leu Tyr Tyr Gly Asn Arg Phe Asp Tyr Trp Gly Gln Gly Thr
            100                 105                 110

Thr Leu Thr Val Ser Ser
        115
```

<210> SEQ ID NO 82
<211> LENGTH: 10
<212> TYPE: PRT
<213> ORGANISM: Homo sapiens

<400> SEQUENCE: 82

```
Gly Tyr Thr Phe Thr Asn Tyr Gly Ile Asn
1               5                   10
```

<210> SEQ ID NO 83
<211> LENGTH: 16
<212> TYPE: PRT
<213> ORGANISM: Homo sapiens

<400> SEQUENCE: 83

```
Trp Ile Asn Pro Asn Thr Gly Glu Thr Thr Tyr Ala Glu Glu Phe Lys
1               5                   10                  15
```

<210> SEQ ID NO 84
<211> LENGTH: 9
<212> TYPE: PRT
<213> ORGANISM: Homo sapiens

<400> SEQUENCE: 84

```
Leu Tyr Tyr Gly Asn Arg Phe Asp Tyr
1               5
```

<210> SEQ ID NO 85

```
<211> LENGTH: 354
<212> TYPE: DNA
<213> ORGANISM: Homo sapiens

<400> SEQUENCE: 85
gagatccagt tggtgcagtc tggacctgag ctgaagaagc ctggagagac agtcaagatc      60
tcctgcaagg cttctggata tacctttaca aactatggaa taaactgggt gaagcaggct     120
ccaggaaagg gtttaaagtg gatgggctgg ataaacccca cactggagaa acaacatat      180 gctgaagagt tcaagggacg gtttgccctc tcttggaaaa cctctgccag cactgcctat     240
ttgcagatca caacctcaa aaatgaggac acggctacat atttctgtgc aagactctac      300
tatggtaatc gatttgacta ctggggccaa ggcaccactc tcacagtctc ctca           354

<210> SEQ ID NO 86
<211> LENGTH: 113
<212> TYPE: PRT
<213> ORGANISM: Homo sapiens

<400> SEQUENCE: 86

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Arg Asn Tyr Leu Thr Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Ala Tyr Tyr Tyr Pro Leu Thr Phe Gly Ala Gly Thr Lys Leu Glu Ile
            100                 105                 110

Lys

<210> SEQ ID NO 87
<211> LENGTH: 17
<212> TYPE: PRT
<213> ORGANISM: Homo sapiens

<400> SEQUENCE: 87

Lys Ser Ser Gln Ser Leu Leu Asn Ser Gly Asn Gln Arg Asn Tyr Leu
1               5                   10                  15

Thr

<210> SEQ ID NO 88
<211> LENGTH: 7
<212> TYPE: PRT
<213> ORGANISM: Homo sapiens

<400> SEQUENCE: 88

Trp Ala Ser Thr Arg Glu Ser
1               5

<210> SEQ ID NO 89
<211> LENGTH: 9
<212> TYPE: PRT
<213> ORGANISM: Homo sapiens
```

<400> SEQUENCE: 89

Gln Asn Ala Tyr Tyr Tyr Pro Leu Thr
1               5

<210> SEQ ID NO 90
<211> LENGTH: 339
<212> TYPE: DNA
<213> ORGANISM: Homo sapiens

<400> SEQUENCE: 90
gacattgtga tgacacagtc tccctcctcc ctgactgtga cagcaggaga gaaggtcact      60
atgagctgca agtccagtca gagtctatta aacagtggaa atcaaaggaa ctatttgacc     120
tggtaccagc agaagccagg gcagcctcct aaactattga tctactgggc atccactagg     180
gaatctgggg tccctgatcg cttcacaggc agtggatctg aacagatttt cactctcacc     240
atcagcagtg tgcaggctga agacctggca gtttattact gccagaatgc ttattattat     300
ccgctcacgt tcggtgctgg gaccaagctg gaaatcaaa                            339

<210> SEQ ID NO 91
<211> LENGTH: 118
<212> TYPE: PRT
<213> ORGANISM: Homo sapiens

<400> SEQUENCE: 91

Gln Val Gln Leu Gln Gln Ser Gly Arg Glu Val Val Arg Pro Gly Thr
1               5                   10                  15

Ser Val Lys Val Ser Cys Lys Pro Ser Gly Tyr Ala Phe Thr Asn Tyr
            20                  25                  30

Leu Ile Asp Trp Val Lys Gln Arg Pro Gly Gln Gly Leu Glu Trp Ile
        35                  40                  45

Gly Gly Ile Asn Pro Gly Ser Gly Asp Thr Val Tyr Asn Glu Lys Phe
    50                  55                  60

Lys Ala Lys Ala Thr Leu Thr Ala Asp Lys Ser Ser Met Thr Ala Asn
65                  70                  75                  80

Met Gln Leu Ser Ser Leu Thr Ser Asp Asp Ser Ala Val Tyr Phe Cys
                85                  90                  95

Ala Arg Arg Val Arg Gly Asn Ser Phe Asp Ser Trp Gly Gln Gly Thr
            100                 105                 110

Leu Val Thr Val Ser Ala
        115

<210> SEQ ID NO 92
<211> LENGTH: 10
<212> TYPE: PRT
<213> ORGANISM: Homo sapiens

<400> SEQUENCE: 92

Gly Tyr Ala Phe Thr Asn Tyr Leu Ile Asp
1               5                   10

<210> SEQ ID NO 93
<211> LENGTH: 16
<212> TYPE: PRT
<213> ORGANISM: Homo sapiens

<400> SEQUENCE: 93

Gly Ile Asn Pro Gly Ser Gly Asp Thr Val Tyr Asn Glu Lys Phe Lys
1               5                   10                  15

-continued

```
<210> SEQ ID NO 94
<211> LENGTH: 9
<212> TYPE: PRT
<213> ORGANISM: Homo sapiens

<400> SEQUENCE: 94

Arg Val Arg Gly Asn Ser Phe Asp Ser
1               5

<210> SEQ ID NO 95
<211> LENGTH: 354
<212> TYPE: DNA
<213> ORGANISM: Homo sapiens

<400> SEQUENCE: 95
caggtgcagc tgcagcagtc tggacgtgag gtggtaaggc ctgggacttc agtgaaggtg      60
tcctgcaagc cttctggata cgccttcact aattacttga tagactgggt aaaacagagg     120
cctggacagg gccttgagtg gattggaggg attaatcctg aagtggtga cactgtgtac      180 aatgagaagt tcaaggccaa ggcaacactg actgcagaca atcctccat gactgccaac      240 atgcagctca gcagcctgac atctgatgac tctgcggtct atttctgcgc aagaagggtc     300
cgtggtaatt cgtttgattc ctggggccaa gggactctgg tcactgtctc tgca           354

<210> SEQ ID NO 96
<211> LENGTH: 113
<212> TYPE: PRT
<213> ORGANISM: Homo sapiens

<400> SEQUENCE: 96

Asp Ile Val Met Ser Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Lys Asp Phe Thr Leu Thr
65                  70                  75                  80

Ile Ser Ser Val Gln Ala Glu Asp Leu Ala Leu Tyr Tyr Cys Gln Asn
                85                  90                  95

Asn Tyr Phe Tyr Pro Leu Thr Phe Gly Ala Gly Thr Lys Leu Glu Leu
            100                 105                 110

Lys

<210> SEQ ID NO 97
<211> LENGTH: 17
<212> TYPE: PRT
<213> ORGANISM: Homo sapiens

<400> SEQUENCE: 97

Lys Ser Ser Gln Ser Leu Leu Asn Ser Gly Asn Gln Lys Asn Tyr Leu
1               5                   10                  15

Thr

<210> SEQ ID NO 98
<211> LENGTH: 7
<212> TYPE: PRT
```

<213> ORGANISM: Homo sapiens

<400> SEQUENCE: 98

Trp Ala Ser Thr Arg Glu Ser
1               5

<210> SEQ ID NO 99
<211> LENGTH: 9
<212> TYPE: PRT
<213> ORGANISM: Homo sapiens

<400> SEQUENCE: 99

Gln Asn Asn Tyr Phe Tyr Pro Leu Thr
1               5

<210> SEQ ID NO 100
<211> LENGTH: 339
<212> TYPE: DNA
<213> ORGANISM: Homo sapiens

<400> SEQUENCE: 100
gacattgtga tgtcacagtc tccatcctcc ctgactgtga cagcaggaga gaaggtcact          60
atgagctgca agtccagtca gagtctgtta aacagtggaa atcaaaagaa ctacttgacc         120
tggtaccagc agaaaccagg gcagcctcct aaattgttga tctactgggc atccactagg         180
gaatctgggg tccctgatcg cttcacaggc agtggatctg aaaagatttt cactctcacc         240
atcagcagtg tgcaggctga agacctggca ctttattact gtcagaataa ttattttttat        300 ccgctcacgt tcggtgctgg gaccaagctg gagctgaaa                                339

<210> SEQ ID NO 101
<211> LENGTH: 118
<212> TYPE: PRT
<213> ORGANISM: Homo sapiens

<400> SEQUENCE: 101

Glu Val Gln Leu Gln Gln Ser Gly Arg Glu Val Val Arg Pro Gly Thr
1               5                   10                  15

Ser Val Lys Val Ser Cys Lys Pro Ser Gly Tyr Ala Phe Thr Asn Tyr
                20                  25                  30

Leu Ile Asp Trp Val Lys Gln Arg Pro Gly Gln Gly Leu Glu Trp Ile
            35                  40                  45

Gly Gly Ile Asn Pro Gly Ser Gly Asp Thr Val Tyr Asn Glu Lys Phe
        50                  55                  60

Lys Ala Lys Ala Thr Leu Thr Ala Asp Lys Ser Ser Met Thr Thr Asn
65                  70                  75                  80

Met Gln Leu Ser Ser Leu Thr Ser Asp Asp Ser Ala Val Tyr Phe Cys
                85                  90                  95

Ala Arg Arg Val Arg Gly Asn Ser Phe Asp Ser Trp Gly Gln Gly Thr
                100                 105                 110

Leu Val Thr Val Ser Ala
        115

<210> SEQ ID NO 102
<211> LENGTH: 10
<212> TYPE: PRT
<213> ORGANISM: Homo sapiens

<400> SEQUENCE: 102

Gly Tyr Ala Phe Thr Asn Tyr Leu Ile Asp

-continued

```
1           5              10
```

<210> SEQ ID NO 103
<211> LENGTH: 16
<212> TYPE: PRT
<213> ORGANISM: Homo sapiens

<400> SEQUENCE: 103

```
Gly Ile Asn Pro Gly Ser Gly Asp Thr Val Tyr Asn Glu Lys Phe Lys
1               5               10              15
```

<210> SEQ ID NO 104
<211> LENGTH: 9
<212> TYPE: PRT
<213> ORGANISM: Homo sapiens

<400> SEQUENCE: 104

```
Arg Val Arg Gly Asn Ser Phe Asp Ser
1               5
```

<210> SEQ ID NO 105
<211> LENGTH: 354
<212> TYPE: DNA
<213> ORGANISM: Homo sapiens

<400> SEQUENCE: 105

```
gaggtccagc tgcagcagtc tggacgtgag gtggtaaggc ctgggacttc agtgaaggtg      60
tcctgcaagc cttctggata cgccttcact aattacttga tagactgggt aaaacagagg     120
cctggacagg gccttgagtg gattggaggg attaatcctg aagtggtga cactgtgtac      180 aatgagaagt tcaaggccaa ggcaacactg actgcagaca atcctccat gactaccaac      240 atgcagctca gcagcctgac atctgatgac tctgcggtct atttctgcgc aagaagggtc     300
cgtggtaatt cgtttgattc ctggggccaa gggactctgg tcactgtctc tgca           354
```

<210> SEQ ID NO 106
<211> LENGTH: 113
<212> TYPE: PRT
<213> ORGANISM: Homo sapiens

<400> SEQUENCE: 106

```
Asp Ile Val Met Thr Gln Ser Pro Ser Ser Leu Thr Val Arg Ala Gly
1               5               10              15

Glu Lys Val Thr Met Thr Cys Lys Ser Ser Gln Ser Leu Phe Asn Ser
                20              25              30

Gly Asn Gln Arg Asn Tyr Leu Thr Trp Tyr Gln Gln Lys Pro Gly Gln
            35              40              45

Pro Pro Lys Leu Leu Leu Tyr Trp Ala Thr Ala Arg Glu Ser Gly Val
        50              55              60

Pro Asp Arg Phe Thr Gly Ser Gly Ser Gly Thr Asp Phe Thr Leu Ser
65              70              75              80

Ile Ser Ser Val Gln Ala Glu Asp Leu Ala Val Tyr Tyr Cys Gln Asn
                85              90              95

Val Tyr Phe Tyr Pro Leu Thr Phe Gly Ala Gly Thr Lys Leu Glu Ile
            100             105             110

Lys
```

<210> SEQ ID NO 107
<211> LENGTH: 17
<212> TYPE: PRT

<213> ORGANISM: Homo sapiens

<400> SEQUENCE: 107

Lys Ser Ser Gln Ser Leu Phe Asn Ser Gly Asn Gln Arg Asn Tyr Leu
1               5                   10                  15

Thr

<210> SEQ ID NO 108
<211> LENGTH: 7
<212> TYPE: PRT
<213> ORGANISM: Homo sapiens

<400> SEQUENCE: 108

Trp Ala Thr Ala Arg Glu Ser
1               5

<210> SEQ ID NO 109
<211> LENGTH: 9
<212> TYPE: PRT
<213> ORGANISM: Homo sapiens

<400> SEQUENCE: 109

Gln Asn Val Tyr Phe Tyr Pro Leu Thr
1               5

<210> SEQ ID NO 110
<211> LENGTH: 339
<212> TYPE: DNA
<213> ORGANISM: Homo sapiens

<400> SEQUENCE: 110
gacattgtga tgacacagtc tccatcctcc ctgactgtga gagcaggaga gaaggtcact      60
atgacctgca agtccagtca gagtctgttt aacagtggaa atcaaaggaa ctacttgacc     120
tggtaccagc agaaaccagg gcagcctcct aaacttttgc tctactgggc aaccgctagg     180
gaatctgggg tccctgatcg cttcacaggc agtggttctg aacagatttt cactctctcc     240
atcagcagtg tgcaggctga agacctggca gtttattact gtcagaatgt ttatttttat     300
ccgctcacgt tcggtgctgg gaccaagctg gaaataaaa                            339

<210> SEQ ID NO 111
<211> LENGTH: 118
<212> TYPE: PRT
<213> ORGANISM: Homo sapiens

<400> SEQUENCE: 111

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asn
            20                  25                  30

Tyr Ala Trp Asn Trp Ile Arg Gln Phe Pro Gly Asn Lys Leu Glu Trp
        35                  40                  45

Met Gly Tyr Ile Asn Tyr Ser Gly Asn Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ala Glu Asp Thr Ala Thr Tyr Tyr Cys
                85                  90                  95

Ala Thr Ser Tyr Tyr Gly Asn Ser Phe Ile Tyr Trp Gly Gln Gly Thr
            100                 105                 110

Leu Val Thr Val Ser Ala
        115

<210> SEQ ID NO 112
<211> LENGTH: 11
<212> TYPE: PRT
<213> ORGANISM: Homo sapiens

<400> SEQUENCE: 112

Gly Tyr Ser Ile Thr Ser Asn Tyr Ala Trp Asn
1               5                   10

<210> SEQ ID NO 113
<211> LENGTH: 16
<212> TYPE: PRT
<213> ORGANISM: Homo sapiens

<400> SEQUENCE: 113

Tyr Ile Asn Tyr Ser Gly Asn Thr Asn Tyr Asn Pro Ser Leu Lys Ser
1               5                   10                  15

<210> SEQ ID NO 114
<211> LENGTH: 9
<212> TYPE: PRT
<213> ORGANISM: Homo sapiens

<400> SEQUENCE: 114

Ser Tyr Tyr Gly Asn Ser Phe Ile Tyr
1               5

<210> SEQ ID NO 115
<211> LENGTH: 354
<212> TYPE: DNA
<213> ORGANISM: Homo sapiens

<400> SEQUENCE: 115
gatgtgcagc ttcaggagtc gggacctggc ctggtgaaac cttctcagtc tctgtccctc        60
acctgcactg tcactggcta ctcaatcacc agtaattatg cctggaactg gatccgacag       120
tttccaggaa acaaactaga gtggatgggc tacataaact acagtgggaa cactaactat       180
aacccatctc tcaaaagtcg aatctctatc actcgagaca catccaagaa ccagttcttc       240
ctgcagttga attctgtgac tgctgaggac acagccacat attattgtgc aacctcctat       300
tatggtaatt cctttatttactggggccaa gggactctgg tcactgtctc tgca             354

<210> SEQ ID NO 116
<211> LENGTH: 113
<212> TYPE: PRT
<213> ORGANISM: Homo sapiens

<400> SEQUENCE: 116

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

-continued

```
Ile Ser Ser Val Gln Ala Glu Asp Leu Ala Val Tyr Tyr Cys Gln Asn
                 85                   90                   95

Ala Tyr Ser Phe Pro Trp Thr Phe Gly Gly Gly Thr Lys Leu Glu Ile
            100                  105                  110

Lys

<210> SEQ ID NO 117
<211> LENGTH: 17
<212> TYPE: PRT
<213> ORGANISM: Homo sapiens

<400> SEQUENCE: 117

Lys Ser Ser Gln Ser Leu Leu Asn Ser Gly Asn Gln Lys Asn Tyr Leu
1               5                   10                  15

Thr

<210> SEQ ID NO 118
<211> LENGTH: 7
<212> TYPE: PRT
<213> ORGANISM: Homo sapiens

<400> SEQUENCE: 118

Trp Ala Ser Thr Arg Glu Ser
1               5

<210> SEQ ID NO 119
<211> LENGTH: 9
<212> TYPE: PRT
<213> ORGANISM: Homo sapiens

<400> SEQUENCE: 119

Gln Asn Ala Tyr Ser Phe Pro Trp Thr
1               5

<210> SEQ ID NO 120
<211> LENGTH: 339
<212> TYPE: DNA
<213> ORGANISM: Homo sapiens

<400> SEQUENCE: 120
gacattgtga tgacacagtc tccatcctcc ctgactgtga cagcaggaga gaaggtcact     60
atgagctgca agtccagtca gagtctgtta aacagtggaa atcaaaagaa ctacttgacc    120
tggtaccagc agaaaccagg gcagcctcct aaactgttga tctactgggc atccactagg    180
gagtctgggg tccctgatcg cttcacaggc agtggatctg gaacagattt cactctcacc    240
atcagcagtg tgcaggctga agacctggca gtttattact gtcagaatgc ttatagtttt    300
ccgtggacgt tcggtggagg caccaagctg gaaatcaaa                           339

<210> SEQ ID NO 121
<211> LENGTH: 118
<212> TYPE: PRT
<213> ORGANISM: Homo sapiens

<400> SEQUENCE: 121

Gln Val Gln Leu Gln Gln Ser Gly Ala Glu Leu Val Lys Pro Gly Thr
1               5                   10                  15

Ser Val Lys Leu Ser Cys Lys Ala Ser Gly Tyr Ser Phe Thr Thr Tyr
            20                   25                   30

Gly Leu Asn Trp Val Arg Gln Arg Pro Lys Gln Gly Leu Glu Trp Ile
```

-continued

```
            35                  40                  45
Gly Trp Ile Phe Pro Gly Asp Gly Asn Val Asn Tyr Asn Glu Lys Phe
     50                  55                  60

Gln Gly Gln Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Phe Tyr Tyr Gly Asn Ser Leu Asn Tyr Trp Gly Gln Gly Thr
                100                 105                 110

Leu Val Thr Val Ser Ala
        115
```

```
<210> SEQ ID NO 122
<211> LENGTH: 10
<212> TYPE: PRT
<213> ORGANISM: Homo sapiens

<400> SEQUENCE: 122

Gly Tyr Ser Phe Thr Thr Tyr Gly Leu Asn
1               5                   10
```

```
<210> SEQ ID NO 123
<211> LENGTH: 16
<212> TYPE: PRT
<213> ORGANISM: Homo sapiens

<400> SEQUENCE: 123

Trp Ile Phe Pro Gly Asp Gly Asn Val Asn Tyr Asn Glu Lys Phe Gln
1               5                   10                  15
```

```
<210> SEQ ID NO 124
<211> LENGTH: 9
<212> TYPE: PRT
<213> ORGANISM: Homo sapiens

<400> SEQUENCE: 124

Phe Tyr Tyr Gly Asn Ser Leu Asn Tyr
1               5
```

```
<210> SEQ ID NO 125
<211> LENGTH: 354
<212> TYPE: DNA
<213> ORGANISM: Homo sapiens

<400> SEQUENCE: 125
caggtccagc tgcagcagtc tggagctgaa ctggtaaagc ctgggacttc agtgaagttg      60
tcctgcaagg cttctggcta ctccttcaca acctatggtc taaactgggt gaggcagagg     120
cctaaacagg gacttgagtg gattggatgg attttccctg gagatggtaa tgttaactac     180
aatgagaaat tcagggcca ggccacactg actacagaca atcctccag cacagcctac       240 atgcagctca gcaggctgac atctgaggac tctgctgtct atttctgtgc aaggttttat      300
tacggtaact ccttaaatta ctggggccaa gggactctgg tcactgtctc tgca            354
```

```
<210> SEQ ID NO 126
<211> LENGTH: 113
<212> TYPE: PRT
<213> ORGANISM: Homo sapiens

<400> SEQUENCE: 126

Asp Ile Val Met Thr Gln Ser Pro Ser Ser Leu Thr Val Thr Ala Gly
```

```
1               5               10              15
Glu Lys Val Thr Met Ser Cys Lys Ser Ser Gln Ser Leu Leu Asn Ser
                20              25              30

Gly Asn Leu Arg Asn Tyr Leu Thr Trp Tyr Gln Gln Lys Pro Gly Arg
        35              40              45

Pro Pro Lys Leu Leu Ile Tyr Trp Ala Ser Thr Arg Glu Ser Gly Val
    50              55              60

Pro Asp Arg Phe Thr Gly Ser Gly Ser Gly Thr Asp Phe Thr Leu Thr
65              70              75              80

Ile Ser Ser Val Gln Ala Glu Asp Leu Ala Val Tyr Tyr Cys Gln Asn
                85              90              95

Asn Tyr Phe Tyr Pro Leu Thr Phe Gly Ala Gly Thr Lys Leu Glu Ile
            100             105             110

Lys
```

<210> SEQ ID NO 127
<211> LENGTH: 17
<212> TYPE: PRT
<213> ORGANISM: Homo sapiens

<400> SEQUENCE: 127

```
Lys Ser Ser Gln Ser Leu Leu Asn Ser Gly Asn Leu Arg Asn Tyr Leu
1               5               10              15

Thr
```

<210> SEQ ID NO 128
<211> LENGTH: 7
<212> TYPE: PRT
<213> ORGANISM: Homo sapiens

<400> SEQUENCE: 128

```
Trp Ala Ser Thr Arg Glu Ser
1               5
```

<210> SEQ ID NO 129
<211> LENGTH: 9
<212> TYPE: PRT
<213> ORGANISM: Homo sapiens

<400> SEQUENCE: 129

```
Gln Asn Asn Tyr Phe Tyr Pro Leu Thr
1               5
```

<210> SEQ ID NO 130
<211> LENGTH: 339
<212> TYPE: DNA
<213> ORGANISM: Homo sapiens

<400> SEQUENCE: 130

```
gacattgtga tgacccagtc tccatcctcc ctgactgtga cagcaggaga gaaggtcact      60
atgagctgca agtccagtca gagtctgtta aacagtggaa atctaaggaa ctacttgacc     120
tggtaccagc agaaaccagg gcggcctcct aaactgttga tctactgggc atccactagg     180
gaatctgggg tccctgatcg cttcacaggc agtggatctg aacagatttt cactctcacc     240
atcagcagtg tgcaggctga agacctggca gtttattact gtcagaataa ttattttttat    300 ccgctcacgt tcggtgctgg gaccaagctg gaaatcaaa                            339
```

<210> SEQ ID NO 131

```
<211> LENGTH: 117
<212> TYPE: PRT
<213> ORGANISM: Homo sapiens

<400> SEQUENCE: 131

Glu Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Gly Val Ser Trp Ile Arg Gln Pro Pro Gly Lys Gly Leu Glu Trp Leu
        35                  40                  45

Gly Ala Ile Trp Ala Gly Gly Asn Thr Asn Tyr Asn Ser Ala Leu Met
    50                  55                  60

Ser Arg Leu Ser Ile Arg Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Val Gly Tyr Gly Asn Ser Phe Ala Asn Trp Gly Gln Gly Thr Leu
            100                 105                 110

Val Thr Val Ser Ala
        115

<210> SEQ ID NO 132
<211> LENGTH: 10
<212> TYPE: PRT
<213> ORGANISM: Homo sapiens

<400> SEQUENCE: 132

Gly Phe Ser Leu Thr Asn Tyr Gly Val Ser
1               5                   10

<210> SEQ ID NO 133
<211> LENGTH: 16
<212> TYPE: PRT
<213> ORGANISM: Homo sapiens

<400> SEQUENCE: 133

Ala Ile Trp Ala Gly Gly Asn Thr Asn Tyr Asn Ser Ala Leu Met Ser
1               5                   10                  15

<210> SEQ ID NO 134
<211> LENGTH: 9
<212> TYPE: PRT
<213> ORGANISM: Homo sapiens

<400> SEQUENCE: 134

Val Gly Tyr Gly Asn Ser Phe Ala Asn
1               5

<210> SEQ ID NO 135
<211> LENGTH: 351
<212> TYPE: DNA
<213> ORGANISM: Homo sapiens

<400> SEQUENCE: 135
gaggtccagc tgaaggagtc aggacctggc ctggtggcgc cctcacagag cctgtccatc       60
acttgcactg tctctgggtt ttcattgacc aactatggtg tttcctggat tcgccagcct      120
ccaggaaagg gtctggagtg ctgggagca atatgggctg gtggaaacac aaattataat       180
tcggctctca tgtccagact gagcatcagg aaagacaatt ccaagagcca agttttctta      240
```

-continued aaaatgaaca gtctccaaac tgatgacaca gccatgtact actgtgccag agtagggtat    300
ggtaactcgt ttgctaactg gggccaaggg actctggtca ctgtctctgc a           351

<210> SEQ ID NO 136
<211> LENGTH: 113
<212> TYPE: PRT
<213> ORGANISM: Homo sapiens

<400> SEQUENCE: 136

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Ile
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Val Ser Val Tyr Tyr Cys Gln Asn
                85                  90                  95

Asn Tyr Ile Phe Pro Leu Thr Phe Gly Ala Gly Thr Lys Leu Glu Ile
            100                 105                 110

Lys

<210> SEQ ID NO 137
<211> LENGTH: 17
<212> TYPE: PRT
<213> ORGANISM: Homo sapiens

<400> SEQUENCE: 137

Lys Ser Ser Gln Ser Leu Leu Asn Ser Gly Asn Gln Arg Asn Tyr Leu
1               5                   10                  15

Thr

<210> SEQ ID NO 138
<211> LENGTH: 7
<212> TYPE: PRT
<213> ORGANISM: Homo sapiens

<400> SEQUENCE: 138

Trp Ala Ser Thr Arg Glu Ser
1               5

<210> SEQ ID NO 139
<211> LENGTH: 9
<212> TYPE: PRT
<213> ORGANISM: Homo sapiens

<400> SEQUENCE: 139

Gln Asn Asn Tyr Ile Phe Pro Leu Thr
1               5

<210> SEQ ID NO 140
<211> LENGTH: 339
<212> TYPE: DNA
<213> ORGANISM: Homo sapiens

<400> SEQUENCE: 140
gacattgtga tgacacagtc tccatcctcc ctgactgtga cagcaggaga gaaggtcact    60

-continued

```
atgagctgca agtccagtca gagtctgtta aacagtggaa atcaaaggaa ctacttgacc        120
tggtaccagc agaaaccagg gcagcctcct aaactgttga tctactgggc atccactagg        180
gaatctggga tccctgatcg cttcataggc agtggatctg gaacagattt cactctcacc        240
atcagcagtg tgcaggctga agacgtgtca gtttattact gtcagaataa ttatattttt        300
cctctcacgt tcggtgctgg gaccaagctg gaaatcaaa                                339
```

```
<210> SEQ ID NO 141
<211> LENGTH: 118
<212> TYPE: PRT
<213> ORGANISM: Homo sapiens

<400> SEQUENCE: 141

Gln Val Gln Leu Lys Gln Ser Gly Ala Glu Leu Val Lys Pro Gly Ala
1               5                   10                  15

Ser Leu Lys Leu Ser Cys Lys Ala Ser Gly Tyr Thr Phe Thr Thr Tyr
            20                  25                  30

Gly Ile Asn Trp Val Arg Gln Arg Pro Glu Gln Gly Leu Glu Trp Ile
        35                  40                  45

Gly Trp Ile Phe Pro Gly Asp Ala Thr Thr Met Tyr Asn Glu Lys Phe
    50                  55                  60

Lys Gly Thr Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Phe Tyr Tyr Gly Asn Ser Phe Val Asp Trp Gly Gln Gly Thr
            100                 105                 110

Leu Val Thr Val Ser Ala
        115
```

```
<210> SEQ ID NO 142
<211> LENGTH: 10
<212> TYPE: PRT
<213> ORGANISM: Homo sapiens

<400> SEQUENCE: 142

Gly Tyr Thr Phe Thr Thr Tyr Gly Ile Asn
1               5                   10
```

```
<210> SEQ ID NO 143
<211> LENGTH: 16
<212> TYPE: PRT
<213> ORGANISM: Homo sapiens

<400> SEQUENCE: 143

Trp Ile Phe Pro Gly Asp Ala Thr Thr Met Tyr Asn Glu Lys Phe Lys
1               5                   10                  15
```

```
<210> SEQ ID NO 144
<211> LENGTH: 9
<212> TYPE: PRT
<213> ORGANISM: Homo sapiens

<400> SEQUENCE: 144

Phe Tyr Tyr Gly Asn Ser Phe Val Asp
1               5
```

```
<210> SEQ ID NO 145
<211> LENGTH: 354
```

<212> TYPE: DNA
<213> ORGANISM: Homo sapiens

<400> SEQUENCE: 145
caggtccagc tgaagcagtc tggagctgaa ctggtcaagc ctggggcttc actcaagttg        60
tcctgcaagg cttctggcta caccttcaca acttatggta taaactgggt gaggcagagg       120
cctgaacagg gacttgagtg gattggatgg attttctg gagatgcaac cactatgtac         180
aatgagaaat tcaagggcac ggccacactg actgcagaca atcctccag tacagcctac        240 atgcagctca gcgggttgac atctgaggac tctgctgtct atttctgtgc aaggttctac       300
tacggtaact cctttgttga ctgggggccaa gggactctgg tcactgtctc tgca            354

<210> SEQ ID NO 146
<211> LENGTH: 113
<212> TYPE: PRT
<213> ORGANISM: Homo sapiens

<400> SEQUENCE: 146

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Ala Tyr Tyr Tyr Pro Leu Thr Phe Gly Ala Gly Thr Lys Leu Glu Ile
            100                 105                 110

Lys

<210> SEQ ID NO 147
<211> LENGTH: 17
<212> TYPE: PRT
<213> ORGANISM: Homo sapiens

<400> SEQUENCE: 147

Lys Ser Ser Gln Ser Leu Leu Asn Ser Gly Asn Gln Lys Asn Tyr Leu
1               5                   10                  15

Thr

<210> SEQ ID NO 148
<211> LENGTH: 7
<212> TYPE: PRT
<213> ORGANISM: Homo sapiens

<400> SEQUENCE: 148

Trp Ala Ser Thr Arg Glu Ser
1               5

<210> SEQ ID NO 149
<211> LENGTH: 9
<212> TYPE: PRT
<213> ORGANISM: Homo sapiens

<400> SEQUENCE: 149

```
Gln Asn Ala Tyr Tyr Tyr Pro Leu Thr
1               5
```

<210> SEQ ID NO 150
<211> LENGTH: 339
<212> TYPE: DNA
<213> ORGANISM: Homo sapiens

<400> SEQUENCE: 150

```
gacattgtga tgacacagtc tccatcctcc ctgactgtga cagcaggaga gaaggtcact      60
atgagctgca gtccagtca gagtctgtta aacagtggaa atcaaaagaa ctacttgacc     120
tggtaccagc agaagccagg gcagcctcct aaactgttga tctactgggc atccactagg     180
gaatctgggg tccctgatcg cttcacaggc agtggatctg gaacagattt cactctcacc     240
atcagcagtg tgcaggctga agacctggca gtttattact gtcagaatgc ttattattat     300
ccgctcacgt tcggtgctgg gaccaagctg gaaatcaaa                            339
```

<210> SEQ ID NO 151
<211> LENGTH: 118
<212> TYPE: PRT
<213> ORGANISM: Homo sapiens

<400> SEQUENCE: 151

```
Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Asn Trp Val Arg Gln Ala Pro Gly Gln Gly Leu Glu Trp Met
        35                  40                  45

Gly Trp Ile Asn Pro Asn Thr Gly Glu Thr Thr Tyr Ala Glu Gly Phe
    50                  55                  60

Thr Gly Arg Phe Val Leu Ser Trp Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Leu Tyr Tyr Gly Asn Arg Phe Asp Ser Trp Gly Gln Gly Thr
            100                 105                 110

Leu Val Thr Val Ser Ser
        115
```

<210> SEQ ID NO 152
<211> LENGTH: 10
<212> TYPE: PRT
<213> ORGANISM: Homo sapiens

<400> SEQUENCE: 152

```
Gly Tyr Thr Phe Thr Asn Tyr Gly Ile Asn
1               5                   10
```

<210> SEQ ID NO 153
<211> LENGTH: 16
<212> TYPE: PRT
<213> ORGANISM: Homo sapiens

<400> SEQUENCE: 153

```
Trp Ile Asn Pro Asn Thr Gly Glu Thr Thr Tyr Ala Glu Gly Phe Thr
1               5                   10                  15
```

-continued

```
<210> SEQ ID NO 154
<211> LENGTH: 9
<212> TYPE: PRT
<213> ORGANISM: Homo sapiens

<400> SEQUENCE: 154

Leu Tyr Tyr Gly Asn Arg Phe Asp Ser
1               5

<210> SEQ ID NO 155
<211> LENGTH: 354
<212> TYPE: DNA
<213> ORGANISM: Homo sapiens

<400> SEQUENCE: 155
cagattcagc tggtgcagtc tggcagcgag ctgaagaaac ctggcgcctc tgtgaaggtg      60
tcctgcaagg ctagcggcta cacattcacc aactacggca tcaactgggt ccgacaggct     120
cctggacagg gactcgaatg gatgggctgg atcaacccca caccggcga dacaacatac      180 gccgagggct tcacaggcag attcgtgctg agctgggata ccagcgtcag cacagcttac     240
ctgcagatca gcagcctgaa ggccgaggat accgccgtgt acttctgcgc cagactgtac     300
tacggcaaca gattcgactc ttggggccag ggcacactgg tcacagtctc ttct           354

<210> SEQ ID NO 156
<211> LENGTH: 118
<212> TYPE: PRT
<213> ORGANISM: Homo sapiens

<400> SEQUENCE: 156

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Asn Trp Val Arg Gln Ala Pro Gly Gln Gly Leu Glu Trp Met
        35                  40                  45

Gly Trp Ile Asn Pro Asn Thr Gly Glu Thr Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Leu Tyr Tyr Gly Asn Arg Phe Asp Ser Trp Gly Gln Gly Thr
            100                 105                 110

Leu Val Thr Val Ser Ser
        115

<210> SEQ ID NO 157
<211> LENGTH: 10
<212> TYPE: PRT
<213> ORGANISM: Homo sapiens

<400> SEQUENCE: 157

Gly Tyr Thr Phe Thr Asn Tyr Gly Ile Asn
1               5                   10

<210> SEQ ID NO 158
<211> LENGTH: 16
<212> TYPE: PRT
<213> ORGANISM: Homo sapiens
```

<400> SEQUENCE: 158

Trp Ile Asn Pro Asn Thr Gly Glu Thr Thr Tyr Ala Glu Glu Phe Lys
1               5                   10                  15

<210> SEQ ID NO 159
<211> LENGTH: 9
<212> TYPE: PRT
<213> ORGANISM: Homo sapiens

<400> SEQUENCE: 159

Leu Tyr Tyr Gly Asn Arg Phe Asp Ser
1               5

<210> SEQ ID NO 160
<211> LENGTH: 354
<212> TYPE: DNA
<213> ORGANISM: Homo sapiens

<400> SEQUENCE: 160
caggtgcagc tggtgcagtc tggcagcgag ctgaagaaac ctggcgcctc tgtgaaggtg        60
tcctgcaagg ctagcggcta cacattcacc aactacggca tcaactgggt ccgacaggct       120
cctggacagg gactcgaatg gatgggctgg atcaacccca caccggcga gacaacatac       180 gccgaggagt tcaagggcag attcgtgttc agcctggata ccagcgtcag cacagcttac       240
ctgcagatca gcagcctgaa ggccgaggat accgccgtgt acttctgcgc cagactgtac       300
tacggcaaca gattcgactc ttggggccag ggcacactgg tcacagtctc ttct            354

<210> SEQ ID NO 161
<211> LENGTH: 118
<212> TYPE: PRT
<213> ORGANISM: Homo sapiens

<400> SEQUENCE: 161

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Ile Asn Trp Val Arg Gln Ala Pro Gly Gln Gly Leu Glu Trp Met
            35                  40                  45

Gly Trp Ile Asn Pro Tyr Thr Gly Glu Thr Thr Tyr Ala Glu Glu Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Leu Tyr Tyr Gly Asn Arg Phe Asp Ser Trp Gly Gln Gly Thr
            100                 105                 110

Leu Val Thr Val Ser Ser
        115

<210> SEQ ID NO 162
<211> LENGTH: 10
<212> TYPE: PRT
<213> ORGANISM: Homo sapiens

<400> SEQUENCE: 162

Gly Tyr Thr Phe Thr Asn Tyr Gly Ile Asn
1               5                   10

<210> SEQ ID NO 163
<211> LENGTH: 16
<212> TYPE: PRT
<213> ORGANISM: Homo sapiens

<400> SEQUENCE: 163

Trp Ile Asn Pro Tyr Thr Gly Glu Thr Thr Tyr Ala Glu Glu Phe Lys
1               5                   10                  15

<210> SEQ ID NO 164
<211> LENGTH: 9
<212> TYPE: PRT
<213> ORGANISM: Homo sapiens

<400> SEQUENCE: 164

Leu Tyr Tyr Gly Asn Arg Phe Asp Ser
1               5

<210> SEQ ID NO 165
<211> LENGTH: 354
<212> TYPE: DNA
<213> ORGANISM: Homo sapiens

<400> SEQUENCE: 165
gaggtgcagc tggtgcagtc tggcagcgag ctgaagaaac ctggcgcctc tgtgaaggtg      60
tcctgcaagg ctagcggcta cacattcacc aactacggca tcaactgggt ccgacaggct     120
cctggacagg gactcgaatg gatgggctgg atcaacccct acaccggcga gacaacatac     180
gccgaggagt tcaagggcag attcgtgttc agcctggata ccagcgtcag cacagcttac     240
ctgcagatca gcagcctgaa ggccgaggat accgccgtgt acttctgcgc cagactgtac     300
tacggcaaca gattcgactc ttggggccag ggcacactgg tcacagtctc ttct           354

<210> SEQ ID NO 166
<211> LENGTH: 118
<212> TYPE: PRT
<213> ORGANISM: Homo sapiens

<400> SEQUENCE: 166

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Asn Trp Val Arg Gln Ala Pro Gly Gln Gly Leu Glu Trp Met
        35                  40                  45

Gly Trp Ile Asn Pro Gly Thr Gly Glu Thr Thr Tyr Ala Glu Gly Phe
    50                  55                  60

Thr Gly Arg Phe Val Leu Ser Trp Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Leu Tyr Tyr Gly Asn Arg Phe Asp Ser Trp Gly Gln Gly Thr
            100                 105                 110

Leu Val Thr Val Ser Ser
        115

<210> SEQ ID NO 167
<211> LENGTH: 10
<212> TYPE: PRT
<213> ORGANISM: Homo sapiens

<400> SEQUENCE: 167

Gly Tyr Thr Phe Thr Asn Tyr Gly Ile Asn
1               5                   10

<210> SEQ ID NO 168
<211> LENGTH: 16
<212> TYPE: PRT
<213> ORGANISM: Homo sapiens

<400> SEQUENCE: 168

Trp Ile Asn Pro Gly Thr Gly Glu Thr Thr Tyr Ala Glu Gly Phe Thr
1               5                   10                  15

<210> SEQ ID NO 169
<211> LENGTH: 9
<212> TYPE: PRT
<213> ORGANISM: Homo sapiens

<400> SEQUENCE: 169

Leu Tyr Tyr Gly Asn Arg Phe Asp Ser
1               5

<210> SEQ ID NO 170
<211> LENGTH: 354
<212> TYPE: DNA
<213> ORGANISM: Homo sapiens

<400> SEQUENCE: 170
cagattcagc tggtgcagtc tggcagcgag ctgaagaaac ctggcgcctc tgtgaaggtg      60
tcctgcaagg ctagcggcta cacattcacc aactacggca tcaactgggt ccgacaggct     120
cctggacagg gactcgaatg gatgggctgg atcaacccccg gcaccggcga dacaacatac     180
gccgagggct tcacaggcag attcgtgctg agctgggata ccagcgtcag cacagcttac     240
ctgcagatca gcagcctgaa ggccgaggat accgccgtgt acttctgcgc cagactgtac     300
tacggcaaca gattcgactc ttggggccag ggcacactgg tcacagtctc ttct           354

<210> SEQ ID NO 171
<211> LENGTH: 118
<212> TYPE: PRT
<213> ORGANISM: Homo sapiens

<400> SEQUENCE: 171

Gln Val Gln Leu Val Gln Ser Gly Ala Glu Val Lys Lys Pro Gly Ser
1               5                   10                  15

Ser Val Lys Val Ser Cys Lys Pro Ser Gly Tyr Ala Phe Thr Asn Tyr
                20                  25                  30

Leu Ile Asp Trp Val Arg Gln Ala Pro Gly Gln Gly Leu Glu Trp Met
            35                  40                  45

Gly Gly Ile Asn Pro Gly Ser Gly Asp Thr Val Tyr Asn Glu Lys Phe
        50                  55                  60

Gln Gly Arg Val Thr Leu Thr Ala Asp Lys Ser Ser Met Thr Ala Tyr
65                  70                  75                  80

Met Glu Leu Ser Ser Leu Arg Ser Glu Asp Thr Ala Val Tyr Phe Cys
                85                  90                  95

Ala Arg Arg Val Arg Gly Asn Ser Phe Asp Ser Trp Gly Gln Gly Thr
            100                 105                 110

Leu Val Thr Val Ser Ser
            115

<210> SEQ ID NO 172
<211> LENGTH: 10
<212> TYPE: PRT
<213> ORGANISM: Homo sapiens

<400> SEQUENCE: 172

Gly Tyr Ala Phe Thr Asn Tyr Leu Ile Asp
1               5                   10

<210> SEQ ID NO 173
<211> LENGTH: 16
<212> TYPE: PRT
<213> ORGANISM: Homo sapiens

<400> SEQUENCE: 173

Gly Ile Asn Pro Gly Ser Gly Asp Thr Val Tyr Asn Glu Lys Phe Gln
1               5                   10                  15

<210> SEQ ID NO 174
<211> LENGTH: 9
<212> TYPE: PRT
<213> ORGANISM: Homo sapiens

<400> SEQUENCE: 174

Arg Val Arg Gly Asn Ser Phe Asp Ser
1               5

<210> SEQ ID NO 175
<211> LENGTH: 354
<212> TYPE: DNA
<213> ORGANISM: Homo sapiens

<400> SEQUENCE: 175
caggttcagc tggttcagtc tggcgccgaa gtgaagaaac ctggcagcag cgtgaaggtg      60
tcctgcaagc cttctggcta cgccttcacc aactacctga tcgactgggt ccgacaggct     120
cctggacagg gacttgaatg gatgggcggc atcaaccctg gcagcggcga tacagtgtac     180
aacgagaagt tccagggcag agtgaccctg accgccgaca gtctagcat gaccgcctac     240 atggaactga gcagcctgag aagcgaggat accgccgtgt acttctgtgc cagaagagtg     300
cggggcaaca gcttcgattc ttggggccag ggaaccctgg tcaccgtttc ttct           354

<210> SEQ ID NO 176
<211> LENGTH: 118
<212> TYPE: PRT
<213> ORGANISM: Homo sapiens

<400> SEQUENCE: 176

Gln Val Gln Leu Val Gln Ser Gly Ala Glu Val Lys Lys Pro Gly Ser
1               5                   10                  15

Ser Val Lys Val Ser Cys Lys Pro Ser Gly Tyr Thr Phe Thr Asn Tyr
            20                  25                  30

Leu Ile Asp Trp Val Arg Gln Ala Pro Gly Gln Gly Leu Glu Trp Met
        35                  40                  45

Gly Gly Ile Asn Pro Gly Ser Gly Asp Thr Val Tyr Asn Glu Lys Phe
    50                  55                  60

Gln Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

```
Ala Arg Arg Val Arg Gly Asn Ser Phe Asp Ser Trp Gly Gln Gly Thr
            100                 105                 110

Leu Val Thr Val Ser Ser
        115

<210> SEQ ID NO 177
<211> LENGTH: 10
<212> TYPE: PRT
<213> ORGANISM: Homo sapiens

<400> SEQUENCE: 177

Gly Tyr Thr Phe Thr Asn Tyr Leu Ile Asp
1               5                   10

<210> SEQ ID NO 178
<211> LENGTH: 16
<212> TYPE: PRT
<213> ORGANISM: Homo sapiens

<400> SEQUENCE: 178

Gly Ile Asn Pro Gly Ser Gly Asp Thr Val Tyr Asn Glu Lys Phe Gln
1               5                   10                  15

<210> SEQ ID NO 179
<211> LENGTH: 9
<212> TYPE: PRT
<213> ORGANISM: Homo sapiens

<400> SEQUENCE: 179

Arg Val Arg Gly Asn Ser Phe Asp Ser
1               5

<210> SEQ ID NO 180
<211> LENGTH: 354
<212> TYPE: DNA
<213> ORGANISM: Homo sapiens

<400> SEQUENCE: 180
caggttcagc tggttcagtc tggcgccgaa gtgaagaaac ctggcagcag cgtgaaggtg      60
tcctgcaagc cttctggcta caccttcacc aactacctga tcgactgggt ccgacaggct     120
cctggacagg gacttgaatg gatgggcggc atcaaccctg gcagcggcga tacagtgtac     180
aacgagaagt tccagggcag agtgaccctg accgccgacg agtctaccag caccgcctac     240
atggaactga gcagcctgag aagcgaggat accgccgtgt acttctgtgc cagaagagtg     300
cggggcaaca gcttcgattc ttggggccag ggaaccctgg tcaccgtttc ttct           354

<210> SEQ ID NO 181
<211> LENGTH: 118
<212> TYPE: PRT
<213> ORGANISM: Homo sapiens

<400> SEQUENCE: 181

Gln Val Gln Leu Val Gln Ser Gly Ala Glu Val Lys Lys Pro Gly Ser
1               5                   10                  15

Ser Val Lys Val Ser Cys Lys Pro Ser Gly Tyr Thr Phe Thr Asn Tyr
            20                  25                  30

Leu Ile Asp Trp Val Arg Gln Ala Pro Gly Gln Gly Leu Glu Trp Met
        35                  40                  45

Gly Gly Ile Asn Pro Gly Ser Gly Asp Thr Val Tyr Asn Glu Lys Phe
    50                  55                  60
```

-continued

```
Gln Gly Arg Val Thr Leu Thr Ala Asp Lys Ser Ser Met Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Val Arg Gly Asn Ser Phe Asp Ser Trp Gly Gln Gly Thr
            100                 105                 110

Leu Val Thr Val Ser Ser
        115

<210> SEQ ID NO 182
<211> LENGTH: 10
<212> TYPE: PRT
<213> ORGANISM: Homo sapiens

<400> SEQUENCE: 182

Gly Tyr Thr Phe Thr Asn Tyr Leu Ile Asp
1               5                   10

<210> SEQ ID NO 183
<211> LENGTH: 16
<212> TYPE: PRT
<213> ORGANISM: Homo sapiens

<400> SEQUENCE: 183

Gly Ile Asn Pro Gly Ser Gly Asp Thr Val Tyr Asn Glu Lys Phe Gln
1               5                   10                  15

<210> SEQ ID NO 184
<211> LENGTH: 9
<212> TYPE: PRT
<213> ORGANISM: Homo sapiens

<400> SEQUENCE: 184

Arg Val Arg Gly Asn Ser Phe Asp Ser
1               5

<210> SEQ ID NO 185
<211> LENGTH: 354
<212> TYPE: DNA
<213> ORGANISM: Homo sapiens

<400> SEQUENCE: 185
caggttcagc tggttcagtc tggcgccgaa gtgaagaaac ctggcagcag cgtgaaggtg      60
tcctgcaagc cttctggcta caccttcacc aactacctga tcgactgggt ccgacaggct     120
cctggacagg gacttgaatg gatgggcggc atcaaccctg gcagcggcga tacagtgtac     180
aacgagaagt tccagggcag agtgaccctg accgccgaca gtctagcat gaccgcctac     240 atggaactga gcagcctgag aagcgaggat accgccgtgt actactgtgc cagaagagtg     300
cggggcaaca gcttcgattc ttggggccag ggaaccctgg tcaccgtttc ttct           354

<210> SEQ ID NO 186
<211> LENGTH: 118
<212> TYPE: PRT
<213> ORGANISM: Homo sapiens

<400> SEQUENCE: 186

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30
```

-continued

Leu Ile Asp Trp Val Arg Gln Ala Pro Gly Gln Gly Leu Glu Trp Met
    35                  40              45

Gly Gly Ile Asn Pro Gly Ser Gly Asp Thr Val Tyr Asn Glu Lys Phe
    50                  55              60

Gln Gly Arg Val Thr Leu Thr Ala Asp Lys Ser Ser Met Thr Ala Tyr
65                  70              75                  80

Met Glu Leu Ser Ser Leu Arg Ser Glu Asp Thr Ala Val Tyr Phe Cys
                85                  90                  95

Ala Arg Arg Val Arg Gly Asn Ser Phe Asp Ser Trp Gly Gln Gly Thr
            100                 105             110

Leu Val Thr Val Ser Ser
        115

<210> SEQ ID NO 187
<211> LENGTH: 10
<212> TYPE: PRT
<213> ORGANISM: Homo sapiens

<400> SEQUENCE: 187

Gly Tyr Thr Phe Thr Asn Tyr Leu Ile Asp
1               5               10

<210> SEQ ID NO 188
<211> LENGTH: 16
<212> TYPE: PRT
<213> ORGANISM: Homo sapiens

<400> SEQUENCE: 188

Gly Ile Asn Pro Gly Ser Gly Asp Thr Val Tyr Asn Glu Lys Phe Gln
1               5               10                  15

<210> SEQ ID NO 189
<211> LENGTH: 9
<212> TYPE: PRT
<213> ORGANISM: Homo sapiens

<400> SEQUENCE: 189

Arg Val Arg Gly Asn Ser Phe Asp Ser
1               5

<210> SEQ ID NO 190
<211> LENGTH: 354
<212> TYPE: DNA
<213> ORGANISM: Homo sapiens

<400> SEQUENCE: 190
caggttcagc tggttcagtc tggcgccgaa gtgaagaaac ctggcagcag cgtgaaggtg      60
tcctgcaagg cttctggcta caccttcacc aactacctga tcgactgggt ccgacaggct     120
cctggacagg gacttgaatg gatgggcggc atcaaccctg gcagcggcga tacagtgtac     180
aacgagaagt tccagggcag agtgaccctg accgccgaca gtctagcat gaccgcctac      240 atggaactga gcagcctgag aagcgaggat accgccgtgt acttctgtgc cagaagagtg     300
cggggcaaca gcttcgattc ttggggccag ggaaccctgg tcaccgtttc ttct          354

<210> SEQ ID NO 191
<211> LENGTH: 118
<212> TYPE: PRT
<213> ORGANISM: Homo sapiens

<400> SEQUENCE: 191

```
Gln Val Gln Leu Val Gln Ser Gly Ala Glu Val Lys Lys Pro Gly Ser
1               5                   10                  15

Ser Val Lys Val Ser Cys Lys Pro Ser Gly Tyr Thr Phe Thr Asn Tyr
            20                  25                  30

Leu Ile Asp Trp Val Arg Gln Ala Pro Gly Gln Gly Leu Glu Trp Met
        35                  40                  45

Gly Gly Ile Asn Pro Gly Ser Gly Asp Thr Val Tyr Asn Glu Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Arg Val Arg Gly Asn Ser Phe Asp Ser Trp Gly Gln Gly Thr
            100                 105                 110

Leu Val Thr Val Ser Ser
        115

<210> SEQ ID NO 192
<211> LENGTH: 10
<212> TYPE: PRT
<213> ORGANISM: Homo sapiens

<400> SEQUENCE: 192

Gly Tyr Thr Phe Thr Asn Tyr Leu Ile Asp
1               5                   10

<210> SEQ ID NO 193
<211> LENGTH: 16
<212> TYPE: PRT
<213> ORGANISM: Homo sapiens

<400> SEQUENCE: 193

Gly Ile Asn Pro Gly Ser Gly Asp Thr Val Tyr Asn Glu Lys Phe Gln
1               5                   10                  15

<210> SEQ ID NO 194
<211> LENGTH: 9
<212> TYPE: PRT
<213> ORGANISM: Homo sapiens

<400> SEQUENCE: 194

Arg Val Arg Gly Asn Ser Phe Asp Ser
1               5

<210> SEQ ID NO 195
<211> LENGTH: 354
<212> TYPE: DNA
<213> ORGANISM: Homo sapiens

<400> SEQUENCE: 195
caggttcagc tggttcagtc tggcgccgaa gtgaagaaac ctggcagcag cgtgaaggtg      60
tcctgcaagc cttctggcta caccttcacc aactacctga tcgactgggt ccgacaggct     120
cctggacagg gacttgaatg gatgggcggc atcaaccctg gcagcggcga tacagtgtac     180
aacgagaagt tccagggcag agtgaccatc accgccgacg agtctaccag caccgcctac     240
atggaactga gcagcctgag aagcgaggat accgccgtgt acttctgtgc cagaagagtg     300
cggggcaaca gcttcgattc ttggggccag ggaaccctgg tcaccgtttc ttct          354
```

```
<210> SEQ ID NO 196
<211> LENGTH: 118
<212> TYPE: PRT
<213> ORGANISM: Homo sapiens

<400> SEQUENCE: 196

Gln Val Gln Leu Val Gln Ser Gly Ala Glu Val Lys Lys Pro Gly Ala
1               5                   10                  15

Ser Val Lys Val Ser Cys Lys Pro Ser Gly Tyr Ala Phe Thr Asn Tyr
            20                  25                  30

Leu Ile Asp Trp Val Arg Gln Ala Pro Gly Gln Gly Leu Glu Trp Met
        35                  40                  45

Gly Gly Ile Asn Pro Gly Ser Gly Asp Thr Val Tyr Asn Glu Lys Phe
    50                  55                  60

Gln Gly Arg Val Thr Leu Thr Ala Asp Lys Ser Ser Ser Thr Ala Tyr
65                  70                  75                  80

Met Glu Leu Ser Ser Leu Arg Ser Glu Asp Thr Ala Val Tyr Phe Cys
            85                  90                  95

Ala Arg Arg Val Arg Gly Asn Ser Phe Asp Ser Trp Gly Gln Gly Thr
            100                 105                 110

Leu Val Thr Val Ser Ser
        115

<210> SEQ ID NO 197
<211> LENGTH: 10
<212> TYPE: PRT
<213> ORGANISM: Homo sapiens

<400> SEQUENCE: 197

Gly Tyr Ala Phe Thr Asn Tyr Leu Ile Asp
1               5                   10

<210> SEQ ID NO 198
<211> LENGTH: 16
<212> TYPE: PRT
<213> ORGANISM: Homo sapiens

<400> SEQUENCE: 198

Gly Ile Asn Pro Gly Ser Gly Asp Thr Val Tyr Asn Glu Lys Phe Gln
1               5                   10                  15

<210> SEQ ID NO 199
<211> LENGTH: 9
<212> TYPE: PRT
<213> ORGANISM: Homo sapiens

<400> SEQUENCE: 199

Arg Val Arg Gly Asn Ser Phe Asp Ser
1               5

<210> SEQ ID NO 200
<211> LENGTH: 354
<212> TYPE: DNA
<213> ORGANISM: Homo sapiens

<400> SEQUENCE: 200
caggttcagc tggttcagtc tggcgccgaa gtgaagaaac ctggcgccag cgtgaaggtg      60
tcctgcaagc cttctggcta cgccttcacc aactacctga tcgactgggt ccgacaggct     120
cctggacagg gacttgaatg gatgggcggc atcaaccctg gcagcggcga tacagtgtac     180
aacgagaagt tccagggcag agtgaccctg accgccgaca gtctagcag caccgcctac     240
```

```
atggaactga gcagcctgag aagcgaggat accgccgtgt acttctgtgc cagaagagtg        300 cgggggcaaca gcttcgattc ttggggccag ggaaccctgg tcaccgtttc ttct             354
```

<210> SEQ ID NO 201
<211> LENGTH: 118
<212> TYPE: PRT
<213> ORGANISM: Homo sapiens

<400> SEQUENCE: 201

```
Gln Val Gln Leu Val Gln Ser Gly Ala Glu Val Lys Lys Pro Gly Ala
1               5                   10                  15

Ser Val Lys Val Ser Cys Lys Pro Ser Gly Tyr Thr Phe Thr Asn Tyr
            20                  25                  30

Leu Ile Asp Trp Val Arg Gln Ala Pro Gly Gln Gly Leu Glu Trp Met
        35                  40                  45

Gly Gly Ile Asn Pro Gly Ser Gly Asp Thr Val Tyr Asn Glu Lys Phe
    50                  55                  60

Gln Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Arg Arg Val Arg Gly Asn Ser Phe Asp Ser Trp Gly Gln Gly Thr
            100                 105                 110

Leu Val Thr Val Ser Ser
        115
```

<210> SEQ ID NO 202
<211> LENGTH: 10
<212> TYPE: PRT
<213> ORGANISM: Homo sapiens

<400> SEQUENCE: 202

```
Gly Tyr Thr Phe Thr Asn Tyr Leu Ile Asp
1               5                   10
```

<210> SEQ ID NO 203
<211> LENGTH: 16
<212> TYPE: PRT
<213> ORGANISM: Homo sapiens

<400> SEQUENCE: 203

```
Gly Ile Asn Pro Gly Ser Gly Asp Thr Val Tyr Asn Glu Lys Phe Gln
1               5                   10                  15
```

<210> SEQ ID NO 204
<211> LENGTH: 9
<212> TYPE: PRT
<213> ORGANISM: Homo sapiens

<400> SEQUENCE: 204

```
Arg Val Arg Gly Asn Ser Phe Asp Ser
1               5
```

<210> SEQ ID NO 205
<211> LENGTH: 354
<212> TYPE: DNA
<213> ORGANISM: Homo sapiens

<400> SEQUENCE: 205

```
caggttcagc tggttcagtc tggcgccgaa gtgaagaaac ctggcgccag cgtgaaggtg        60
```

```
tcctgcaagc cttctggcta caccttcacc aactacctga tcgactgggt ccgacaggct    120
cctggacagg gacttgaatg gatgggcggc atcaaccctg gcagcggcga tacagtgtac    180
aacgagaagt tccagggcag agtgaccctg accgccgaca cctctaccag caccgtctac    240
atggaactga gcagcctgag aagcgaggat accgccgtgt acttctgtgc cagaagagtg    300
cggggcaaca gcttcgattc ttggggccag ggaaccctgg tcaccgtttc ttct          354
```

```
<210> SEQ ID NO 206
<211> LENGTH: 118
<212> TYPE: PRT
<213> ORGANISM: Homo sapiens

<400> SEQUENCE: 206

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asn
            20                  25                  30

Tyr Ala Trp Asn Trp Ile Arg Gln Pro Pro Gly Lys Gly Leu Glu Trp
        35                  40                  45

Ile Gly Tyr Ile Asn Tyr Ser Gly Asn Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Ser Tyr Tyr Gly Asn Ser Phe Ile Tyr Trp Gly Gln Gly Thr
            100                 105                 110

Leu Val Thr Val Ser Ser
        115
```

```
<210> SEQ ID NO 207
<211> LENGTH: 11
<212> TYPE: PRT
<213> ORGANISM: Homo sapiens

<400> SEQUENCE: 207

Gly Tyr Ser Ile Thr Ser Asn Tyr Ala Trp Asn
1               5                   10
```

```
<210> SEQ ID NO 208
<211> LENGTH: 16
<212> TYPE: PRT
<213> ORGANISM: Homo sapiens

<400> SEQUENCE: 208

Tyr Ile Asn Tyr Ser Gly Asn Thr Asn Tyr Asn Pro Ser Leu Lys Ser
1               5                   10                  15
```

```
<210> SEQ ID NO 209
<211> LENGTH: 9
<212> TYPE: PRT
<213> ORGANISM: Homo sapiens

<400> SEQUENCE: 209

Ser Tyr Tyr Gly Asn Ser Phe Ile Tyr
1               5
```

```
<210> SEQ ID NO 210
<211> LENGTH: 354
```

-continued

```
<212> TYPE: DNA
<213> ORGANISM: Homo sapiens

<400> SEQUENCE: 210
caggttcagc tgcaagagtc tggacctggc ctggtcaagc ctagcgagac actgagcctg        60
acctgtaccg tgtccggcta cagcatcacc agcaactacg cctggaactg gatcagacag       120
cctcctggca aaggcctcga gtggatcggc tacatcaact acagcggcaa caccaactac       180
aaccccagcc tgaagtccag agtgaccatc agcagagaca ccagcaagaa ccagttctcc       240
ctgaagctga gcagcgtgac agccgccgat acagccgtgt actactgtgc cacaagctac       300
tacggcaaca gcttcatcta ctggggccag ggcacactgg tcaccgtttc ttct            354
```

```
<210> SEQ ID NO 211
<211> LENGTH: 118
<212> TYPE: PRT
<213> ORGANISM: Homo sapiens

<400> SEQUENCE: 211

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asn
            20                  25                  30

Tyr Ala Trp Asn Trp Ile Arg Gln Pro Pro Gly Lys Gly Leu Glu Trp
        35                  40                  45

Met Gly Tyr Ile Asn Tyr Ser Gly Asn Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Ser Tyr Tyr Gly Asn Ser Phe Ile Tyr Trp Gly Gln Gly Thr
            100                 105                 110

Leu Val Thr Val Ser Ser
        115
```

```
<210> SEQ ID NO 212
<211> LENGTH: 11
<212> TYPE: PRT
<213> ORGANISM: Homo sapiens

<400> SEQUENCE: 212

Gly Gly Ser Ile Ser Ser Asn Tyr Ala Trp Asn
1               5                   10
```

```
<210> SEQ ID NO 213
<211> LENGTH: 16
<212> TYPE: PRT
<213> ORGANISM: Homo sapiens

<400> SEQUENCE: 213

Tyr Ile Asn Tyr Ser Gly Asn Thr Asn Tyr Asn Pro Ser Leu Lys Ser
1               5                   10                  15
```

```
<210> SEQ ID NO 214
<211> LENGTH: 9
<212> TYPE: PRT
<213> ORGANISM: Homo sapiens

<400> SEQUENCE: 214
```

-continued

Ser Tyr Tyr Gly Asn Ser Phe Ile Tyr
1               5

<210> SEQ ID NO 215
<211> LENGTH: 354
<212> TYPE: DNA
<213> ORGANISM: Homo sapiens

<400> SEQUENCE: 215
caggttcagc tgcaagagtc tggacctggc ctggtcaagc ctagcgagac actgagcctg      60
acctgtaccg tgtccggcgg cagcatcagc agcaactacg cctggaactg gatcagacag     120
cctcctggca aaggcctcga gtggatgggc tacatcaact acagcggcaa caccaactac     180
aaccccagcc tgaagtccag aatcaccatc agcagagaca ccagcaagaa ccagttctcc     240
ctgaagctga gcagcgtgac agccgccgat acagccgtgt actactgtgc cacaagctac     300
tacggcaaca gcttcatcta ctggggccag ggcacactgg tcaccgtttc ttct           354

<210> SEQ ID NO 216
<211> LENGTH: 118
<212> TYPE: PRT
<213> ORGANISM: Homo sapiens

<400> SEQUENCE: 216

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asn
            20                  25                  30

Tyr Ala Trp Asn Trp Ile Arg Gln Pro Pro Gly Lys Gly Leu Glu Trp
        35                  40                  45

Ile Gly Tyr Ile Asn Tyr Ser Gly Asn Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Ser Tyr Tyr Gly Asn Ser Phe Ile Tyr Trp Gly Gln Gly Thr
            100                 105                 110

Leu Val Thr Val Ser Ser
        115

<210> SEQ ID NO 217
<211> LENGTH: 11
<212> TYPE: PRT
<213> ORGANISM: Homo sapiens

<400> SEQUENCE: 217

Gly Gly Ser Ile Ser Ser Asn Tyr Ala Trp Asn
1               5                   10

<210> SEQ ID NO 218
<211> LENGTH: 16
<212> TYPE: PRT
<213> ORGANISM: Homo sapiens

<400> SEQUENCE: 218

Tyr Ile Asn Tyr Ser Gly Asn Thr Asn Tyr Asn Pro Ser Leu Lys Ser
1               5                   10                  15

<210> SEQ ID NO 219

-continued

```
<211> LENGTH: 9
<212> TYPE: PRT
<213> ORGANISM: Homo sapiens

<400> SEQUENCE: 219

Ser Tyr Tyr Gly Asn Ser Phe Ile Tyr
1               5

<210> SEQ ID NO 220
<211> LENGTH: 354
<212> TYPE: DNA
<213> ORGANISM: Homo sapiens

<400> SEQUENCE: 220
caggttcagc tgcaagagtc tggacctggc ctggtcaagc ctagcgagac actgagcctg        60
acctgtaccg tgtccggcgg cagcatcagc agcaactacg cctggaactg gatcagacag       120
cctcctggca aaggcctcga gtggatcggc tacatcaact acagcggcaa caccaactac       180
aaccccagcc tgaagtccag agtgaccatc agcagagaca ccagcaagaa ccagttctcc       240
ctgaagctga gcagcgtgac agccgccgat acagccgtgt actactgtgc cacaagctac       300
tacggcaaca gcttcatcta ctggggccag ggcacactgg tcaccgtttc ttct            354

<210> SEQ ID NO 221
<211> LENGTH: 118
<212> TYPE: PRT
<213> ORGANISM: Homo sapiens

<400> SEQUENCE: 221

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asn
            20                  25                  30

Tyr Ala Trp Asn Trp Ile Arg Gln Pro Pro Gly Lys Gly Leu Glu Trp
        35                  40                  45

Ile Gly Tyr Ile Asn Tyr Ser Gly Tyr Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Ser Tyr Tyr Gly Asn Ser Phe Ile Tyr Trp Gly Gln Gly Thr
                100                 105                 110

Leu Val Thr Val Ser Ser
        115

<210> SEQ ID NO 222
<211> LENGTH: 11
<212> TYPE: PRT
<213> ORGANISM: Homo sapiens

<400> SEQUENCE: 222

Gly Gly Ser Ile Ser Ser Asn Tyr Ala Trp Asn
1               5                   10

<210> SEQ ID NO 223
<211> LENGTH: 16
<212> TYPE: PRT
<213> ORGANISM: Homo sapiens

<400> SEQUENCE: 223
```

-continued

```
Tyr Ile Asn Tyr Ser Gly Tyr Thr Asn Tyr Asn Pro Ser Leu Lys Ser
1               5                   10                  15
```

<210> SEQ ID NO 224
<211> LENGTH: 9
<212> TYPE: PRT
<213> ORGANISM: Homo sapiens

<400> SEQUENCE: 224

```
Ser Tyr Tyr Gly Asn Ser Phe Ile Tyr
1               5
```

<210> SEQ ID NO 225
<211> LENGTH: 354
<212> TYPE: DNA
<213> ORGANISM: Homo sapiens

<400> SEQUENCE: 225

```
caggttcagc tgcaagagtc tggacctggc ctggtcaagc ctagcgagac actgagcctg      60
acctgtaccg tgtccggcgg cagcatcagc agcaactacg cctggaactg gatcagacag     120
cctcctggca aaggcctcga gtggatcggc tacatcaact acagcggcta caccaactac     180
aaccccagcc tgaagtccag agtgaccatc agcagagaca ccagcaagaa ccagttctcc     240
ctgaagctga gcagcgtgac agccgccgat acagccgtgt actactgtgc cacaagctac     300
tacggcaaca gcttcatcta ctggggccag ggcacactgg tcaccgtttc ttct            354
```

<210> SEQ ID NO 226
<211> LENGTH: 118
<212> TYPE: PRT
<213> ORGANISM: Homo sapiens

<400> SEQUENCE: 226

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asn
            20                  25                  30

Tyr Ala Trp Asn Trp Ile Arg Gln Pro Pro Gly Lys Gly Leu Glu Trp
        35                  40                  45

Ile Gly Tyr Ile Asn Tyr Ser Gly Asn Thr Ala Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Ser Tyr Tyr Gly Asn Ser Phe Ile Tyr Trp Gly Gln Gly Thr
            100                 105                 110

Leu Val Thr Val Ser Ser
        115
```

<210> SEQ ID NO 227
<211> LENGTH: 11
<212> TYPE: PRT
<213> ORGANISM: Homo sapiens

<400> SEQUENCE: 227

```
Gly Gly Ser Ile Ser Ser Asn Tyr Ala Trp Asn
1               5                   10
```

```
<210> SEQ ID NO 228
<211> LENGTH: 16
<212> TYPE: PRT
<213> ORGANISM: Homo sapiens

<400> SEQUENCE: 228

Tyr Ile Asn Tyr Ser Gly Asn Thr Ala Tyr Asn Pro Ser Leu Lys Ser
1               5                   10                  15

<210> SEQ ID NO 229
<211> LENGTH: 9
<212> TYPE: PRT
<213> ORGANISM: Homo sapiens

<400> SEQUENCE: 229

Ser Tyr Tyr Gly Asn Ser Phe Ile Tyr
1               5

<210> SEQ ID NO 230
<211> LENGTH: 354
<212> TYPE: DNA
<213> ORGANISM: Homo sapiens

<400> SEQUENCE: 230
caggttcagc tgcaagagtc tggacctggc ctggtcaagc ctagcgagac actgagcctg        60
acctgtaccg tgtccggcgg cagcatcagc agcaactacg cctggaactg gatcagacag       120
cctcctggca aaggcctcga gtggatcggc tacatcaact acagcggcaa caccgcctac       180 aacccccagcc tgaagtccag agtgaccatc agcagagaca ccagcaagaa ccagttctcc      240
ctgaagctga gcagcgtgac agccgccgat acagccgtgt actactgtgc cacaagctac       300
tacggcaaca gcttcatcta ctggggccag ggcacactgg tcaccgtttc ttct            354

<210> SEQ ID NO 231
<211> LENGTH: 118
<212> TYPE: PRT
<213> ORGANISM: Homo sapiens

<400> SEQUENCE: 231

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asn
                20                  25                  30

Tyr Ala Trp Asn Trp Ile Arg Gln Pro Pro Gly Lys Gly Leu Glu Trp
            35                  40                  45

Ile Gly Tyr Ile Tyr Tyr Ser Gly Asn Thr Asn Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Ser Tyr Tyr Gly Asn Ser Phe Ile Tyr Trp Gly Gln Gly Thr
                100                 105                 110

Leu Val Thr Val Ser Ser
            115

<210> SEQ ID NO 232
<211> LENGTH: 11
<212> TYPE: PRT
<213> ORGANISM: Homo sapiens
```

```
<400> SEQUENCE: 232

Gly Gly Ser Ile Ser Ser Asn Tyr Ala Trp Asn
1               5                   10

<210> SEQ ID NO 233
<211> LENGTH: 16
<212> TYPE: PRT
<213> ORGANISM: Homo sapiens

<400> SEQUENCE: 233

Tyr Ile Tyr Tyr Ser Gly Asn Thr Asn Tyr Asn Pro Ser Leu Lys Ser
1               5                   10                  15

<210> SEQ ID NO 234
<211> LENGTH: 9
<212> TYPE: PRT
<213> ORGANISM: Homo sapiens

<400> SEQUENCE: 234

Ser Tyr Tyr Gly Asn Ser Phe Ile Tyr
1               5

<210> SEQ ID NO 235
<211> LENGTH: 354
<212> TYPE: DNA
<213> ORGANISM: Homo sapiens

<400> SEQUENCE: 235
caggttcagc tgcaagagtc tggacctggc ctggtcaagc ctagcgagac actgagcctg      60
acctgtaccg tgtccggcgg cagcatcagc agcaactacg cctggaactg gatcagacag     120
cctcctggca aaggcctcga gtggatcggc tacatctact acagcggcaa caccaactac     180
aaccccagcc tgaagtccag agtgaccatc agcagagaca ccagcaagaa ccagttctcc     240
ctgaagctga gcagcgtgac agccgccgat acagccgtgt actactgtgc cacaagctac     300
tacggcaaca gcttcatcta ctggggccag ggcacactgg tcaccgtttc ttct           354

<210> SEQ ID NO 236
<211> LENGTH: 113
<212> TYPE: PRT
<213> ORGANISM: Homo sapiens

<400> SEQUENCE: 236

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Tyr Tyr Pro Leu Thr Phe Gly Gly Gly Thr Lys Val Glu Ile
            100                 105                 110

Lys
```

-continued

```
<210> SEQ ID NO 237
<211> LENGTH: 17
<212> TYPE: PRT
<213> ORGANISM: Homo sapiens

<400> SEQUENCE: 237

Lys Ser Ser Gln Ser Leu Leu Asn Ser Gly Asn Gln Arg Asn Tyr Leu
1               5                   10                  15

Thr

<210> SEQ ID NO 238
<211> LENGTH: 7
<212> TYPE: PRT
<213> ORGANISM: Homo sapiens

<400> SEQUENCE: 238

Trp Ala Ser Thr Arg Glu Ser
1               5

<210> SEQ ID NO 239
<211> LENGTH: 9
<212> TYPE: PRT
<213> ORGANISM: Homo sapiens

<400> SEQUENCE: 239

Gln Asn Ala Tyr Tyr Tyr Pro Leu Thr
1               5

<210> SEQ ID NO 240
<211> LENGTH: 339
<212> TYPE: DNA
<213> ORGANISM: Homo sapiens

<400> SEQUENCE: 240
gacatcgtga tgacacagag ccctgatagc ctggccgtgt ctctgggaga gagagccacc        60
atcaactgca agagcagcca gagcctgctg aacagcggca accagagaaa ctacctgacc       120
tggtatcagc agaagcccgg ccagcctcct aagctgctga tctactgggc cagcaccaga       180
gaatctggcg tgcccgatag attcagcggc agcggctctg gaaccgactt caccctgaca       240
atcagctccc tgcaggccga ggatgtggcc gtgtactact gtcagaacgc ctactactac       300
cctctgacct tcggcggagg caccaaggtg gaaatcaag                              339

<210> SEQ ID NO 241
<211> LENGTH: 113
<212> TYPE: PRT
<213> ORGANISM: Homo sapiens

<400> SEQUENCE: 241

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Arg Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

Ala Tyr Tyr Tyr Pro Leu Thr Phe Gly Gly Gly Thr Lys Val Glu Ile
            100                 105                 110

Lys

<210> SEQ ID NO 242
<211> LENGTH: 17
<212> TYPE: PRT
<213> ORGANISM: Homo sapiens

<400> SEQUENCE: 242

Lys Ser Ser Gln Ser Leu Leu Asn Ser Gly Asn Gln Arg Asn Tyr Leu
1               5                   10                  15

Ala

<210> SEQ ID NO 243
<211> LENGTH: 7
<212> TYPE: PRT
<213> ORGANISM: Homo sapiens

<400> SEQUENCE: 243

Trp Ala Ser Thr Arg Glu Ser
1               5

<210> SEQ ID NO 244
<211> LENGTH: 9
<212> TYPE: PRT
<213> ORGANISM: Homo sapiens

<400> SEQUENCE: 244

Gln Gln Ala Tyr Tyr Tyr Pro Leu Thr
1               5

<210> SEQ ID NO 245
<211> LENGTH: 339
<212> TYPE: DNA
<213> ORGANISM: Homo sapiens

<400> SEQUENCE: 245
gacatcgtga tgacacagag ccctgatagc ctggccgtgt ctctgggaga gagagccacc       60
atcaactgca agagcagcca gagcctgctg aacagcggca accagagaaa ctacctggcc      120
tggtatcagc agaagcccgg ccagcctcct aagctgctga tctactgggc cagcaccaga      180
gaatctggcg tgcccgatag attcagcggc agcggctctg gaaccgactt caccctgaca      240
atcagctccc tgcaggccga ggatgtggcc gtgtactact gtcagcaggc ctactactac      300
cctctgacct tcggcggagg caccaaggtg gaaatcaag                              339

<210> SEQ ID NO 246
<211> LENGTH: 113
<212> TYPE: PRT
<213> ORGANISM: Homo sapiens

<400> SEQUENCE: 246

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Gly Asn Gln Arg Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val

-continued

```
          50                    55                    60

Pro Asp Arg Phe Ser Gly Ser Gly Ser Gly Thr Asp Phe Thr Leu Thr
65                  70                    75                  80

Ile Ser Ser Leu Gln Ala Glu Asp Val Ala Val Tyr Tyr Cys Gln Gln
                85                    90                    95

Ala Tyr Tyr Tyr Pro Leu Thr Phe Gly Gly Gly Thr Lys Val Glu Ile
            100                   105                   110

Lys
```

<210> SEQ ID NO 247
<211> LENGTH: 17
<212> TYPE: PRT
<213> ORGANISM: Homo sapiens

<400> SEQUENCE: 247

```
Lys Ser Ser Gln Ser Leu Leu Tyr Ser Gly Asn Gln Arg Asn Tyr Leu
1                   5                     10                    15

Ala
```

<210> SEQ ID NO 248
<211> LENGTH: 7
<212> TYPE: PRT
<213> ORGANISM: Homo sapiens

<400> SEQUENCE: 248

```
Trp Ala Ser Thr Arg Glu Ser
1                   5
```

<210> SEQ ID NO 249
<211> LENGTH: 9
<212> TYPE: PRT
<213> ORGANISM: Homo sapiens

<400> SEQUENCE: 249

```
Gln Gln Ala Tyr Tyr Tyr Pro Leu Thr
1                   5
```

<210> SEQ ID NO 250
<211> LENGTH: 339
<212> TYPE: DNA
<213> ORGANISM: Homo sapiens

<400> SEQUENCE: 250

```
gacatcgtga tgacacagag ccctgatagc ctggccgtgt ctctgggaga gagagccacc     60
atcaactgca agagcagcca gagcctgctg tacagcggca accagagaaa ctacctggcc    120
tggtatcagc agaagcccgg ccagcctcct aagctgctga tctactgggc cagcaccaga    180
gaatctggcg tgcccgatag attcagcggc agcggctctg gaaccgactt caccctgaca    240
atcagctccc tgcaggccga ggatgtggcc gtgtactact gtcagcaggc ctactactac    300
cctctgacct tcggcggagg caccaaggtg gaaatcaag                           339
```

<210> SEQ ID NO 251
<211> LENGTH: 113
<212> TYPE: PRT
<213> ORGANISM: Homo sapiens

<400> SEQUENCE: 251

```
Asp Ile Val Met Thr Gln Ser Pro Asp Ser Leu Ala Val Ser Leu Gly
1                   5                     10                    15
```

Glu Arg Ala Thr Ile Asn Cys Lys Ser Ser Gln Ser Leu Leu Asn Ser
                20                      25                      30

Gly Asn Gln Lys Asn Tyr Leu Thr Trp Tyr Gln Gln Lys Pro Gly Gln
        35                      40                      45

Pro Pro Lys Leu Leu Ile Tyr Trp Ala Ser Thr Arg Glu Ser Gly Val
    50                      55                      60

Pro Asp Arg Phe Ser Gly Ser Gly Ser Gly Lys Asp Phe Thr Leu Thr
65                      70                      75                      80

Ile Ser Ser Leu Gln Ala Glu Asp Val Ala Val Tyr Tyr Cys Gln Asn
                85                      90                      95

Asn Tyr Phe Tyr Pro Leu Thr Phe Gly Gly Gly Thr Lys Val Glu Ile
            100                     105                     110

Lys

<210> SEQ ID NO 252
<211> LENGTH: 17
<212> TYPE: PRT
<213> ORGANISM: Homo sapiens

<400> SEQUENCE: 252

Lys Ser Ser Gln Ser Leu Leu Asn Ser Gly Asn Gln Lys Asn Tyr Leu
1               5                       10                      15

Thr

<210> SEQ ID NO 253
<211> LENGTH: 7
<212> TYPE: PRT
<213> ORGANISM: Homo sapiens

<400> SEQUENCE: 253

Trp Ala Ser Thr Arg Glu Ser
1               5

<210> SEQ ID NO 254
<211> LENGTH: 9
<212> TYPE: PRT
<213> ORGANISM: Homo sapiens

<400> SEQUENCE: 254

Gln Asn Asn Tyr Phe Tyr Pro Leu Thr
1               5

<210> SEQ ID NO 255
<211> LENGTH: 339
<212> TYPE: DNA
<213> ORGANISM: Homo sapiens

<400> SEQUENCE: 255
gacatcgtga tgacacagag ccctgatagc ctggccgtgt ctctgggaga gagagccacc          60
atcaactgca agagcagcca gagcctgctg aacagcggca accagaagaa ctacctgacc         120
tggtatcagc agaagcccgg ccagcctcct aagctgctga tctactgggc cagcaccaga         180
gaaagcggcg tgccagatag attcagcggc agcggctctg aaaggactt caccctgaca         240 atcagctccc tgcaggccga ggatgtggcc gtgtactact gccagaacaa ctacttctac         300
cctctgacct tcggcggagg caccaaggtg gaaatcaag                                 339

<210> SEQ ID NO 256
<211> LENGTH: 113
<212> TYPE: PRT

<213> ORGANISM: Homo sapiens

<400> SEQUENCE: 256

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Asn Tyr Phe Tyr Pro Leu Thr Phe Gly Gly Gly Thr Lys Val Glu Ile
            100                 105                 110

Lys

<210> SEQ ID NO 257
<211> LENGTH: 17
<212> TYPE: PRT
<213> ORGANISM: Homo sapiens

<400> SEQUENCE: 257

Lys Ser Ser Gln Ser Leu Leu Asn Ser Gly Asn Gln Lys Asn Tyr Leu
1               5                   10                  15

Ala

<210> SEQ ID NO 258
<211> LENGTH: 7
<212> TYPE: PRT
<213> ORGANISM: Homo sapiens

<400> SEQUENCE: 258

Trp Ala Ser Thr Arg Glu Ser
1               5

<210> SEQ ID NO 259
<211> LENGTH: 9
<212> TYPE: PRT
<213> ORGANISM: Homo sapiens

<400> SEQUENCE: 259

Gln Gln Asn Tyr Phe Tyr Pro Leu Thr
1               5

<210> SEQ ID NO 260
<211> LENGTH: 339
<212> TYPE: DNA
<213> ORGANISM: Homo sapiens

<400> SEQUENCE: 260
gacatcgtga tgacacagag ccctgatagc ctggccgtgt ctctgggaga gagagccacc      60
atcaactgca agagcagcca gagcctgctg aacagcggca accagaagaa ctacctggcc     120
tggtatcagc agaagcccgg ccagcctcct aagctgctga tctactgggc cagcaccaga     180
gaaagcggcg tgccagatag attcagcggc agcggctctg gaaccgactt caccctgaca     240
atcagctccc tgcaggccga ggatgtggcc gtgtactact gccagcagaa ctacttctac     300

-continued

```
cctctgacct tcggcggagg caccaaggtg gaaatcaag                                    339

<210> SEQ ID NO 261
<211> LENGTH: 113
<212> TYPE: PRT
<213> ORGANISM: Homo sapiens

<400> SEQUENCE: 261

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Ser Phe Pro Trp Thr Phe Gly Gln Gly Thr Lys Val Glu Ile
            100                 105                 110

Lys

<210> SEQ ID NO 262
<211> LENGTH: 17
<212> TYPE: PRT
<213> ORGANISM: Homo sapiens

<400> SEQUENCE: 262

Lys Ser Ser Gln Ser Leu Leu Asn Ser Gly Asn Gln Lys Asn Tyr Leu
1               5                   10                  15

Thr

<210> SEQ ID NO 263
<211> LENGTH: 7
<212> TYPE: PRT
<213> ORGANISM: Homo sapiens

<400> SEQUENCE: 263

Trp Ala Ser Thr Arg Glu Ser
1               5

<210> SEQ ID NO 264
<211> LENGTH: 9
<212> TYPE: PRT
<213> ORGANISM: Homo sapiens

<400> SEQUENCE: 264

Gln Asn Ala Tyr Ser Phe Pro Trp Thr
1               5

<210> SEQ ID NO 265
<211> LENGTH: 339
<212> TYPE: DNA
<213> ORGANISM: Homo sapiens

<400> SEQUENCE: 265
gacatcgtga tgacacagag ccctgatagc ctggccgtgt ctctgggaga gagagccacc    60
```

-continued

```
atcaactgca agagcagcca gagcctgctg aacagcggca accagaagaa ctacctgacc    120
tggtatcagc agaagcccgg ccagcctcct aagctgctga tctactgggc cagcaccaga    180
gaaagcggcg tgccagatag attcagcggc agcggctctg gaaccgactt caccctgaca    240
atcagctccc tgcaggccga ggatgtggcc gtgtactact gtcagaacgc ctacagcttc    300
ccctggacat tcggccaggg caccaaggtg gaaatcaag                            339
```

```
<210> SEQ ID NO 266
<211> LENGTH: 113
<212> TYPE: PRT
<213> ORGANISM: Homo sapiens

<400> SEQUENCE: 266

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ala Tyr Ser Phe Pro Trp Thr Phe Gly Gln Gly Thr Lys Val Glu Ile
            100                 105                 110

Lys
```

```
<210> SEQ ID NO 267
<211> LENGTH: 17
<212> TYPE: PRT
<213> ORGANISM: Homo sapiens

<400> SEQUENCE: 267

Lys Ser Ser Gln Ser Leu Leu Asn Ser Gly Asn Gln Lys Asn Tyr Leu
1               5                   10                  15

Ala
```

```
<210> SEQ ID NO 268
<211> LENGTH: 7
<212> TYPE: PRT
<213> ORGANISM: Homo sapiens

<400> SEQUENCE: 268

Trp Ala Ser Thr Arg Glu Ser
1               5
```

```
<210> SEQ ID NO 269
<211> LENGTH: 9
<212> TYPE: PRT
<213> ORGANISM: Homo sapiens

<400> SEQUENCE: 269

Gln Gln Ala Tyr Ser Phe Pro Trp Thr
1               5
```

```
<210> SEQ ID NO 270
<211> LENGTH: 339
```

<212> TYPE: DNA
<213> ORGANISM: Homo sapiens

<400> SEQUENCE: 270
gacatcgtga tgacacagag ccctgatagc ctggccgtgt ctctgggaga gagagccacc    60
atcaactgca agagcagcca gagcctgctg aacagcggca accagaagaa ctacctggcc    120
tggtatcagc agaagcccgg ccagcctcct aagctgctga tctactgggc cagcaccaga    180
gaaagcggcg tgccagatag attcagcggc agcggctctg gaaccgactt caccctgaca    240
atcagctccc tgcaggccga ggatgtggcc gtgtactact gtcagcaggc ctacagcttc    300
ccctggacat tcggccaggg caccaaggtg gaaatcaag                           339

<210> SEQ ID NO 271
<211> LENGTH: 37
<212> TYPE: DNA
<213> ORGANISM: Artificial Sequence
<220> FEATURE:
<223> OTHER INFORMATION: synthetical nucleic acid

<400> SEQUENCE: 271
ttggcaaaga attgctagat gtccaccacc acatgcc                              37

<210> SEQ ID NO 272
<211> LENGTH: 38
<212> TYPE: DNA
<213> ORGANISM: Artificial Sequence
<220> FEATURE:
<223> OTHER INFORMATION: synthetical nucleic acid

<400> SEQUENCE: 272
tgttcgggcc ctcctcgatt acacatagtc gtgcttgg                             38

<210> SEQ ID NO 273
<211> LENGTH: 37
<212> TYPE: DNA
<213> ORGANISM: Artificial Sequence
<220> FEATURE:
<223> OTHER INFORMATION: synthetical nucleic acid

<400> SEQUENCE: 273
ttggcaaaga attgctagat ggccgtgact gcctgtc                              37

<210> SEQ ID NO 274
<211> LENGTH: 20
<212> TYPE: DNA
<213> ORGANISM: Artificial Sequence
<220> FEATURE:
<223> OTHER INFORMATION: synthetical nucleic acid

<400> SEQUENCE: 274
tgtgcgccac catggccgtg                                                 20

<210> SEQ ID NO 275
<211> LENGTH: 20
<212> TYPE: DNA
<213> ORGANISM: Artificial Sequence
<220> FEATURE:
<223> OTHER INFORMATION: synthetical nucleic acid

<400> SEQUENCE: 275
tggaaggata agattgtacc                                                 20

<210> SEQ ID NO 276

```
<211> LENGTH: 20
<212> TYPE: DNA
<213> ORGANISM: Artificial Sequence
<220> FEATURE:
<223> OTHER INFORMATION: synthetical nucleic acid

<400> SEQUENCE: 276
tgggtgccat tggcctcctg                                              20
```

TUMOR THERAPEUTIC AGENT AND USE THEREOF

CROSS REFERENCE TO RELATED APPLICATIONS

This application is a national stage application under 35 U.S.C. § 371 of International Application No. PCT/CN2020/084991, filed internationally on Apr. 15, 2020, which claims priority to Chinese patent application No. 201910315634.9 filed Apr. 19, 2019. The contents of the above patent applications are incorporated by reference herein in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 166102000300SubSeqList.txt, date recorded: Jul. 11, 2022, size: 112,473 bytes).

TECHNICAL FIELD

The present disclosure relates to an antibody that recognizes the Claudins, and a manufacturing method and application thereof.

BACKGROUND ART

Claudin 18 is a member of the Claudins family with highly tissue specificity distribution. In normal tissues, it is mainly distributed in the epithelial and endothelial cells of stomach or lung. It participates in the formation of tight junctions between cells, limiting solutions and molecules penetrate through the intercellular space, play a key role in maintaining the integrity of the outer membrane of endothelial cells and basement membrane, and may participate in signal transmission.

Claudin 18 is a multiple transmembrane protein with 4 transmembrane regions in the molecule, in which 2 fragments form an extracellular domain (loop1 and loop2) outside the cell, and 2 transmembrane fragments form an intracellular domain inside the cell. Due to alternative splicing of RNA, there are two different membrane protein subtypes in tissues: Claudin 18.1 (Uniprot U56856) and Claudin 18.2 (Uniprot U56856-2). The difference between the two membrane protein subtypes are the transmembrane region (amino acid residues 1-27) and the first extracellular domain (loop1, amino acid residues 28-80) at the N-terminal, in which the sequence similarity of loop1 region is about 85%, makes it possible to produce the antibody specific targeted Claudin 18.2. The membrane protein subtypes of Claudin 18 are distributed differently in normal tissues. Claudin 18.1 is selectively expressed in normal lung tissues, while Claudin 18.2 is only highly specifically expressed on the surface of highly differentiated gastric mucosal cells. There are no expression of Claudin 18.2 detected in the stem cell region near the submucosa in the stomach tissue. Research have shown that in tumor tissues, Claudin 18.2 is not only expressed in 70% of primary gastric cancer and metastases thereof, but also has ectopic activation, which is expressed in many other cancers including pancreatic cancer (50%), esophageal cancer (30%), non-small cell lung cancer (25%), breast cancer, and ear, nose and throat tumors. Due to its ubiquitous expression in gastrointestinal tumors, Claudin 18 may become a new tumor marker and potential therapeutic target.

SUMMARY OF THE INVENTION

Through extensive and in-depth research, the present inventor unexpectedly obtained an antibody against Claudin 18.2 with extremely excellent affinity and specificity, and a humanized antibody obtained based on the antibody after numerous screenings. The antibody of the present disclosure can bind Claudin 18.2 with high specificity, and has high affinity, and mediates cell killing effect, so that it can be used for the diagnosis and treatment of some malignant tumors such as gastric cancer and pancreatic cancer. The present disclosure is completed on this basis.

In one aspect, the present disclosure provides antibody or antigen binding portions thereof which binds to human Claudin 18.2.

In one aspect, the present disclosure provides a nucleic acid molecule encoding the antibody or antigen binding portion thereof according to preceding aspects.

In one aspect, the present disclosure provides a vector comprising the nucleic acid of the preceding aspects.

In one aspect, the present disclosure provides a cell comprising the vector of the preceding aspects.

The antibody or antigen binding portion thereof according to any of the preceding aspects, wherein the antibody or antigen binding portion thereof is humanized.

In one aspect, the present disclosure provides a pharmaceutical composition or a kit comprising the antibody or antigen binding portion thereof or nucleic acid encoding thereof and a pharmaceutically acceptable carrier according to any of the preceding aspects.

A method for the treatment of cancer, which includes the following steps: administering to the mammals a therapeutically effective amount of the antibody or antigen binding fragment thereof or the nucleic acid molecule or the vector or the cell or the pharmaceutical composition of any of the preceding aspects.

Use of the antibody or antigen binding fragment thereof or the nucleic acid molecule or the vector or the cell or the pharmaceutical composition of any of the preceding aspects in the preparation of a drug or a kit for the treatment of cancer of mammals.

Claudin 18.2, NO. 6-L is a low-expressing stably transfected cell line of 3T3-Claudin 18.2.

Figure 4A:
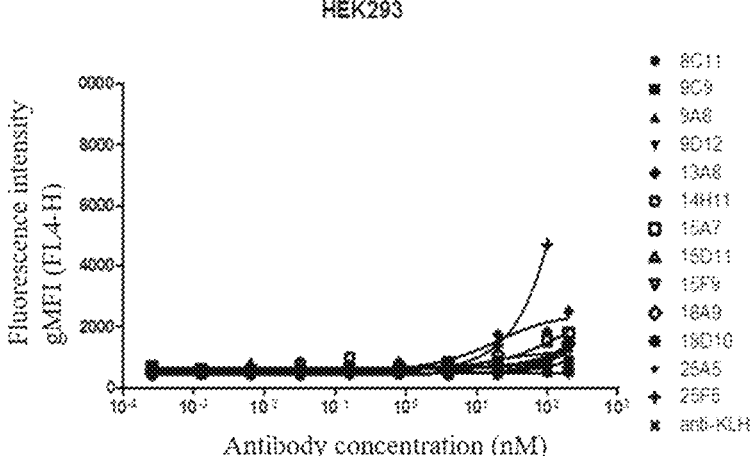
Figure 4B:
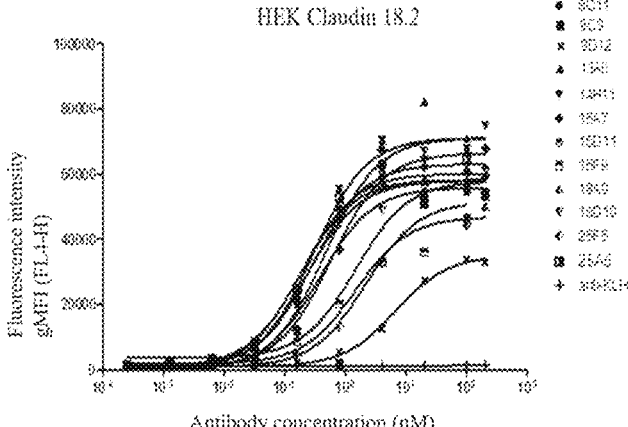
Figure 4C:
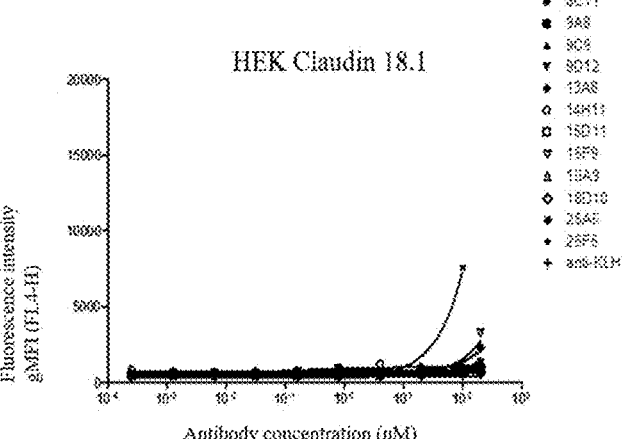

FIG. 4 shows the specific recognition of Claudin 18.2 by monoclonal antibody. FACS shows that the Claudin 18.2 IgG1 chimeric antibody obtained only recognized the HEK293-Claudin 18.2 cells transfected with Claudin 18.2 (FIG. 4B), which did not bind to HEK293 (FIG. 4A) and HEK293-Claudin 18.1 (FIG. 4C).

Figure 5:
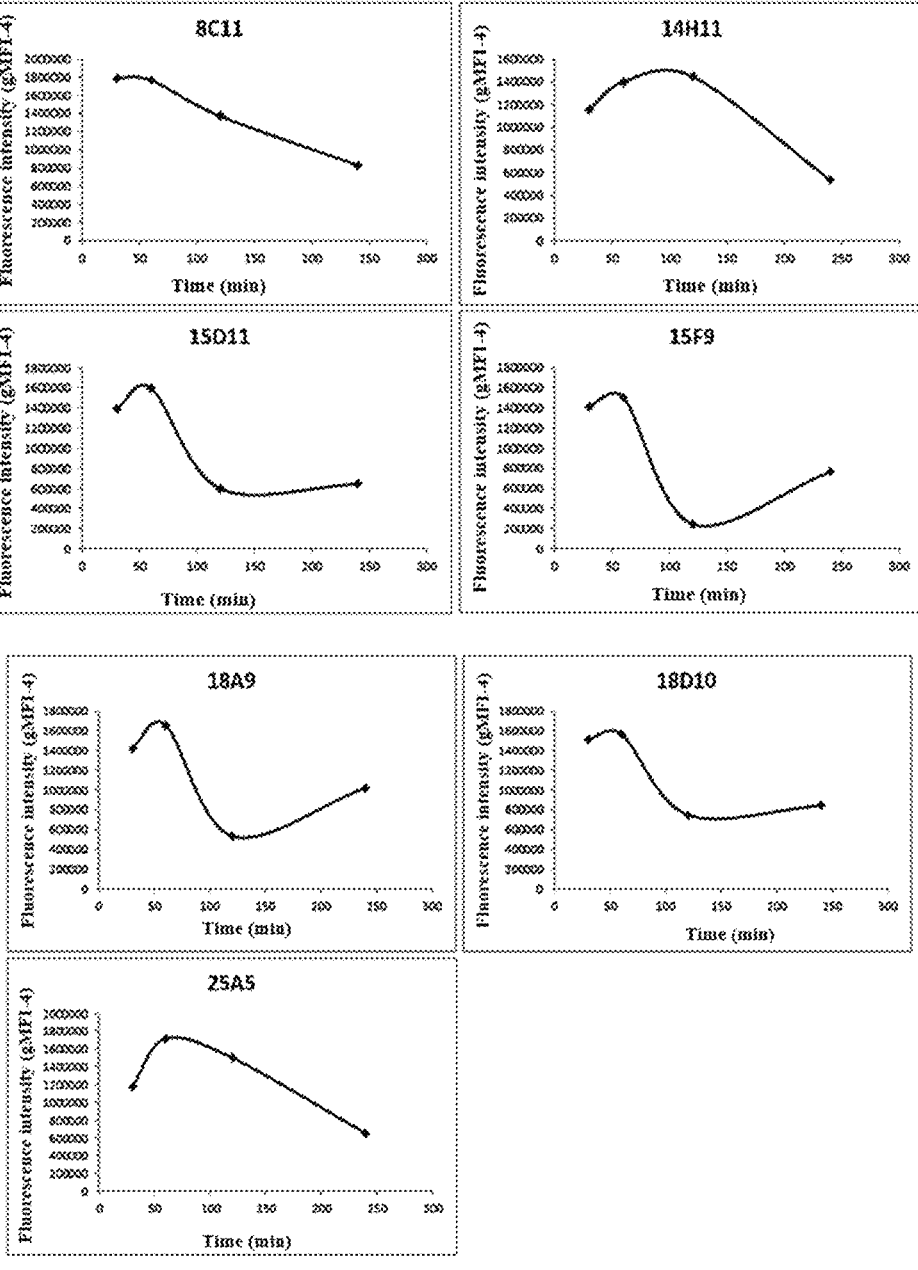

FIG. 5 shows that the amount of antibodies on the surface of cell changes with endocytosis after incubating Claudin 18.2 antibody with cells for different times at 37° C.

Figure 6:
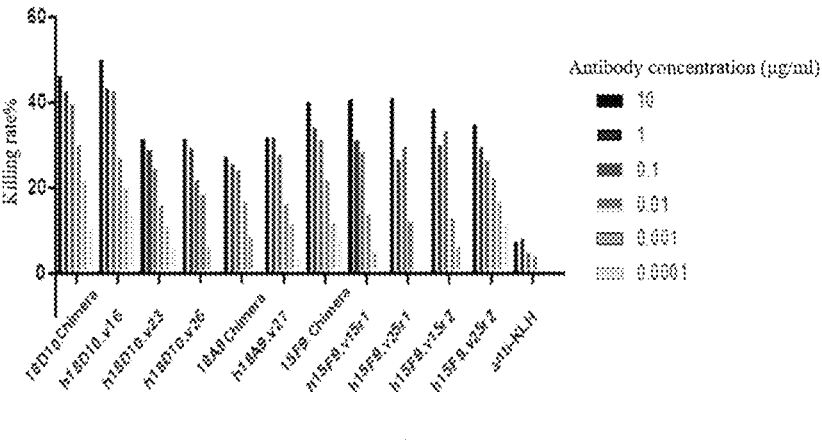

FIG. 6 shows the ADCC cell killing activity of humanized Claudin 18.2 antibody against KATO III cells.

Figure 7:
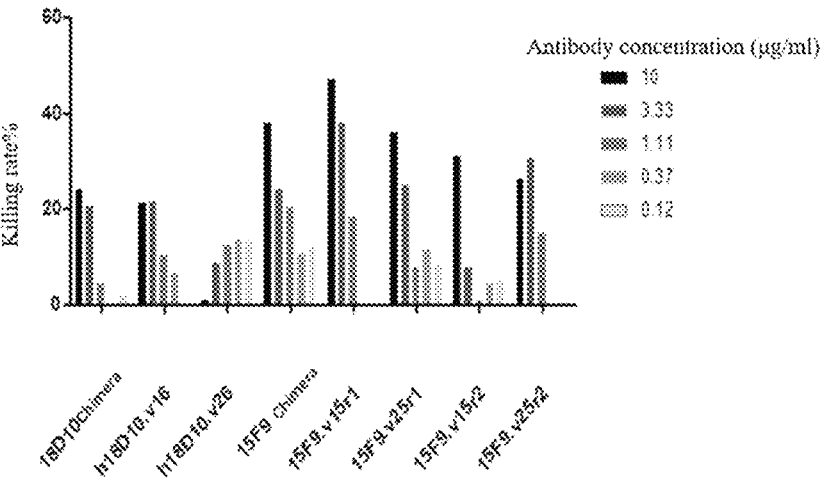

FIG. 7 shows the CDC cell killing activity of humanized Claudin 18.2 antibody against tumor cells.

Figure 8:
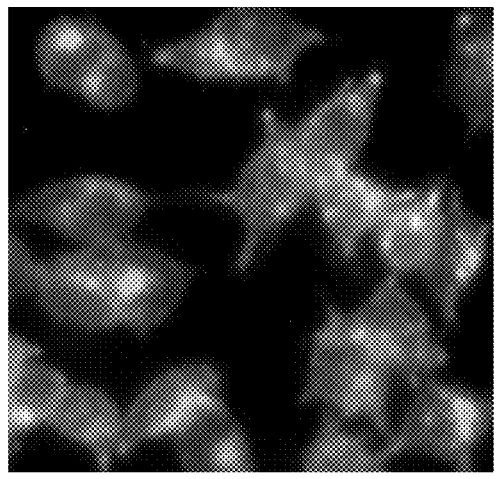

FIG. 8 shows the endocytosis of Claudin 18.2 antibody. Confocal laser showed that the humanized Claudin 18.2 antibody (red) bound the cell membrane, part of same was endocytosed and co-localized with the lysosome (green), which formed a yellow spot region indicated by the arrow (blue is the nucleus).

DETAILED DESCRIPTION OF EMBODIMENTS

I. Definitions

In the present disclosure, all scientific and technical terms used herein have the meanings commonly understood by those skilled in the art unless specified otherwise. In addition, the related terms of protein and nucleic acid chemistry, molecular biology, cell and tissue culture, microbiology, immunology, and laboratory procedures used herein are all terms and routine procedures widely used in the corresponding art. At the same time, definitions and explanations of related terms are provided below to understand the present disclosure better.

In one aspect, antibodies (e.g., monoclonal antibodies) specifically binding to Claudin 18.2 and the antigen-binding fragments thereof are provided herein. In specific aspects, a monoclonal anti-Claudin 18.2 antibody specifically binding to human Claudin 18.2 is provided herein, wherein the anti-Claudin 18.2 antibody includes variants of the parent antibody. In specific aspects, antibody specifically binding to Claudin 18.2 (e.g., human Claudin 18.2) is provided herein. In particular aspects, an anti-Claudin 18.2 antibody containing modifications in one or more amino acid residues (for example, 5-13 amino acid substitutions in the framework region of the heavy chain variable region) is provided herein, comparing with the parent antibody without said modifications, it maintains the affinity to the antigen.

As used herein, and unless otherwise specified, the term "about" or "approximately" means within plus or minus 10% of a given value or range. When an integer is required, the term refers to within plus or minus 10% of a given value or range, rounded up or down to the nearest integer.

In terms of the antibody chain polypeptide sequence, the phrase "substantially identical" may be construed as an antibody chain exhibiting at least 60%, 65%, 70%, 75%, 80%, 85%, 90%, 95%, 96%, 97%, 98%, 99% or more sequence identity to the reference polypeptide sequence. In terms of nucleic acid sequence, the term may be construed as a sequence of nucleotides exhibiting at least greater than 60%, 65%, 70%, 75%, 80%, 85%, 90%, 95%, 96%, 97%, 98%, 99% or more sequence identity to the reference nucleotide sequence.

The "identical" or "identity" with respect to a sequence has well-known meaning in the art, and the percentage of sequence identity between two nucleic acid or polypeptide molecules or regions can be calculated using the disclosed techniques. Sequence identity can be measured along the entire length of a polynucleotide or polypeptide or along a region of the molecule. Although there are many methods for measuring the identity between two polynucleotides or polypeptides, the term "identity" is well-known for the skilled person (Carrillo, H. & Lipman, D., SIAM J Applied Math 48: 1073 (1988)).

"Substitutional" variants are those that have at least one amino acid residue removed, and replaced with a different amino acid inserted in its place at the same position in a native sequence. The substitutions may be single, where only one amino acid in the molecule is substituted; or may be multiple, where two or more amino acids are substituted in the same molecule. The multiple substitutions may be at consecutive sites. Likewise, one amino acid may be substituted by multiple residues, where such a variant include both a substitution and an insertion. "Insertional" variant are those with one or more amino acids inserted immediately adjacent to an amino acid at a particular position in a native sequence. Immediately adjacent to an amino acid means linked to either the α-carboxy or α-amino functional group of the amino acid. "Deletion" variants are those with one or more amino acids in the native amino acid sequence removed. Normally, deletional variants will have one or two amino acids deleted in a particular region of the molecule.

The term "variable" in the context of a variable domain of antibodies, refers to certain portions of the pertinent molecules which have extensive sequence differences between and among antibodies and are used in the specific recognition and binding of a particular antibody for its particular target. However, the variability is not evenly distributed through the variable domains of antibodies. The variability is concentrated in three segments called complementary determining regions (CDRs; i.e., CDR1, CDR2 and CDR3) or hypervariable regions, both in the light chain and the heavy chain variable domains. The more highly conserved portions of variable domains are called the framework (FR) regions or sequences. Each variable domains of native heavy and light chains includes four FR regions, mainly adopting a β-sheet configuration, linked by three CDRs, wherein the CDRs form loops connecting, and in some cases form part of, the β-sheet structure. The CDRs in each chain are held together often in proximity by the FR regions and, with the CDRs from the other chain, contribute to the formation of target binding sites (epitopes or determinants) of antibodies. As used herein, numbering of immunoglobulin amino acid residues is performed based on the immunoglobulin amino acid residue numbering system of Kabat et al., unless otherwise indicated. A CDR can have the ability to bind specifically to the cognate epitope.

As used herein, "antibody fragments" or "antigen-binding fragments" of antibodies refer to any portion of a full-length antibody which is less than the full-length but contains at least a portion of the variable region of the antibody that binds to the antigen (e.g., one or more CDRs and/or one or more antibody binding sites), and thus retain binding specificity and at least partial specific binding ability of the full-length antibody. Therefore, antigen-binding fragments refer to antibody fragments that includes an antigen-binding portion that binds the same antigen as the antibody from which the antibody fragment are derived. Antibody fragments include antibody derivatives produced by enzymatic treatment of full-length antibodies, and derivatives produced by the synthesis, such as recombinantly-produced derivatives. Antibodies include antibody fragments. Examples of antibody fragments include, but not limited to, Fab, Fab', F(ab')2, single chain Fv (scFv), Fv, dsFv, diabodies, Fd and Fd' fragments, and other fragments, including modified fragments. The fragments may include a plurality of chains joined together, for example via a disulfide bonds and/or via a peptide linkers. Antibody fragments usually contain at least or about 50 amino acids, and typically at least or about 200 amino acids. Antigen-binding fragments include any antibody fragments, when the antibody fragments are inserted into an antibody framework (e.g., by substitution of a corresponding region), an antibody that immunospecifically binds (i.e., exhibiting at least or at least about $10^7$-$10^8$ $M^{-1}$ of Ka) antigen is obtained. "Functional fragments" or "analogs of anti-Claudin 18.2 antibodies" are fragments or analogs which prevents or substantially reduces the ability of receptors to bind to ligands or initiate signal transduction. As used herein, functional fragments generally have the same meaning as "antibody fragments", and in terms of antibodies, may refer to fragments which prevent or substantially reduce the ability of the receptors to bind to ligands or initiate signal transduction, such as $F_2$, $F_{ab}$, $F_{(ab')2}$ et al. "Fv" fragment consist of dimers (VH-VL dimer) formed by a variable domain of a heavy chain and a variable domain of a light chain by non-covalent binding. In this configuration, the three CDRs of each variable domain interact to define a target binding site on the surface of the $V_H$-$V_L$ dimer, as is the case with an intact antibody. Collectively, the six CDRs confer antigen-binding specificity to the intact antibody. However, even a single variable domain (or half of an $F_v$ that includes only 3 CDRs specific for a target) have the ability to recognize and bind targets.

As used herein, "monoclonal antibody" refers to a population of identical antibodies, meaning that each individual antibody molecule in the population of monoclonal antibody is identical to other antibody molecules. This property contrasts with the property of a polyclonal population of antibodies, which contains antibodies with a plurality of different sequences. Monoclonal antibodies can be prepared by many well-known methods (Smith et al. (2004) J. Clin. Pathol. 57, 912-917; and Nelson et al., J Clin Pathol (2000), 53, 111-117). For example, monoclonal antibodies can be prepared by immortalizing B cells, e.g., by fusion with myeloma cells to produce a hybridoma cell line or by infecting B cells with a virus such as EBV. Recombinant technology can also be used to prepare antibodies from a clonal population of host cells by transforming the host cells with a plasmid carrying an artificial sequence of a nucleotide encoding the antibodies in vitro.

As used herein, the term "hybridoma" or "hybridoma cell" refers to a cell or cell line (typically a myeloma or lymphoma cell) produced by the fusion of antibody-producing lymphocytes and non-antibody-producing cancer cells. As is known to one of ordinary skill in the art, hybridomas can proliferate and continue to supply to produce specific monoclonal antibodies. Methods for producing hybridomas are known in the art. When referring to the term "hybridoma" or "hybridoma cell" herein, it also includes subclones and progeny cells of the hybridoma.

As used herein, a full-length antibody is an antibody comprising two full-length heavy chains (for example, VH-CH1-CH2-CH3 or VH-CH1-CH2-CH3-CH4) and two full-length light chains (VL-CL) and a hinge region, such as those antibodies naturally produced by antibody secretion B cells and synthetically produced antibodies with the same domain.

The term "chimeric antibody" refers to an antibody in which the variable region sequence is derived from one species and the constant region sequence is derived from another species, such as the antibody in which the variable region sequence is derived from a mouse antibody and the constant region sequence is derived from a human antibody.

"Humanized" antibody refers to a non-human (e.g., mouse) antibody form, which is a chimeric immunoglobulin, immunoglobulin chain or a fragment thereof (such as $F_v$, $F_{ab}$, $F_{ab'}$, $F_{(ab')2}$ or other antigen-binding subsequences of antibodies), containing minimal sequences derived from non-human immunoglobulins. Preferably, the humanized antibody is a human immunoglobulin (recipient antibody), wherein residues of the complementarity determining region (CDR) of the recipient antibody are replaced by residues of the CDR of a non-human species (donor antibody) with the desired specificity, affinity and ability, such as mouse, rat or rabbit.

In addition, it is also possible to mutate amino acid residues in the CDR1, CDR2 and/or CDR3 regions of VH and/or VL in humanization process, thereby improving one or more binding properties (such as affinity) of the antibody. For example, mutations can be introduced, by PCR-mediation, the impact of the mutations on antibody binding or other functional properties can be assessed using in vitro or in vivo assays described herein. Usually, conservative mutations are introduced. Such mutations can be amino acid substitutions, additions, or deletions. In addition, there are usually no more than one or two mutations in the CDR. Therefore, the humanized antibody of the present disclosure also encompasses antibodies containing one or two amino acid mutations in the CDR.

As used herein, the term "epitope" refers to any antigenic determinants on the antigen, which binding to the paratope of an antibody. Epitopic determinants usually contain chemically active surface groupings of molecules, such as amino acids or sugar side chains, and usually have specific three-dimensional structural characteristics and specific charge characteristics.

As used herein, "specifically bind" or "immunospecifically bind" with respect to an antibody or an antigen-binding fragment thereof can be used interchangeably herein and refers to the ability of forming one or more non-covalent bonds between antibody or antigen-binding fragment and the alloantigen by non-covalent interactions between antibody and the antibody-binding site of the antigen. The antigen may be isolated antigen or present in tumor cells. Typically, an antibody which immunospecifically binds (or specifically binds) to an antigen binds to the antigen with an affinity constant Ka of about $1\times10^7 M^{-1}$ or $1\times10^8 M^{-1}$ or more (or with a dissociation constant (Kd) of $1\times10^{-7}$M or $1\times10^{-8}$M or less). Affinity constants can be determined by standard kinetic methods of antibody responses, for example, immunoassays, surface plasmon resonance (SPR) (Rich and Myszka (2000) Curr. Opin. Biotechnol 11:54; Englebienne (1998) Analyst. 123: 1599), isothermal titration calorimetry (ITC) or other kinetic interaction assays known in the art; see also U.S. Pat. No. 7,229,619 which describes exemplary SPR and ITC methods for calculating the binding affinity of antibodies). Instruments and methods for detecting and monitoring the rate of binding in real time are known and commercially available.

As used herein, the term "competing" with respect to antibodies means that a first antibody or antigen-binding fragment thereof binds to an epitope in a manner sufficiently similar to a second antibody or antigen-binding fragment thereof, whereby the binding result of the first antibody to the associated epitope thereof is detectably reduced in the presence of the second antibody compared to that in the absence of the second antibody. Alternatively, the binding of the second antibody to the associated epitope thereof may be, but not necessarily, detectably reduced in the presence of the first antibody compared to that in the absence of the first antibody. In other words, the first antibody can inhibit the binding of the second antibody to the epitope thereof, however the second antibody is not necessarily to inhibit the binding of the first antibody to the corresponding epitope thereof. However, in the case where each antibody can detectably inhibit the binding of another antibody to the associated epitope or ligand thereof, whether in an identical, higher or lower degree, the antibodies are called to as "cross-competitively" binding to the respective epitopes thereof. Both competing and cross-competing antibodies are included in the present disclosure. Regardless of the mechanism of the such competing or cross-competing (for example, steric hindrance, conformational change, or binding to a common epitope or a fragment thereof), those skilled in the art will be aware of such competing and/or cross-competing antibodies are encompassed by the present disclosure and can be used in the method disclosed in the present disclosure based on the teachings provided in the present disclosure.

As used herein, the terms "polynucleotide" and "nucleic acid molecule" refer to the oligomer or polymer comprising at least two linked nucleotides or nucleotide derivatives, including deoxyribonucleic acid (DNA) and ribonucleic acid (RNA) which usually linked by a phosphodiester bond. As used herein, the term "nucleic acid molecule" is intended to include DNA molecules and RNA molecules. The nucleic acid molecule can be single-stranded or double-stranded and can be cDNA.

As used herein, an isolated nucleic acid molecule is a nucleic acid molecule which is isolated from other nucleic acid molecules present in the natural sources of the nucleic acid molecule. An "isolated" nucleic acid molecule such as cDNA molecule may be substantially free of other cellular materials or culture medium when prepared by recombinant technology or substantially free of chemical precursors or other chemical components during the chemical synthesis. The exemplary isolated nucleic acid molecules provided herein include isolated nucleic acid molecules encoding the provided antibodies or antigen-binding fragments.

As used herein, "operably linked" with nucleic acid sequences, regions, elements, or domains means that the nucleic acid regions are functionally related to each other. For example, a promoter can be operably linked to a nucleic acid encoding a polypeptide, which enables the promoter to regulate or mediate transcription of the nucleic acid.

The "conservative sequence modification" of the sequence described in the sequence listing herein is also provided, that is, nucleotide and amino acid sequence modifications that do not eliminate the binding of an antibody encoded by a nucleotide sequence or containing an amino acid sequence to an antigen. These conservative sequence modifications include conservative nucleotide and amino acid substitutions, and nucleotide and amino acid additions and deletions. For example, modifications can be introduced into the sequence listing described herein by standard techniques known in the art (such as site-directed mutagenesis and PCR-mediated mutagenesis). Conservative sequence modifications include conservative amino acid substitutions in which amino acid residues are replaced with amino acid residues with similar side chains. The family of amino acid residues with similar side chains is defined in the art. These families include amino acids with basic side chains (e.g., lysine, arginine, histidine), amino acids with acidic side chains (e.g., aspartic acid, glutamic acid), and amino acids with uncharged polar side chains (e.g., glycine, asparagine, glutamine, serine, threonine, tyrosine, cysteine, tryptophan), amino acids with non-polar side chains (e.g., alanine, valine, leucine, isoleucine, proline, phenylalanine, methionine), amino acids with β-branched side chains (e.g., threonine, valine, isoleucine) and amino acids with aromatic side chains (e.g., tyrosine, phenylalanine, tryptophan, histidine). Therefore, the predicted non-essential amino acid residue in the anti-Claudin 18.2 antibody is preferably replaced by another amino acid residue from the same side chain family. Methods for identifying conservative substitutions of nucleotides and amino acids that do not eliminate antigen binding are well-known in the art (for example, referring to Brummell et al., Biochem. 32: 1180-1187 (1993); Kobayashi et al., Protein Eng. 12(10):879-884 (1999); and Burks et al., Proc. Natl. Acad. Sci. USA 94:412-417 (1997).

As another option, in another embodiment, mutations can be randomly introduced along all or part of the coding sequence of anti-Claudin 18.2 antibody by, for example, saturation mutagenesis, and the resulting modified anti-Claudin 18.2 antibody can be screened for the improved binding activity.

As used herein, "expression" refers to the process of producing the polypeptide through the transcription and translation of polynucleotides. The expression level of a polypeptide can be evaluated by any method known in the art, including, for example, the method of measuring the amount of the polypeptide produced from the host cell. Such methods may include, but not limited to, the quantification of polypeptides in cell lysates by ELISA, Coomassie blue staining after gel electrophoresis, Lowry protein determination, and Bradford protein determination.

As used herein, a "host cell" refers to a cell used to receive, maintain, replicate, and amplify a vector. Host cells can also be used to express the polypeptide encoded by the vector. When the host cell divides, the nucleic acid contained in the vector replicates, thereby amplifying the nucleic acid. Host cells can be eukaryotic cells or prokaryotic cells. Suitable host cells include, but not limited to, CHO cells, various COS cells, HeLa cells, HEK cells such as HEK 293 cells.

As used herein, a "vector" is a replicable nucleic acid from which one or more heterologous proteins can be expressed when the vector is transformed into an appropriate host cell. The vector as used herein includes those vectors into which a nucleic acid encoding a polypeptide or a fragment thereof can be introduced, typically, by restriction digestion and ligation. The Vector as used herein also includes the vector containing a nucleic acid encoding a polypeptide. The vector is used to introduce the nucleic acid encoding a polypeptide into a host cell, to amplify the nucleic acid or to express/display a polypeptide encoded by a nucleic acid. The vector usually remains free but can be designed so that to integrate the gene or a part thereof into the chromosome of the genome. The vectors of artificial chromosomes are also considered, such as yeast artificial vectors and mammalian artificial chromosomes. The selection and use of such vehicles are well known to those skilled in the art.

As used herein, vectors also include "viral vectors" or "the vectors of virus". The vector of viral is an engineered virus which can be operably linked to an exogenous gene to transfer (as a vehicle or shuttle) the exogenous gene into a cell.

As used herein, "expression vector" includes a vector capable of expressing DNA, which can be operably linked to a regulatory sequence, such as a promoter region, that is capable of affecting expression of such DNA fragments. Such additional fragments may include promoter and terminator sequences, and may optionally include one or more origins of replication, one or more selection markers, an enhancer, a polyadenylation signal, etc. Expression vectors are generally derived from plasmid or viral DNA or may contain elements of both. Therefore, an expression vector refers to a recombinant DNA or RNA construct, such as a plasmid, phage, recombinant virus, or other vector, when introduced into an appropriate host cell, results in expression of the cloned DNA. Appropriate expression vectors are well known to those skilled in the art and include expression vectors that can replicate in eukaryotic and/or prokaryotic cells and expression vectors that remain free or expression vectors that are integrated into the host cell genome.

As used herein, "treating" an individual suffering from a disease or disease condition means that the symptoms of the individual are partially or completely relieved or remain unchanged after treatment. Therefore, treating includes preventing, treating and/or curing. Preventing refers to the prevention of underlying diseases and/or prevention of worsening symptoms or disease progression. Treating also includes any pharmaceutical uses of any of the provided antibodies or antigen-binding fragments thereof and the compositions provided herein.

As used herein, "therapeutic effect" refers to an effect caused by the treatment in an individual, which changes, generally ameliorates, or improves the symptoms of diseases or conditions or cures disease or conditions.

As used herein, "therapeutically effective amount" or "therapeutically effective dose" refers to an amount of a substance, compound, material, or composition containing the compound which is at least sufficient to produce therapeutically effect after administered to a subject. Therefore, it is an amount necessary to prevent, cure, ameliorate, block, or partially block the symptoms of a disease or condition.

As used herein, "prophylactically effective amount" or "prophylactically effective dose" refers to an amount of a substance, compound, material, or composition containing the compound which exerts the desired prophylatic effect when administered to a subject, for example, to prevent or delay the onset or recurrence of a disease or symptom, reduce the possibility of the occurrence or recurrence of a disease or symptom. The complete prophylactically effective dose does not necessarily occur by administration one dose and may occur after administration of a series of doses. Therefore, a prophylactically effective amount can be administered in one or more applications.

As used herein, the term "patient" refers to a mammalian, such as human.

II. Detailed Description of Embodiments

In one aspect, the present disclosure provides an antibody or antigen binding portion thereof that binds to human Claudin 18.2, comprising the heavy chain CDR selected from amino acid sequences SEQ ID NO: 2-4, 12-14, 22-24, 32-34, 42-44, 52-54, 62-64, 72-74, 82-84, 92-94, 102-104, 112-114, 122-124, 132-134, 142-144, 152-154, 157-159, 162-164, 167-169, 172-174, 177-179, 182-184, 187-189, 192-194, 197-199, 202-204, 207-209, 212-214, 217-219, 222-224, 227-229, 232-234 or any variant thereof, and/or comprises the light chain CDR selected from amino acid sequences SEQ ID NO: 7-9, 17-19, 27-29, 37-39, 47-49, 57-59, 67-69, 77-79, 87-89, 97-99, 107-109, 117-119, 127-

129, 137-139, 147-149, 237-239, 242-244, 247-249, 252-254, 257-259, 262-264, 267-269 or any variant thereof.

The antibody or antigen binding portion thereof according to the preceding aspect, comprising the heavy chain CDR1 selected from amino acid sequences SEQ ID NO: 2, 12, 22, 32, 42, 52, 62, 72, 82, 92, 102, 112, 122, 132, 142, 152, 157, 162, 167, 172, 177, 182, 187, 192, 197, 202, 207, 212, 217, 222, 227, 232 or any variant thereof, the heavy chain CDR2 selected from amino acid sequences SEQ ID NO: 3, 13, 23, 33, 43, 53, 63, 73, 83, 93, 103, 113, 123, 133, 143, 153, 158, 163, 168, 173, 178, 183, 188, 193, 198, 203, 208, 213, 218, 223, 228, 233 or any variant thereof, the heavy chain CDR3 selected from amino acid sequences SEQ ID NO: 4, 14, 24, 34, 44, 54, 64, 74, 84, 94, 104, 114, 124, 134, 144, 154, 159, 164, 169, 174, 179, 184, 189, 194, 199, 204, 209, 214, 219, 224, 229, 234 or any variant thereof; and/or the light chain CDR1 selected from amino acid sequences SEQ ID NO: 7, 17, 27, 37, 47, 57, 67, 77, 87, 97, 107, 117, 127, 137, 147, 237, 242, 247, 252, 257, 262, 267 or any variant thereof, the light chain CDR2 selected from amino acid sequences SEQ ID NO: 8, 18, 28, 38, 48, 58, 68, 78, 88, 98, 108, 118, 128, 138, 148, 238, 243, 248, 253, 258, 263, 268 or any variant thereof, the light chain CDR3 selected from amino acid sequences SEQ ID NO: 9, 19, 29, 39, 49, 59, 69, 79, 89, 99, 109, 119, 129, 139, 149, 239, 244, 249, 254, 259, 264, 269 or any variant thereof.

The antibody or antigen binding portion thereof according to any one of the preceding aspects, comprising the heavy chain variable region selected from amino acid sequences SEQ ID NO: 1, 11, 21, 31, 41, 51, 61, 71, 81, 91, 101, 111, 121, 131, 141, 151, 156, 161, 166, 171, 176, 181, 186, 191, 196, 201, 206, 211, 216, 221, 226, 231 or any variant thereof, and/or the light chain variable region selected from amino acid sequences SEQ ID NO: 6, 16, 26, 36, 46, 56, 66, 76, 86, 96, 106, 116, 126, 136, 146, 236, 241, 246, 251, 256, 261, 266 or any variant thereof.

A nucleic acid molecule encoding the antibody or antigen binding portion thereof according to any one of the preceding aspects, comprising the antibody heavy chain nucleic acid sequence selected from selected from the group consisting of SEQ ID NO: 5, 15, 25, 35, 45, 55, 65, 75, 85, 95, 105, 115, 125, 135, 145, 155, 160, 165, 170, 175, 180, 185, 190, 195, 200, 205, 210, 215, 220, 225, 230, 235 or any variant thereof, and/or the antibody light chain nucleic acid sequence selected from the group consisting of SEQ ID NO: 10, 20, 30, 40, 50, 60, 70, 80, 90, 100, 110, 120, 130, 140, 150, 240, 245, 250, 255, 260, 265, 270 or any variant thereof.

In one aspect, the present disclosure relates to an antibody or antigen binding portion thereof that binds to human Claudin 18.2, comprising the heavy chain variable region selected from amino acid sequences SEQ ID NO: 151, 156, 161, 166, 171, 176, 181, 186, 191, 196, 201, 206, 211, 216, 221, 226, 231 or any variant thereof, and/or the light variable region selected from the amino acid sequence SEQ ID NO: 236, 241, 246, 251, 256, 261, 266 or any variant thereof.

In one aspect, the present disclosure relates to an antibody or antigen binding portion thereof that binds to human Claudin 18.2, comprising the heavy chain variable region selected from amino acid sequences SEQ ID NO: 151 or any variant thereof, and/or the light chain variable region selected from amino acid sequences SEQ ID NO: 236 or any variants thereof.

In one aspect, the present disclosure relates to an antibody or antigen binding portion thereof that binds to human Claudin 18.2, comprising the heavy chain variable region selected from amino acid sequences SEQ ID NO: 151 or any variant thereof, and/or the light chain variable region selected from amino acid sequences SEQ ID NO: 241 or any variants thereof.

In one aspect, the present disclosure relates to an antibody or antigen binding portion thereof that binds to human Claudin 18.2, comprising the heavy chain variable region selected from amino acid sequences SEQ ID NO: 151 or any variant thereof, and/or the light chain variable region selected from amino acid sequences SEQ ID NO: 256 or any variants thereof.

In one aspect, the present disclosure relates to an antibody or antigen binding portion thereof that binds to human Claudin 18.2, comprising the heavy chain variable region selected from amino acid sequences SEQ ID NO: 156 or any variant thereof, and/or the light chain variable region selected from amino acid sequences SEQ ID NO: 236 or any variants thereof.

In one aspect, the present disclosure relates to an antibody or antigen binding portion thereof that binds to human Claudin 18.2, comprising the heavy chain variable region selected from amino acid sequences SEQ ID NO: 156 or any variant thereof, and/or the light chain variable region selected from amino acid sequences SEQ ID NO: 241 or any variants thereof.

In one aspect, the present disclosure relates to an antibody or antigen binding portion thereof that binds to human Claudin 18.2, comprising the heavy chain variable region selected from amino acid sequences SEQ ID NO: 156 or any variant thereof, and/or the light chain variable region selected from amino acid sequences SEQ ID NO: 256 or any variants thereof.

In one aspect, the present disclosure relates to an antibody or antigen binding portion thereof that binds to human Claudin 18.2, comprising the heavy chain variable region selected from amino acid sequences SEQ ID NO: 161 or any variant thereof, and/or the light chain variable region selected from amino acid sequences SEQ ID NO: 236 or any variants thereof.

In one aspect, the present disclosure relates to an antibody or antigen binding portion thereof that binds to human Claudin 18.2, comprising the heavy chain variable region selected from amino acid sequences SEQ ID NO: 161 or any variant thereof, and/or the light chain variable region selected from amino acid sequences SEQ ID NO: 241 or any variants thereof.

In one aspect, the present disclosure relates to an antibody or antigen binding portion thereof that binds to human Claudin 18.2, comprising the heavy chain variable region selected from amino acid sequences SEQ ID NO: 161 or any variant thereof, and/or the light chain variable region selected from amino acid sequences SEQ ID NO: 256 or any variants thereof.

In one aspect, the present disclosure relates to an antibody or antigen binding portion thereof that binds to human Claudin 18.2, comprising the heavy chain variable region selected from amino acid sequences SEQ ID NO: 166 or any variant thereof, and/or the light chain variable region selected from amino acid sequences SEQ ID NO: 236 or any variants thereof.

In one aspect, the present disclosure relates to an antibody or antigen binding portion thereof that binds to human Claudin 18.2, comprising the heavy chain variable region selected from amino acid sequences SEQ ID NO: 166 or any variant thereof, and/or the light chain variable region selected from amino acid sequences SEQ ID NO: 241 or any variants thereof.

In one aspect, the present disclosure relates to an antibody or antigen binding portion thereof that binds to human Claudin 18.2, comprising the heavy chain variable region selected from amino acid sequences SEQ ID NO: 166 or any variant thereof, and/or the light chain variable region selected from amino acid sequences SEQ ID NO: 256 or any variants thereof.

In one aspect, the present disclosure relates to an antibody or antigen binding portion thereof that binds to human Claudin 18.2, comprising the heavy chain variable region selected from amino acid sequences SEQ ID NO: 171 or any variant thereof, and/or the light chain variable region selected from amino acid sequences SEQ ID NO: 251 or any variants thereof.

In one aspect, the present disclosure relates to an antibody or antigen binding portion thereof that binds to human Claudin 18.2, comprising the heavy chain variable region selected from amino acid sequences SEQ ID NO: 171 or any variant thereof, and/or the light chain variable region selected from amino acid sequences SEQ ID NO: 256 or any variants thereof.

In one aspect, the present disclosure relates to an antibody or antigen binding portion thereof that binds to human Claudin 18.2, comprising the heavy chain variable region selected from amino acid sequences SEQ ID NO: 176 or any variant thereof, and/or the light chain variable region selected from amino acid sequences SEQ ID NO: 251 or any variants thereof.

In one aspect, the present disclosure relates to an antibody or antigen binding portion thereof that binds to human Claudin 18.2, comprising the heavy chain variable region selected from amino acid sequences SEQ ID NO: 176 or any variant thereof, and/or the light chain variable region selected from amino acid sequences SEQ ID NO: 256 or any variants thereof.

In one aspect, the present disclosure relates to an antibody or antigen binding portion thereof that binds to human Claudin 18.2, comprising the heavy chain variable region selected from amino acid sequences SEQ ID NO: 181 or any variant thereof, and/or the light chain variable region selected from amino acid sequences SEQ ID NO: 251 or any variants thereof.

In one aspect, the present disclosure relates to an antibody or antigen binding portion thereof that binds to human Claudin 18.2, comprising the heavy chain variable region selected from amino acid sequences SEQ ID NO: 181 or any variant thereof, and/or the light chain variable region selected from amino acid sequences SEQ ID NO: 256 or any variants thereof.

In one aspect, the present disclosure relates to an antibody or antigen binding portion thereof that binds to human Claudin 18.2, comprising the heavy chain variable region selected from amino acid sequences SEQ ID NO: 186 or any variant thereof, and/or the light chain variable region selected from amino acid sequences SEQ ID NO: 251 or any variants thereof.

In one aspect, the present disclosure relates to an antibody or antigen binding portion thereof that binds to human Claudin 18.2, comprising the heavy chain variable region selected from amino acid sequences SEQ ID NO: 186 or any variant thereof, and/or the light chain variable region selected from amino acid sequences SEQ ID NO: 256 or any variants thereof.

In one aspect, the present disclosure relates to an antibody or antigen binding portion thereof that binds to human Claudin 18.2, comprising the heavy chain variable region selected from amino acid sequences SEQ ID NO: 191 or any variant thereof, and/or the light chain variable region selected from amino acid sequences SEQ ID NO: 251 or any variants thereof.

In one aspect, the present disclosure relates to an antibody or antigen binding portion thereof that binds to human Claudin 18.2, comprising the heavy chain variable region selected from amino acid sequences SEQ ID NO: 191 or any variant thereof, and/or the light chain variable region selected from amino acid sequences SEQ ID NO: 256 or any variants thereof.

In one aspect, the present disclosure relates to an antibody or antigen binding portion thereof that binds to human Claudin 18.2, comprising the heavy chain variable region selected from amino acid sequences SEQ ID NO: 196 or any variant thereof, and/or the light chain variable region selected from amino acid sequences SEQ ID NO: 251 or any variants thereof.

In one aspect, the present disclosure relates to an antibody or antigen binding portion thereof that binds to human Claudin 18.2, comprising the heavy chain variable region selected from amino acid sequences SEQ ID NO: 196 or any variant thereof, and/or the light chain variable region selected from amino acid sequences SEQ ID NO: 256 or any variants thereof.

In one aspect, the present disclosure relates to an antibody or antigen binding portion thereof that binds to human Claudin 18.2, comprising the heavy chain variable region selected from amino acid sequences SEQ ID NO: 201 or any variant thereof, and/or the light chain variable region selected from amino acid sequences SEQ ID NO: 251 or any variants thereof.

In one aspect, the present disclosure relates to an antibody or antigen binding portion thereof that binds to human Claudin 18.2, comprising the heavy chain variable region selected from amino acid sequences SEQ ID NO: 201 or any variant thereof, and/or the light chain variable region selected from amino acid sequences SEQ ID NO: 256 or any variants thereof.

In one aspect, the present disclosure relates to an antibody or antigen binding portion thereof that binds to human Claudin 18.2, comprising the heavy chain variable region selected from amino acid sequences SEQ ID NO: 206 or any variant thereof, and/or the light chain variable region selected from amino acid sequences SEQ ID NO: 261 or any variants thereof.

In one aspect, the present disclosure relates to an antibody or antigen binding portion thereof that binds to human Claudin 18.2, comprising the heavy chain variable region selected from amino acid sequences SEQ ID NO: 206 or any variant thereof, and/or the light chain variable region selected from amino acid sequences SEQ ID NO: 266 or any variants thereof.

In one aspect, the present disclosure relates to an antibody or antigen binding portion thereof that binds to human Claudin 18.2, comprising the heavy chain variable region selected from amino acid sequences SEQ ID NO: 211 or any variant thereof, and/or the light chain variable region selected from amino acid sequences SEQ ID NO: 261 or any variants thereof.

In one aspect, the present disclosure relates to an antibody or antigen binding portion thereof that binds to human Claudin 18.2, comprising the heavy chain variable region selected from amino acid sequences SEQ ID NO: 211 or any variant thereof, and/or the light chain variable region selected from amino acid sequences SEQ ID NO: 266 or any variants thereof.

In one aspect, the present disclosure relates to an antibody or antigen binding portion thereof that binds to human Claudin 18.2, comprising the heavy chain variable region selected from amino acid sequences SEQ ID NO: 216 or any variant thereof, and/or the light chain variable region selected from amino acid sequences SEQ ID NO: 261 or any variants thereof.

In one aspect, the present disclosure relates to an antibody or antigen binding portion thereof that binds to human Claudin 18.2, comprising the heavy chain variable region selected from amino acid sequences SEQ ID NO: 216 or any variant thereof, and/or the light chain variable region selected from amino acid sequences SEQ ID NO: 266 or any variants thereof.

In one aspect, the present disclosure relates to an antibody or antigen binding portion thereof that binds to human Claudin 18.2, comprising the heavy chain variable region selected from amino acid sequences SEQ ID NO: 221 or any variant thereof, and/or the light chain variable region selected from amino acid sequences SEQ ID NO: 261 or any variants thereof.

In one aspect, the present disclosure relates to an antibody or antigen binding portion thereof that binds to human Claudin 18.2, comprising the heavy chain variable region selected from amino acid sequences SEQ ID NO: 221 or any variant thereof, and/or the light chain variable region selected from amino acid sequences SEQ ID NO: 266 or any variants thereof.

In one aspect, the present disclosure relates to an antibody or antigen binding portion thereof that binds to human Claudin 18.2, comprising the heavy chain variable region selected from amino acid sequences SEQ ID NO: 226 or any variant thereof, and/or the light chain variable region selected from amino acid sequences SEQ ID NO: 261 or any variants thereof.

In one aspect, the present disclosure relates to an antibody or antigen binding portion thereof that binds to human Claudin 18.2, comprising the heavy chain variable region selected from amino acid sequences SEQ ID NO: 226 or any variant thereof, and/or the light chain variable region selected from amino acid sequences SEQ ID NO: 266 or any variants thereof.

In one aspect, the present disclosure relates to an antibody or antigen binding portion thereof that binds to human Claudin 18.2, comprising the heavy chain variable region selected from amino acid sequences SEQ ID NO: 231 or any variant thereof, and/or the light chain variable region selected from amino acid sequences SEQ ID NO: 261 or any variants thereof.

In one aspect, the present disclosure relates to an antibody or antigen binding portion thereof that binds to human Claudin 18.2, comprising the heavy chain variable region selected from amino acid sequences SEQ ID NO: 231 or any variant thereof, and/or the light chain variable region selected from amino acid sequences SEQ ID NO: 266 or any variants thereof.

In one specific embodiment, the present disclosure provides an antibody or antigen binding portion thereof that binds to human Claudin 18.2, comprising the heavy chain CDR selected from amino acid sequences SEQ ID NO: 152-154, 157-159, 162-164, 167-169, 172-174, 177-179, 182-184, 187-189, 192-194, 197-199, 202-204, 207-209, 212-214, 217-219, 222-224, 227-229, 232-234 or any variant thereof, and/or the light chain CDR selected from amino acid sequences SEQ ID NO: 237-239, 242-244, 247-249, 252-254, 257-259, 262-264, 267-269 or any variant thereof.

An antibody or antigen-binding portion thereof that binds to human Claudin 18.2, comprising the combination of CDRs selected from the following heavy and light chains: (1) heavy chain CDR1, CDR2 and CDR3 sequences respectively comprising SEQ ID NO: 152-154, and/or light chain CDR1, CDR2 and CDR3 sequences respectively comprising SEQ ID NO: 237-239; (2) heavy chain CDR1, CDR2 and CDR3 sequences respectively comprising SEQ ID NO: 152-154, and/or light chain CDR1, CDR2 and CDR3 sequences respectively comprising SEQ ID NO: 242-244; (3) heavy chain CDR1, CDR2 and CDR3 sequences respectively comprising SEQ ID NO: 152-154, and/or light chain CDR1, CDR2 and CDR3 sequences respectively comprising SEQ ID NO:247-249; (4) heavy chain CDR1, CDR2 and CDR3 sequences respectively comprising SEQ ID NO: 157-159, and/or light chain CDR1, CDR2 and CDR3 sequences respectively comprising SEQ ID NO: 237-239; (5) heavy chain CDR1, CDR2 and CDR3 sequences respectively comprising SEQ ID NO: 157-159, and/or light chain CDR1, CDR2 and CDR3 sequences respectively comprising SEQ ID NO: 242-244; (6) heavy chain CDR1, CDR2 and CDR3 sequences respectively comprising SEQ ID NO: 157-159, and/or light chain CDR1, CDR2 and CDR3 sequences respectively comprising SEQ ID NO: 247-249; (7) heavy chain CDR1, CDR2 and CDR3 sequences respectively comprising SEQ ID NO: 162-164, and/or light chain CDR1, CDR2 and CDR3 sequences respectively comprising SEQ ID NO: 237-239; (8) heavy chain CDR1, CDR2 and CDR3 sequences respectively comprising SEQ ID NO: 162-164, and/or light chain CDR1, CDR2 and CDR3 sequences respectively comprising SEQ ID NO: 242-244; (9) heavy chain CDR1, CDR2 and CDR3 sequences respectively comprising SEQ ID NO: 162-164, and/or light chain CDR1, CDR2 and CDR3 sequences respectively comprising SEQ ID NO: 247-249; (10) heavy chain CDR1, CDR2 and CDR3 sequences respectively comprising SEQ ID NO: 167-169, and/or light chain CDR1, CDR2 and CDR3 sequences respectively comprising SEQ ID NO: 237-239; (11) heavy chain CDR1, CDR2 and CDR3 sequences respectively comprising SEQ ID NO: 167-169, and/or light chain CDR1, CDR2 and CDR3 sequences respectively comprising SEQ ID NO: 242-244; (12) heavy chain CDR1, CDR2 and CDR3 sequences respectively comprising SEQ ID NO: 167-169, and/or light chain CDR1, CDR2 and CDR3 sequences respectively comprising SEQ ID NO: 247-249; (13) heavy chain CDR1, CDR2 and CDR3 sequences respectively comprising SEQ ID NO: 172-174, and/or light chain CDR1, CDR2 and CDR3 sequences respectively comprising SEQ ID NO: 252-254; (14) heavy chain CDR1, CDR2 and CDR3 sequences respectively comprising SEQ ID NO: 172-174, and/or light chain CDR1, CDR2 and CDR3 sequences respectively comprising SEQ ID NO: 257-259; (15) heavy chain CDR1, CDR2 and CDR3 sequences respectively comprising SEQ ID NO: 177-179, and/or light chain CDR1, CDR2 and CDR3 sequences respectively comprising SEQ ID NO: 252-254; (16) heavy chain CDR1, CDR2 and CDR3 sequences respectively comprising SEQ ID NO: 177-179, and/or light chain CDR1, CDR2 and CDR3 sequences respectively comprising SEQ ID NO: 257-259; (17) heavy chain CDR1, CDR2 and CDR3 sequences respectively comprising SEQ ID NO: 182-184, and/or light chain CDR1, CDR2 and CDR3 sequences respectively comprising SEQ ID NO: 252-254; (18) heavy chain CDR1, CDR2 and CDR3 sequences respectively comprising SEQ ID NO: 182-184, and/or light chain CDR1, CDR2 and CDR3 sequences respectively comprising SEQ ID NO: 257-259; (19) heavy chain CDR1, CDR2 and CDR3 sequences respectively comprising SEQ ID NO: 187-189, and/or light chain CDR1, CDR2 and CDR3 sequences respectively comprising SEQ ID NO: 252-254; (20) heavy chain CDR1, CDR2 and CDR3 sequences respectively comprising SEQ ID NO: 187-189, and/or light chain CDR1, CDR2 and CDR3 sequences respectively comprising SEQ ID NO: 257-259; (21) heavy chain CDR1, CDR2 and CDR3 sequences respectively comprising SEQ ID NO: 192-194, and/or light chain CDR1, CDR2 and CDR3 sequences respectively comprising SEQ ID NO: 252-254; (22) heavy chain CDR1, CDR2 and CDR3 sequences respectively comprising SEQ ID NO: 192-194, and/or light chain CDR1, CDR2 and CDR3 sequences respectively comprising SEQ ID NO: 257-259; (23) heavy chain CDR1, CDR2 and CDR3 sequences respectively comprising SEQ ID NO: 197-199, and/or light chain CDR1, CDR2 and CDR3 sequences respectively comprising SEQ ID NO: 252-254; (24) heavy chain CDR1, CDR2 and CDR3 sequences respectively comprising SEQ ID NO: 197-199, and/or light chain CDR1, CDR2 and CDR3 sequences respectively comprising SEQ ID NO: 257-259; (25) heavy chain CDR1, CDR2 and CDR3 sequences respectively comprising SEQ ID NO: 202-204, and/or light chain CDR1, CDR2 and CDR3 sequences respectively comprising SEQ ID NO: 252-254; (26) heavy chain CDR1, CDR2 and CDR3 sequences respectively comprising SEQ ID NO: 202-204, and/or light chain CDR1, CDR2 and CDR3 sequences respectively comprising SEQ ID NO: 257-259; (27) heavy chain CDR1, CDR2 and CDR3 sequences respectively comprising SEQ ID NO: 207-209, and/or light chain CDR1, CDR2 and CDR3 sequences respectively comprising SEQ ID NO: 262-264; (28) heavy chain CDR1, CDR2 and CDR3 sequences respectively comprising SEQ ID NO: 207-209, and/or light chain CDR1, CDR2 and CDR3 sequences respectively comprising SEQ ID NO: 267-269; (29) heavy chain CDR1, CDR2 and CDR3 sequences respectively comprising SEQ ID NO: 212-214, and/or light chain CDR1, CDR2 and CDR3 sequences respectively comprising SEQ ID NO: 262-264; (30) heavy chain CDR1, CDR2 and CDR3 sequences respectively comprising SEQ ID NO: 212-214, and/or light chain CDR1, CDR2 and CDR3 sequences respectively comprising SEQ ID NO: 267-269; (31) heavy chain CDR1, CDR2 and CDR3 sequences respectively comprising SEQ ID NO: 217-219, and/or light chain CDR1, CDR2 and CDR3 sequences comprising SEQ ID NO: 262-264 respectively; (32) heavy chain CDR1, CDR2 and CDR3 sequences respectively comprising SEQ ID NO: 217-219, and/or light chain CDR1, CDR2 and CDR3 sequences respectively comprising SEQ ID NO: 267-269; (33) heavy chain CDR1, CDR2 and CDR3 sequences respectively comprising SEQ ID NO: 222-224, and/or light chain CDR1, CDR2 and CDR3 sequences respectively comprising SEQ ID NO: 262-264; (34) heavy chain CDR1, CDR2 and CDR3 sequences respectively comprising SEQ ID NO: 222-224, and/or light chain CDR1, CDR2 and CDR3 sequences respectively comprising SEQ ID NO: 267-269; (35) heavy chain CDR1, CDR2 and CDR3 sequences respectively comprising SEQ ID NO: 227-229, and/or light chain CDR1, CDR2 and CDR3 sequences respectively comprising SEQ ID NO: 262-264; (36) heavy chain CDR1, CDR2 and CDR3 sequences respectively comprising SEQ ID NO: 227-229, and/or light chain CDR1, CDR2 and CDR3 sequences respectively comprising SEQ ID NO: 267-269; (37) heavy chain CDR1, CDR2 and CDR3 sequences respectively comprising SEQ ID NO: 232-234, and/or light chain CDR1, CDR2 and CDR3 sequences respectively comprising SEQ ID NO: 262-264; (38) heavy chain CDR1, CDR2 and CDR3 sequences respectively comprising SEQ ID NO: 232-234, and/or light chain CDR1 CDR2 and CDR3 sequences respectively comprising SEQ ID NO: 267-269.

An antibody or antigen binding portion thereof that binds to human Claudin 18.2, which has at least greater than 60%, 65%, 70%, 75%, 80%, 85%, 90% 95%, 96%, 97%, 98%, 99% or higher sequence identity with the antibody or antigen binding portion thereof of any one of the preceding aspects.

A nucleic acid molecule encoding an antibody or an antigen-binding portion thereof according to any one of the preceding aspects, or a nucleic acid molecule having at least greater than 60%, 65%, 70%, 75%, 80%, 85%, 90%, 95%, 96%, 97%, 98%, 99% or higher sequence identity thereto.

A vector comprising the nucleic acid of any one of the preceding aspects.

A cell comprising the vector of any one of the preceding aspects.

A pharmaceutical composition comprising the antibody or antigen binding portion thereof, or the nucleic acid encoding same of any one of the preceding aspects and a pharmaceutically acceptable carrier.

A method for treating cancer comprising the following steps: administering to the mammal a therapeutically effective amount of the antibody or antigen binding fragment thereof or the nucleic acid molecules encoding same or the vector or the cell or the pharmaceutical composition of any one of the preceding aspects.

Use of the antibody or antigen binding fragment thereof, or the nucleic acid molecule, or the vector, or the cell or the pharmaceutical composition of any one of the preceding aspects, in the preparation of a medicament for the treatment of cancer in a mammal.

According to any one of the preceding aspects, optionally, the cancer is gastric cancer. Optionally, the antibody kills cancer cells through ADCC or CDC effects. Optionally, the antibody conjugates to other drugs, such as labeled or cytotoxic conjugates.

In one aspect, the present disclosure also includes kits, for example, the kits include the antibodies, fragments, homologues, derivatives thereof, etc. of the present disclosure, such as labeled or cytotoxic conjugates, and instructions for use of the antibody, conjugates which kill specific types of cells, etc. The instructions may include guidance for using antibodies, conjugates, and the like in vitro, in vivo, or ex vivo. The antibody may be in a liquid form or in a solid form, typically in a lyophilized. The kit may contain other suitable agents, such as buffers, reconstitution solutions, and other necessary ingredients for the intended use. The combination of agents packaged in predetermined amounts and instructions for use are considered, wherein the use is, for example, for therapeutic use or for performing diagnostic assays. When the antibody is labeled, for example, labeled with an enzyme, the kit may include a substrate and a cofactor required for the enzyme (for example, a substrate precursor that provides a detectable chromophore or fluorophore). In addition, other additives, such as stabilizers, buffers (for example, blocking buffers or lysis buffers), and the like may also be included. The relative amounts of the multiple agents can be changed to provide a concentrate of the agent solution, which provides user flexibility, space savings, agent savings, and the like. These agents can also be provided in a form of the dry powder, usually in a lyophilized form, including excipients, which can provide an agent solution with an appropriate concentration when dissolved.

Use of the antibody or functional fragment thereof or nucleic acid molecule or vector or cell or pharmaceutical composition or kit of any one of the preceding aspects in the preparation of the reagent for mediating the endocytosis of cell surface Claudin 18.2.

The present disclosure also includes multivalent antibodies, including bispecific anti-Claudin 18.2 antibodies, which have attached effector molecules, atoms, or other substances with diagnostic or therapeutic functions. For example, an antibody may have a radioactive diagnostic label or a radioactive cytotoxic atom or a metal or cytotoxic substance such as a ricin chain, which is attached to the antibody for in vivo diagnosis or treatment of cancer.

In addition, the antibodies of the present disclosure can also be used in immunoassays, purification methods, and other methods using immunoglobulins or fragments thereof. Such uses are well known in the art.

Correspondingly, the present disclosure also provides the composition comprising the antibody of anti-Claudin 18.2 or the fragment thereof of the present disclosure, wherein the antibody is conveniently combined with the pharmaceutically acceptable carriers, diluents, or excipients, which is a common means in the art.

The term "pharmaceutical composition" used in the present disclosure refers to formulations of various preparations. The formulations containing the therapeutically effective amount of the multivalent antibody are sterile liquid solutions, liquid suspensions or in lyophilized form, and optionally contain stabilizers or excipients.

The term "cancer" used in the present disclosure refers to or describes the physiological condition of a mammal, especially a human, and its typical feature is the unregulated growth of cells. Examples of cancer include, but not limited to, carcinoma, lymphoma, blastoma, sarcoma, and leukemia.

The antibody of the present disclosure can be used as compositions for administration alone or can be used in combination with other active agents.

It should be understood that the therapeutic agents according to the described embodiments will be administered with suitable carriers, excipients, and other agents which are incorporated into formulations to provide improved transfer, delivery, tolerance, etc. A large number of suitable formulations can be found in the pharmacopoeias known to all pharmaceutical chemists, especially in Chapter 87 of Blaug, Seymour. These formulations include, for example, powders, pastes, ointments, jellies, waxes, oils, lipids, lipid (cationic or anionic)-containing vesicles (such as Lipofectin™), DNA conjugates, anhydrous absorption pastes, oil-in-water and water-in-oil emulsions, emulsion polyethylene glycols (polyethylene glycols of various molecular weights), semi-solid gels, and semi-solid mixtures containing polyethylene glycol. Any of the preceding mixtures may be suitable for use in treatments or therapies according to the present disclosure, provided that the active ingredient in the formulation is not inactivated by the formulation and the formulation is physiologically compatible and tolerable with the route of administration.

In one embodiment, the described antibodies can be used as therapeutic agents. Such agents will generally be applied to treat, alleviate, and/or prevent a disease or pathology associated with abnormal Claudin 18.2 expression, activity, and/or signal transduction in a subject. Standard methods can be used to identify subjects, such as human patients suffering from (or at risk or developing) a disease or disorder associated with abnormal Claudin 18.2 expression, activity, and/or signal transduction, such as cancer or other neoplastic disorder, to implement the treatment plan. An antibody preparation, preferably the antibody preparation with high specificity and high affinity for the target antigen thereof, is administered to the subject and will usually have an effect due to its binding with the target. Administration of the antibody can abrogate or inhibit or interfere with the expression, activity, and/or signal transduction function of the target (e.g., Claudin 18.2). Administration of the antibody can abrogate or inhibit or interfere with the binding of the target (e.g., Claudin 18.2) with an endogenous ligand to which it naturally binds. For example, the antibody binds to the target and modulates, blocks, inhibits, reduces, antagonizes, neutralizes, or otherwise interfered with the expression, activity, and/or signal transduction of Claudin 18.2. In some embodiments, antibodies with heavy and light chain CDRs can be administered to the subject to treat diseases or disorders associated with the expression of abnormal Claudin 18.2. In one embodiment, the disease or disorder associated with the expression of abnormal Claudin 18.2 may be cancer.

As a non-limiting example, disease or disorder associated with expression, activity, and/or signal transduction of abnormal Claudin 18.2 include hematological cancers and/or solid tumors. Hematological cancers include, for example, leukemia, lymphoma, and myeloma. As a non-limiting example, some types of leukemia include acute lymphocytic leukemia (ALL); acute myeloid leukemia (AML); chronic lymphocytic leukemia (CLL); chronic myelogenous leukemia (CML); myeloproliferative Disease/neoplasm (MPDS); and Myelodysplastic Syndrome. As non-limiting examples, some types of lymphoma include Hodgkin's lymphoma, low-grade and aggressive non-Hodgkin's lymphoma, Burkitt's lymphoma, and follicular lymphoma (small cell and large cells). As a non-limiting example, some t of myeloma include multiple myeloma (MM), giant cell myeloma, heavy chain myeloma, and light chain or Bence-Jones myeloma. Solid tumors include, for example, breast tumors, ovarian tumors, lung tumors, pancreatic tumors, prostate tumors, melanomas, colorectal tumors, lung tumors, head and neck tumors, bladder tumors, esophageal tumors, liver tumors, and kidney tumors.

Symptoms associated with cancer and other neoplastic disorders include, for example, inflammation, fever, general malaise, fever, pain, frequent local inflammation, loss of appetite, weight loss, edema, headache, fatigue, rash, anemia, muscle weakness, muscle fatigue, and abdomen symptoms such as abdominal pain, dysentery, or constipation.

In another embodiment, antibodies directed against Claudin 18.2 can be used in methods known in the art relating to the localization and/or quantification of Claudin 18.2 (e.g., for use in measuring levels of Claudin 18.2 in appropriate physiological samples and/or Claudin 18.2, for use in diagnostic methods, for use in the protein imaging, etc.). In a given embodiment, antibodies which are specific with Claudin 18.2 or derivatives, fragments, analogs, or homolog thereof, and contain the antigen binding domain derived from antibodies, are used as pharmacologically active compounds (hereinafter referred to as "therapeutic agent").

In another embodiment, Claudin 18.2 polypeptides can be isolated using antibodies specific for Claudin 18.2 by standard techniques such as immunoaffinity, chromatography, or immunoprecipitation. Antibodies (or a fragment thereof) directed against Claudin 18.2 protein can be used to detect the protein in a biological sample. In some embodiments, Claudin 18.2 can be detected in biological samples as part of a clinical testing process, for example, to determine the efficacy of a given treatment regimen. Coupling (i.e., physically linking) the antibody to detectable substances can facilitate detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazine amino fluorescein, dansyl chloride, or phycoerythrin; an example of luminescent material include luminol; examples of bioluminescent materials include luciferase, luciferin, and aequorin, and examples of suitable radioactive materials include $^{125}$I, $^{131}$I, $^{35}$S, or $^3$H.

In another embodiment, an antibody according to the present disclosure can be used as an agent for detecting the presence of Claudin 18.2 or a protein fragment thereof in the samples. In some embodiments, the antibody comprises a detectable label. Antibodies are polyclonal antibodies, or more preferably, monoclonal antibodies. An intact antibody or a fragment thereof (e.g., Fab, scFv, or F(ab')$_2$) is used. The term "labeled", with respect to an antibody is intended to include labeling the antibody directly by coupling (i.e., physically linking) a detectable substance to the antibody, and labeling the antibody indirectly by reacting with another reagent which is directly labeled. Examples of indirect labeling include detection of a primary antibody using a fluorescently-labeled secondary antibody, and end-labeling of an antibody with biotin, such that it can be detected with fluorescently-labeled streptavidin. The term "biological sample" is intended to include the tissues, cells, and biological fluids isolated from a subject, as well as tissues, cells, and fluids present in a subject. Therefore, the term "biological sample" used includes blood and a fraction or component of blood, including serum, blood plasma, or lymph. In other words, the detection method of a described embodiment can be used to detect an analyte mRNA, protein, or genomic DNA in a biological sample in vitro and in vivo. For example, in vitro techniques for detection of an analyte mRNA include Northern hybridization and in situ hybridization. In vitro techniques for detection of an analyte proteins include enzyme linked immunosorbent assays (ELISAs), Western blot, immunoprecipitation, and immunofluorescence. In vitro techniques for detection of an analyte genomic DNA include Southern hybridization. In addition, in vivo techniques for detection of an analyte protein include introducing a labeled anti-analyte protein antibody into a subject. For example, the antibody can be labeled with a radioactive label, whose presence and location in a subject can be detected by standard imaging techniques.

The antibodies described herein and the derivatives, fragments, analogs, and homologs thereof can be incorporated into pharmaceutical compositions suitable for administration. Principles and considerations involved in preparing such compositions, and guidelines for selecting components are well known in the art.

Such compositions typically include the antibody and a pharmaceutically acceptable carrier. When antibody fragments are used, the smallest inhibitory fragment that specifically binds to the binding domain of the target protein may be preferred. For example, based on the variable region sequence of an antibody, peptide molecules that retain the ability to bind the target protein sequence can be designed. Such peptides can be chemically synthesized and/or produced by recombinant DNA technology (see, for example, Marasco et al., Proc. Natl. Acad. Sci. USA, 90: 7889-7893 (1993)).

As used herein, the term "pharmaceutically acceptable carrier" is intended to include any and all solvents, dispersion media, coatings, antibacterial and antifungal agents, isotonic and absorption delaying agents and the like, which are compatible with drug administration. Suitable pharmaceutically acceptable carriers are described in the latest edition of Remington's Pharmaceutical Sciences, a standard bibliography in the art, which is hereby incorporated by reference. Preferred examples of such carriers or diluents include, but not limited to, water, saline, Ringer's solution, dextrose solution, and 5% human serum albumin. Liposomes and non-aqueous carriers such as fixed oils can also be used. The use of such media and agents with pharmaceutically active substances is well known in the art. Except insofar as any conventional media or agent is incompatible with the antibody, use thereof in the composition is envisaged.

The pharmaceutical composition of the described embodiments is formulated to be compatible with their intended route of administration. Examples of routes of administration include parenteral, such as intravenous, intradermal, subcutaneous, oral (e.g., inhalation), transdermal (i.e., topical), transmucosal, and rectal administration. Solutions or suspensions for parenteral, intradermal or subcutaneous administration may include the following components: sterile diluents for injection, such as water, saline solutions, fixed oils, polyethylene glycols, glycerol, propylene glycol or other synthetic solvents; antibacterial agents, such as benzyl alcohol or methylparaben; antioxidants, such as ascorbic acid or sodium bisulfite; chelating agents, such as ethylenediaminetetraacetic acid (EDTA); buffers, such as acetate, citrate or phosphate, and the agent that regulates osmotic pressure, such as sodium chloride or dextrose. The pH can be adjusted with an acid or a base, such as hydrochloric acid or sodium hydroxide. The parenteral formulation can be packaged in ampoules, disposable syringes or multiple dose vials made of glass or plastic.

Pharmaceutical compositions suitable for injectable use include sterile aqueous solutions (herein water-soluble) or dispersions and sterile powders for the immediate preparation of sterile injectable solutions or dispersions. For intravenous administration, suitable pharmaceutically acceptable carriers include physiological saline, bacteriostatic water, Cremophor EL™ (BASF, Parsippany, N.J.) or phosphate buffered saline (PBS). In all cases, the composition must be sterile, and should be fluid to the extent that easy syringeability exists. It should be stable under the conditions of manufacture and storage and must be able to prevent the contamination effect of microorganisms such as bacteria and fungus. The carrier can be a solvent or dispersion medium containing, for example, water, ethanol, polyol (for example, glycerol, propylene glycol, and liquid polyethylene glycol, etc.), and suitable mixtures thereof. For example, by using coatings such as lecithin, maintaining the desired particle size in the case of dispersions, and using surfactants, suitable fluidity can be maintained. Prevention of the action of microorganisms can be achieved by various antibacterial and antifungal agents, such as parabens, chlorobutanol, phenol, ascorbic acid, thimerosal, and the like. In many cases, it may be preferable to include isotonic agents, for example, sugars, polyalcohols (such as mannitol, sorbitol), sodium chloride in the composition. Prolonged absorption of the compositions for injection can be achieved by including in the composition the agents that delays absorption, such as aluminum monostearate and gelatin.

Sterile injectable solution can be prepared by incorporating the antibody or antibodies in the required amount into a suitable solvent having one or a combination of the ingredients enumerated above (as required), followed by filtered sterilization. Generally, dispersions are prepared by incorporating the antibody or antibodies into a sterile carrier containing a basic dispersion medium and the required other ingredients from those enumerated above. As far as the sterile powders used for the preparation of sterile injectable solutions, the methods of preparation are vacuum drying and freeze-drying to obtain powders containing active ingredients and any additional desired ingredients, from a sterile filtered solution of the above ingredients.

For administration by inhalation, the compound is delivered in the form of aerosol spray from a pressurized container or dispenser or nebulizer containing a suitable propellant, such as carbon dioxide and other gas.

Systemic administration can also be performed by transmucosal or transdermal means. For transmucosal or transdermal administration, penetrants suitable for penetrating the barrier are used in the formulation. Such penetrants are generally known in the art, and include, for example, detergents, bile salts, and fusidic acid derivatives for transmucosal administration. Transmucosal administration can be achieved through the use of nasal sprays or suppositories. For transdermal administration, one or more of the antibodies can be formulated into plaster, ointment, gel, or cream as generally known in the art.

The compounds may also be prepared in the form of suppositories (for example, with conventional suppository bases such as cocoa butter or other glycerides) or retention enemas for rectal delivery.

In one embodiment, the antibodies can be prepared with a carrier that prevents the antibodies from being rapidly eliminated by the body, such as a sustained release/controlled release formulation, including implants and microencapsulated delivery systems. Biodegradable and biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

It is especially advantageous to formulate parenteral compositions in the form of dosage unit for ease of administration and uniformity of dosage. As used herein, the form of dosage unit refers to a physically separable unit suitable as a unitary dosage for the subjects to be treated; each unit contains one or more of the antibodies in a predetermined amount calculated to produce the desired therapeutic effect in combination with the required pharmaceutical carrier. The specifications of the form of dosage unit of the embodiment are indicated by and directly dependent on: the unique characteristics of the antibodies and the specific therapeutic effect to be achieved, and the intrinsic limitations in the art of formulating such antibodies for the treatment of individuals.

The pharmaceutical composition can be placed in a container, package, or dispenser together with instructions for administration.

The formulations described herein may also contain more than one of the antibodies, depending on the specific indication to be treated, preferably those with complementary activities but not negatively affecting each other. Alternatively, or in addition, the composition may comprise, for example, an agent that enhances the function thereof, such as a cytotoxic agent, cytokine, chemotherapeutic agent, or growth inhibitory agent. Such molecules are suitably present in combination in an effective amount for the intended purpose. For example, they can be present in combination in the kit or be present in combination in use.

In one embodiment, one or more of the antibodies can be administered in a combination therapy, i.e., in combination with other agents such as therapeutic agents (which can be used to treat pathological conditions or disorders, such as various forms of cancer, autoimmune disorders, and inflammatory diseases). The term "in combination with" as used herein refers to administrating agents substantially simultaneously, simultaneously, or sequentially. If being administered sequentially, when the second compound initially administered, the first compounds of the two compounds is still preferably detected at an effective concentration at the treatment site. In one case, "in combination with" can also mean that the antibody and other therapeutic agents of the present disclosure are included together in the kit.

For example, a combination therapy may comprise one or more antibodies described herein that are co-formulated and/or co-administered with one or more additional therapeutic agents (e.g., one or more inhibitors for cytokines and growth factors, immunosuppressants, anti-inflammatory agents, metabolic inhibitors, enzyme inhibitors, and/or cytotoxins or cytostatic agents, as described in more detail below). Such combination therapies can advantageously utilize the administered therapeutic agents in lower doses, thus avoiding possible toxicities or complications associated with various monotherapies.

For the purpose of clarity and concise description, features are described herein as part of the same or separate embodiments. However, it will be understood that the scope of the present disclosure may include some embodiments having combinations of all or some of the features described.

EMBODIMENTS

Example 1: Preparation of Monoclonal Antibody Against Claudin 18.2

Multiple strategies have been applied to immunize Balb/c mice and screen simultaneously to obtain monoclonal antibodies which only specifically bind to Claudin 18.2 and not to Claudin 18.1, an alternatively spliced isoform. Detailed description is as follows:
1) Construction of Stably Transfected Cell Line of Claudin 18.2

The plasmid Claudin 18.1-puc57-Amp containing the full-length sequence of human Claudin 18.1 (UniProtKB-P56856) was synthesized (Suzhou Hongxun Biotech, SynbioTech). By using this plasmid as a template, the upstream primer 5'-ttggcaaagaattgctagatgtccaccaccacatgcc-3' and the downstream primer 5'-tgttcgggccctcctcgattacacat-agtcgtgcttgg-3' were used in PCR to amplify the full-length fragment of human Claudin 18.1 (Met1-Val261). After the amplified product is enzymatically linked with NEBuilder HiFi DNA Assembly Master Mix (NEB, Cat: M0530L), then it was cloned into the eukaryotic expression plasmid system. In a similar way, the plasmid Claudin 18.2-puc57-Amp containing the full-length sequence of human Claudin 18.2 (UniProtKB-P56856-2) was synthesized (Suzhou Hongxun Biotechnology, SynbioTech). By using this plasmid as a template, the upstream primer 5'-ttggcaaagaattgcta-gatggccgtgactgcctgtc-3' and the downstream primer 5'-tgttcgggccctcctcgattacacatagtcgtgcttgg-3' were used in PCR to amplify the full-length fragment of human Claudin 18.2 (Met1-Val261). After the amplified product is enzymatically linked with NEBuilder HiFi DNA Assembly Master Mix (NEB, Cat: M0530L), then it was cloned into the eukaryotic expression plasmid system. NIH3T3 and HEK293 cells were electrotransfected by this plasmid, respectively, and 1-10 µg/mL Puromycin (Gibco, Cat: A1113803) was used for screening the stable expression cell lines under a gradual increase selection pressure.

Figure 1:
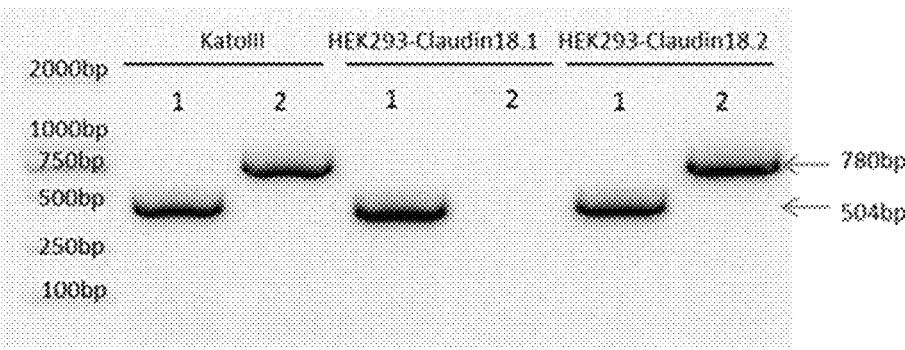
FIG. 1: RT-PCR shows that the stably transfected HEK293 cell lines expresses Claudin 18.1 and Claudin 18.2, respectively. Both the stably transfected cell line of HEK293-Claudin 18.2 and the control KATO III cells can amplify specifically the characteristic 780 bp band of Claudin 18.2, while HEK293-Claudin 18.1 can only amplify the 504 bp common fragment.

The obtained HEK293-Claudin 18.1 and HEK293-Claudin 18.2 stably transfected cell lines were first verified by RT-PCR. Trizol RNA extraction kit was used to extract total RNA from positive cloned cells, and reverse transcription kit (SuperScript™ First-Strand Synthesis System, Cat: 18080051) was used to reverse transcription to obtain a cDNA library by using Oligo (dT) primers. Because of the two splicing isoforms of Claudin, Claudin 18.1 and Claudin 18.2 are different from the N-terminal to the first extracellular domain (Loop1), primers KNB14 (5'-tgtgcgccac-catggccgtg-3') and primers KNB15 (5'-tggaaggataagat-tgtacc-3') are designed, which can amplify the region from Loop1 to the C-terminal of Claudin 18.1 and Claudin 18.2 (504 bp); the primer KNB16 (5'-tgggtgccattggcctcctg-3') is designed to specifically and complementary bind to the N-terminal of Claudin 18.2, not bind to the N-terminal of Claudin 18.1, only amplify the full length fragment (780 bp) from the N-terminal to the C-terminal of Claudin 18.2, using KATO III cells (ATCC HTB-103) expressing Claudin 18.2 as a positive control. The results are shown in FIG. 1. RT-PCR shows that the HEK293 stably transfected cell line expresses Claudin 18.1 and Claudin 18.2, respectively. Both the HEK293-Claudin 18.2 stably transfected cell line and the control KATO III cells can amplify the Claudin 18.2 specific 780 bp characteristic stripe, while HEK293-Claudin 18.1 can only amplify the common 504 bp fragment.

The constructed stably transfected cell line HEK293-Claudin 18.2 cells and NIH3T3-Claudin 18.2 cells were digested and collected, washed twice with PBS, and 100 µL of 1:200 diluted primary anti-rabbit antibody against Claudin 18.2 (Abcam, EPR19202, catalog number: ab222512) was added to each tube, incubated at 4° C. for 60 minutes, and washed away the excess primary antibody solution with 0.5% BSA/PBS, and then added 50 µL of secondary goat-anti-rabbit antibody IgGFc-AF647 (Jackson ImmunoResearch, catalog number: 111-606-046), incubated at 4° C. for 45 minutes, then washed away the excess secondary antibody with 0.5% BSA/PBS, and finally resuspended the cells with 100 µL PBS solution. The mixtures were immediately detected on the flow cytometer. The results are shown in FIG. 2 and FIG. 3.

Figure 2:
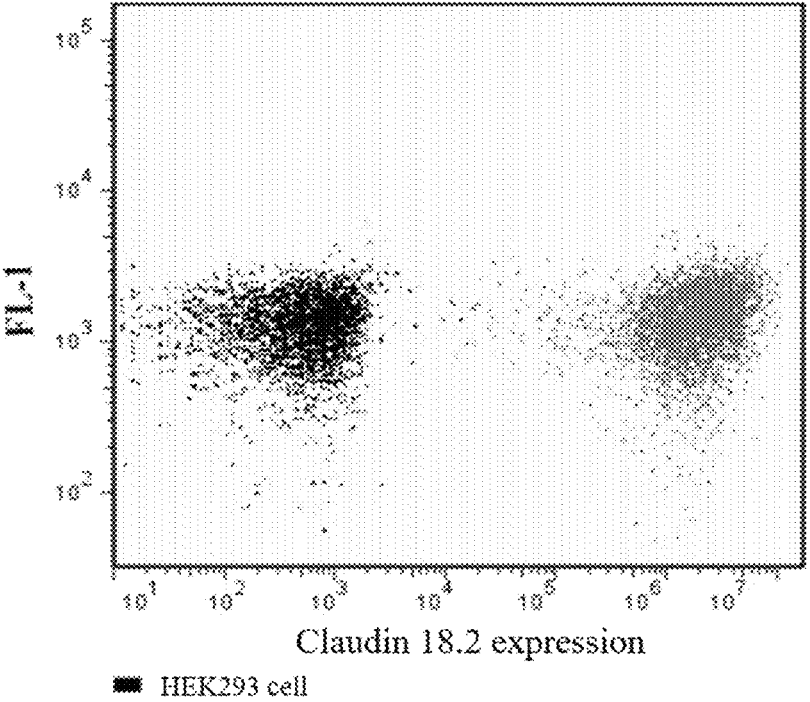
FIG. 2 shows the results of the FACS experiment screening the high-expressing stably transfected cell line of HEK293-Claudin 18.2. In which the black dot is the negative control, and the gray dot is the high-expressing stably transfected cell line of HEK293-Claudin 18.2.

FIG. 2 shows the results of detecting the HEK293-Claudin 18.2 stably transfected cell line which is transfected with the Claudin 18.2 full-length gene by FACS experiment. The black dots therein are untransfected HEK293 cells, the gray dots therein are the HEK293-Claudin 18.2 stably transfected cell line, HEK293 cells do not express Claudin 18.2, and the HEK293-Claudin 18.2 stably transfected cell line highly expresses Claudin 18.2 on the surface of cell membrane.

Figure 3:
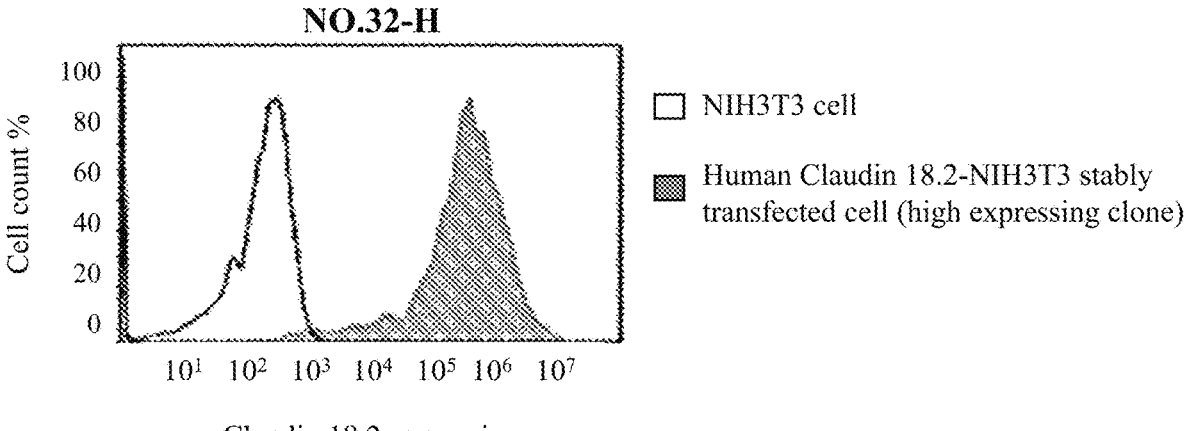
FIG. 3 shows the results of the FACS experiment screening the high-expressing stably transfected cell line of NIH3T3-Claudin 18.2. In which the black line is the negative control, and the gray shadow is the stably transfected cell line of 3T3-Claudin 18.2. NO. 32-H is a high-expressing stably transfected cell line of 3T3-Claudin 18.2, NO. 18-M is a medium-expressing stably transfected cell line of 3T3-
Figure 3:
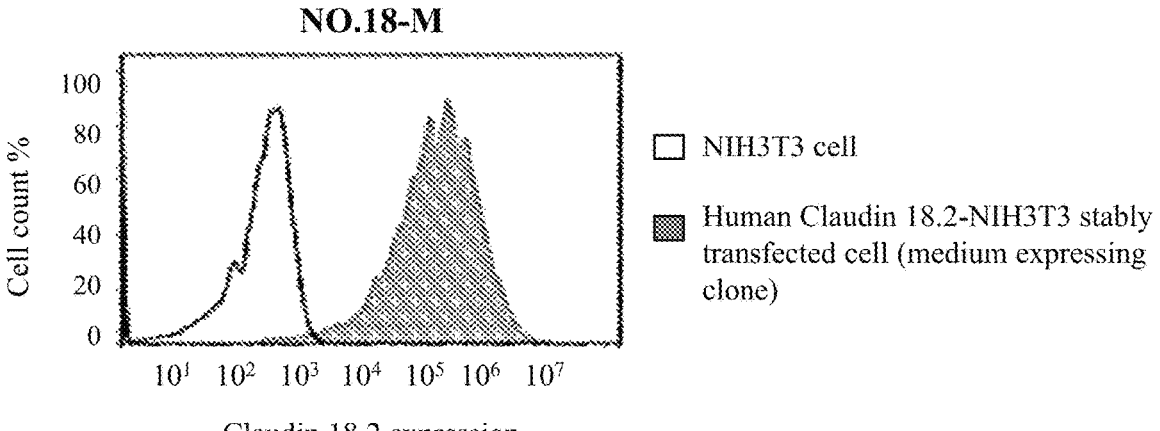
Figure 3:
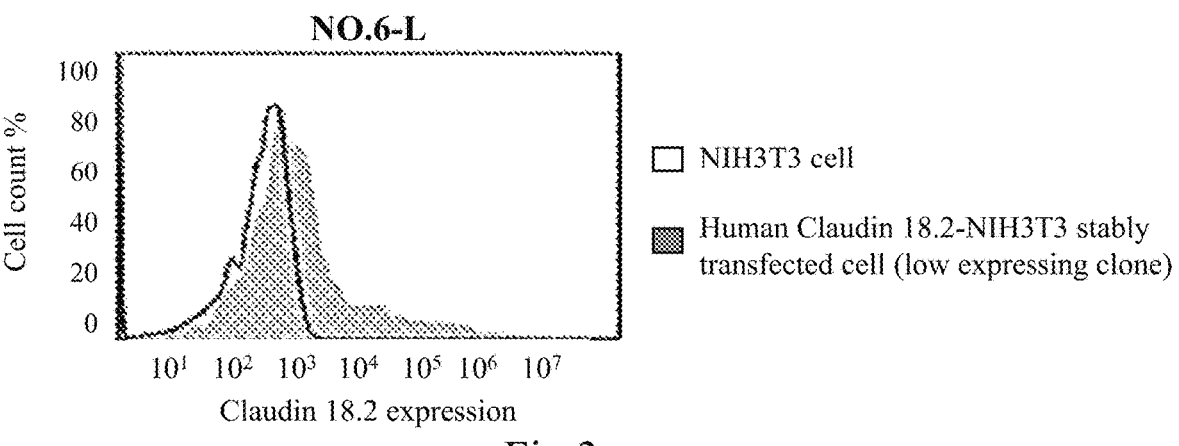

FIG. 3 shows the results of detecting the high expression of Claudin 18.2 in the NIH3T3-Claudin 18.2 stably transfected cell line by FACS experiment. The black line therein is the negative control, and the gray shading is the 3T3-Claudin 18.2 stably transfected cell line. NO. 32-H is the 3T3-Claudin 18.2 stably transfected cell line which high expressed Claudin 18.2, NO. 18-M is the 3T3-Claudin 18.2 stably transfected cell line which medium expressed Claudin 18.2, NO. 6-L is the 3T3-Claudin 18.2 stably transfected cell line which low expressed Claudin 18.2.

The amplified positive stably transfected cell line was collected and stored frozen, and the NIH3T3-Claudin 18.2 stable cell line therein was used to immunize animals.

2) Preparation of Monoclonal Antibodies Against Claudin 18.2 from Hybridomas

The female Balb/c mice of 6-8 weeks were taken, and immunized with 3T3-Claudin 18.2 stable transfected cells or the plasmid encoding Claudin 18.2, respectively, or alternately. When using cells for immunization, $1 \times 10^6$ 3T3-Claudin 18.2 stable transfected cells were taken and mixed with Freund's adjuvant or non-Freund's adjuvant each time, and then injected to the roots of the thighs and the foot pads and immunized again at different parts two weeks later. When using DNA for immunization, 20 μg of plasmid was taken and mixed with 1 μg of CpG, then the mixture was directly injected into the abdomen of mice by using a gene gun (Biorad) 40 psi, and immunized once a week. Three days before the preparation of fusion, HEK293-Claudin 18.2 stably transfected cell line which highly expressed Claudin 18.2 was used in $1 \times 10^6$ cells/50 μL/head for tail vein challenging immunization. The mice were sacrificed after three days, the popliteal lymph nodes, inguinal lymph nodes, and iliac lymph nodes were collected and ground in DMEM to obtain the suspension rich B cells; the spleens of mice were taken out, ground in DMEM and centrifuged to obtain the spleen cell suspension. An appropriate amount of suspension of lymph node and spleen cell was taken and mixed with SP2/0, then the cell fusion was performed on electrofusion instrument.

3) Construction of Anti-Claudin 18.2 Phage Antibody Library

Part of the collected suspensions of spleens and peripheral lymph node cells of mice were extracted total RNA by Trizol RNA extraction kit, and reverse transcription kit (Super-Script First-Strand Synthesis System, Catalog No. 18080051) was used to obtain light and heavy chains' cDNA libraries of antibodies respectively by using the reverse transcription of light and heavy chain specific primers. Using this cDNA as a template, the light and heavy chain variable region primers were used to amplify the light and heavy chain variable region fragments of antibodies, which were digested and cloned into a phage plasmid vectors containing human antibody light chain constant region Ckappa or human IgG1 heavy chain constant region CH1 respectively, formed a light chain library and a heavy chain library of chimera. The antibody fragments in the light chain library were digested with BspQI and SfiI, and then ligated into the heavy chain library to form a mouse chimeric Fab phage display library based on filamentous phage M13, with a library size of $1.2 \times 10^{10}$. 0.8 mL phage (titer about $1 \times 10^{13}/$ mL) was taken and mixed with 200 μL 5% BSA/PBS, then $1 \times 10^7$ HEK293-Claudin 18.1 cells were added, ice bath for 1 hour; centrifuge at 1000 rpm for 10 minutes, the supernatant was collected, and mixed the supernatant with $1 \times 10^6$ HEK293-Claudin 18.2 cells, ice bath for 1 hour, centrifuged at 1000 rpm for 3 minutes, discarded the supernatant; 1 mL of 1% BSA/PBS was added, washed for 5-10 times; 1 mL of 100 mM TEA (triethylamine) was added to lyse the cells for 10 minutes at room temperature, 0.5 mL of 1M Tris-HCl, pH 7.5 was added to neutralize, 10 mL of TG1 E. coli. cells at logarithmic growth phase was infected and maintained at 37° C. for 30 minutes. According to the conventional molecular biology process, the phage is rescued, the titer is detected, and the next round of panning is carried out.

Example 2. Screening and Sequence Acquisition of Specific Antibodies Against Claudin 18.2

HEK293-Claudin 18.1, HEK293-Claudin 18.2 and HEK293 alive cells were pre-stained with 5 μM, 0.5 μM and 0 μM Cell Tracker Green CMFDA Dye (Thermo, Catalog No. C2925) respectively according to the instructions. After washing away the dye, the cells were mixed in 1:1:1, added to 96-well plate ($2 \times 10^5$ cells/well), and bound with hybridoma supernatant or bacterial induction supernatant. After incubating for 1 hour in ice bath, AlexaFluro647-labeled anti-mouse IgG Fc or anti-human IgG F(ab)'2 secondary antibody (Jackson ImmunoResearch) was added, incubated on ice for 45 minutes. After washing, 100 μL PBS to each well was added to resuspend the cells, a flow cytometer (iQue Screener) was used for gating the three different cell populations according to the difference of fluorescence intensity of the FL2 channel, and then the binding among the antibodies to be tested and each cell population was detected by FL4 channel. The antibodies screened were bound to HEK293-Claudin 18.2 stable transfected cells with high affinity and specificity, while not bound to HEK293-Claudin 18.1 stable transfected cells and HEK293 cells. From the hybridoma cells, through FACS detection, a total of 320 clones that could bind to Claudin 18.2 but not to Claudin 18.1 were screened; after 3 rounds of panning, 62 clones bind to Claudin 18.2 with high affinity but not to Claudin 18.1 from the phage Fab library were screened.

The positive clones screened from the phage library were used for plasmid extraction and sequencing, and the variable region sequences were cloned into vectors containing heavy chain and light chain constant region for full-length IgG expression. From the positive cells obtained from the hybridomas, 1 mL of TRNzol was added for lysis, and total RNA was extracted by the guanidine isothiocyanate method. Using the total RNA as a template, after synthesizing the first-strand cDNA, the first-strand cDNA is used as a subsequent template to amplify the variable region DNA sequence corresponding to the hybridoma cells. After sequencing the amplified products, the candidate variable region sequences of hybridoma heavy chain and light chain are obtained (as below).

```
Clone 8C11: SEQ ID NOs: 1-10
heavy chain VH
<----------FR1----------> CDR1     <----FR2-----> 	       CDR2
QVQLQQSGAELVKPGASVKLSCKASGYTFTTTFGINWVRQRPEQGLEWIGWIFPGDGSIKYNEKFKG
<-------------FR3-------------> CDR3     <---FR4--->
KATLTTDKSSSTAYMQISSLTSEDSAVYFCARFYYGNSFVSWGQGTLVTVSA
    Nucleic acid sequence
  CAGGTTCAGCTGCAGCAGTCTGGAGCTGAACTGGTAAAGCCTGGGGCTTCAGTGAAGTTGTCCTGC
AAGGCTTCTGGCTACACATTCACAACTTTTGGTATAAACTGGGTGAGGCAGAGGTGAACAGGGACTT
GAATGGATTGGATGGATTTTTCCTGGAGATGGTAGTATTAAGTACAATGAGAAGTTCAAGGGCAAGGCC
ACACTGACTACAGACAAATCCTCCAGTACAGCCTACATGCAGATCAGCAGTTTGACATCTGAGGACTCG
GCTGTCTATTTCTGTGCAAGGTTCTACTATGGTAACTCCTTTGTTTCCTGGGGCCAAGGGACTCTGGTC
ACTGTCTCTGCA
    light chain
```

-continued

```
          <----------FR1--------->       CDR1        <----FR2------> CDR2 <----
      DIVMTQSPSSLAVTAGEKVTMTCKSSQSLLNSGNQKNYLTWYQQRPGQPPKLLLYWASTRESGVPDR
      ----------FR3------------->   CDR3   <--FR4--->
      FTGSGSGTDFALTITSVQAEDLAVYYQNDYTYPFTFGSGTKLEIK
          Nucleic acid sequence of light chain
          GACATTGTGATGACACAGTCTCCATCCTCCCTGGCTGTGACTGCAGGAGAGAAGGTCACTATGACC
      TGCAAGTCCAGTCAGAGTCTCGTTAAACAGTGGAAATCAAAAGAACTACTTGACCTGGTACCAACAGAGA
      CCAGGGCAGCCTCCTAAACTTTTGCTCTACTGGGCATCCACTAGGGAATCTGGGGTCCCTGATCGCTTC
      ACAGGCAGTGGATCTGGAACAGATTTCGCTCTCACCATCACCAGTGTGCAGGCTGAAGACCTGGCAGTT
      TATTACTGTCAGAATGATTATACTTATCCATTCACGTTCGGCTCGGGGACAAAGTTGGAAATAAAA Clone 9A8 : SEQ ID NOs: 11-20
          heavy chain
          <----------FR1---------->  CDR1  <----FR2------>       CDR2
      QVQLQQSGREWRPGTSVKVSCKPSGYAFTNYLIDWVKQRPGQGLEWIGGINPGSGDTVYNEKFKA
      <-------------FR3-------------->  CDR3  <---FR4--->
      KATLTADKSSMTANMQLSSLTSDDSAVYFCARRVRGNSFDSWGQGTLVTVSA
          Nucleic acid sequence of heavy chain
          CAGGTCCAGCTGCAGCAGTCTGGACGTGAGGTGGTAAGGCCTGGGACTTCAGTGAAGGTGTCCTGC
      AAGCCTTCTGGATACGCCTTCACTAATTACTTGATAGACTGGGTAAAACAGAGGCCTGGACAGGGCCTT
      GAGTGGATTGGAGGGATTAATCCTGGAAGTGGTGACACTGTGTACAATGAGAAGTTCAAGGCCAAGGCA
      ACACTGACTGCAGACAAATCCTCCATGACTGCCAACATGCAGCTCAGCAGCCTGACATCTGATGACTCT
      GCGGTCTATTTCTGCGCAAGAAGGGTCCGTGGTAATTCGTTTGATTCCTGGGGCCAAGGGACTCTGGTC
      ACTGTCTCTGCA
          light chain
          <----------FR1--------->       CDR1          <-----FR2----> CDR2 <---
      DIQMTQSPSSLTVTAGEKVTMSCKSSQSLLNSGNQRNYLTWYQQKTGQPPKLLIYWASTRESGVPD
      --------FR3--------------->   CDR3   <--FR4--->
      RFTGSGSGTDFTLTINSVQAEDLAVYYQNNYYYPLTFGAGTKLEIK
          Nucleic acid sequence
          GACATTCAGATGACCCAGTCTCCATCCTCCCTGACTGTGACAGCAGGAGAGAAGGTCACTATGAGC
      TGCAAGTCCAGTCAGAGTCTCGTTAAACAGTGGAAATCAAAGGAACTACTTGACCTGGTACCAGCAGAAA
      ACAGGGCAGCCTCCTAAACTGTTGATCTACTGGGCATCCACTAGGGAATCTGGGGTCCCTGATCGCTTC
      ACAGGCAGTGGATCTGGAACTGATTTCACTCTCACCATCAACAGTGTGCAGGCTGAAGACCTGGCAGTT
      TATTACTGTCAGAATAATTATTATTATCCGCTCACGTTCGGTGCTGGGACCAAGCTGGAAATAAAA Clone 9C9 : SEQ ID NOs: 21-30
          heavy chain
          <-----------FR1--------->  CDR1   <-----FR2---->       CDR2        <
      EVQLKESGPGLVAPSQSLSITCTVSGFSLTNYGVSWIRQPPGKGLEWLGAIWAGGNTNYNSALMSR
      --------------FR3-------------->   CDR3   <---FR4--->
      LSIRKDNSKSQVFLKMNSLQTDDTAMYYCARVGYGNSFANWGQGTLVTVSA
          Nucleic acid sequence of heavy chain
          GAGGTCCAGCTGAAGGAGTCAGGACCTGGCCTGGTGGCGCCCTCACAGAGCCTGTCCATCACTTGC
      ACTGTCTCTGGGTTTTCATTGACCAACTATGGTGTTTCCTGGATTCGCCAGCCTCCAGGAAAGGGTCTG
      GAGTGGCTGGGAGCAATATGGGCTGGTGGAAACACAAATTATAATTCGGCTCTCATGTCCAGACTGAGC
      ATCAGGAAAGACAATTCCAAGAGCCAAGTTTTTCTTAAAAATGAACAGTCTCCAAACTGATGACACAGCC
      ATGTACTACTGTGCCAGAGTAGGGTATGGTAACTCGTTTGCTAACTGGGGCCAAGGGACTCTGGTCACT
      GTCTCTGCAG
          light chain
          <-----------FR1--------->       CDR1          <-----FR2-----> CDR2 <---
      DIVMTQSPSSLTVTAGEKVTLSCKSSQTLLNSGNQKNYLTWYQQKPGQPPKLLIYWASTRESGVPD
      -----------FR3-------------->   CDR3   <--FR4--->
      RFTGSGSGTDFTLTISSVQAEDLAVYYQNNYFYPLTFGAGTRLEIK
          Nucleic acid sequence of light chain
          GACATTGTGATGACACAGTCTCCATCCTCCCTGACTGTGACAGCAGGAGAGAAGGTCACTCTGAGC
      TGCAAGTCCAGTCAGACTCTCGTTAAACAGTGGAAATCAAAAGAACTACTTGACGTGGTACCAGCAGAAA
      CCAGGGCAGCCTCCTAAACTGTTGATCTACTGGGCATCCACTAGGGAATCTGGGGTCCCTGATCGCTTC
      ACAGGCAGTGGATCTGGAACAGATTTCACTCTCACCATCAGCAGCGTGCAGGCTGAAGACCTGGCAGTT
      TATTACTGTCAGAATAATTATTTTTATCCGCTCACGTTCGGTGCTGGGACCAGACTGGAAATAAAA Clone 9D12 : SEQ ID NOs: 31-40
          heavy chain
          <-----------FR1--------->  CDR1   <-----FR2---->       CDR2
      EVQLQQSGREWRPGTSVKVSCKPSGYAFTNYLIDWVKQRPGQGLEWIGGINPGSGDTVYNERFKD
      <-------------FR3-------------->   CDR3   <---FR4--->
      KATLTADKSSSSANMQLSSLTSDDSAVYFCARRVRGNSFDSWGQGTLVTVSA
          Nucleic acid sequence of heavy chain
          GAGGTCCAGCTGCAGCAGTCTGGACGTGAGGTGGTAAGGCCTGGGACTTCAGTGAAGGTGTCCTGC
      AAGCCTTCTGGATACGCCTTCACTAATTACTTGATAGACTGGGTAAAACAGAGGCCTGGACAGGGCCTT
      GAGTGGATTGGAGGGATTAATCCTGGAAGTGGTGACACTGTGTACAATGAGAGGTTCAAGGACAAGGCA
      ACACTGACTGCAGACAAATCCTCCAGCTCTGCCAACATGCAGCTCAGCAGCCTGACATCTGATGACTCT
      GCGGTCTATTTCTGCGCAAGAAGGGTCCGTGGTAATTCGTTTGATTCCTGGGGCCAAGGGACTCTGGTC
      ACTGTCTCTGCA
          light chain
          <----------FR1--------->       CDR1          <-----FR2-----> CDR2 <---
      DIVMTQSPSSLTVTAGQKVTMSCKSSQSLLNSGNQKNYLTWYQQKPGQPPKLLIYWASTRESGVPD
      ----------FR3-------------->   CDR3   <--FR4-->
      RFTGSGSGKDFTLTISSVQAEDLAVFYQNNYFYPLTFGAGTKLELK
          Nucleic acid sequence of light chain
          GACATTGTGATGACTCAGTCTCCATCCTCCCTAACTGTGACAGCAGGACAGAAGGTCACTATGAGC
```

-continued

```
TGCAAGTCCAGTCAGAGTCTGTTAAACAGTGGAAATCAAAAGAACTACTTGACCTGGTACCAGCAGAAA
CCGGGGCAGCCTCCTAAACTGTTGATCTACTGGGCATCCACTAGGGAATCTGGGGTCCCTGATCGCTTC
ACAGGCAGTGGGTCTGGAAAAGATTTCACTCTCACCATCAGCAGTGTGCAGGCTGAAGACCTGGCAGTT
TTTTACTGTCAGAATAATTATTTTTATCCGCTCACGTTCGGTGCTGGGACCAAGCTGGAGCTGAAA
```

Clone 13A8 : SEQ ID NOs: 41-50
    heavy chain
    <----------FR1---------> CDR1     <-----FR2---->      CDR2       <
    EVKLVESGGGLVRPGGSLKVSCAASGITFSRYAISWVRQTPEKRLEWVATISSGDSYTYYLDSVKG
    -----------------FR3-----------> CDR3    <---FR4--->
    RFTISRDDAKNTLYLQMSSLRSEDTAMYYCGRLGYGNAMDYWGQGTSVTVSS
    Nucleic acid sequence of heavy chain
```
   GAGGTGAAGCTGGTGGAGTCTGGGGGAGGCTTAGTGAGGCCTGGAGGGTCCCTGAAAGTGTCCTGT
GCAGCCTCTGGAATCACTTTCAGTCGCTATGCCATATCTTGGGTTCGCCAGACTCCGGAGAAGAGGCTG
GAGTGGGTCGCAACTATTAGTAGCGGTGATAGTTACACCTACTATTTGGACAGTGTGAAGGGGCGATTC
ACCATCTCCAGAGACGATGCCAAGAACACCCTGTATCTGCAAATGAGCAGTCTGAGGTCTGAGGACACG
GCCATGTATTACTGTGGAAGACTGGGGTATGGTAATGCTATGGACTACTGGGGTCAAGGAACCTCAGTC
ACCGTCTCCTCA
```
    light chain
    <----------FR1-------->      CDR1      <-----FR2-----> CDR2    <
    NIMMTQSPSSLTVTAGEKVTMSKSSQSLLNSGNQKNYLTWYQQKPGQPPKLLIYWASTRESGVPD --
    ---------FR3------------->   CDR3   <--FR4----->
    RFTGSGSGTDFTLTISSVQAEDLAVYYQNDYSYPLTFGAGTKLEIK
    Nucleic acid sequence of light chain
```
   AACATTATGATGACACAGTCTCCATCCTCCCTGACTGTGACAGCAGGAGAGAAGGTCACTATGAGC
TGCAAGTCCAGTCAGAGTCTGTTAAACAGTGGAAATCAAAAGAACTACTTGACCTGGTACCAGCAGAAA
CCAGGGCAGCCTCCTAAACTGTTGATCTACTGGGCATCCACTAGGGAATCTGGGGTCCCTGATCGCTTC
ACAGGCAGTGGATCTGGAACAGATTTCACTCTCACCATCAGCAGTGTGCAGGCTGAAGACCTGGCAGTT
TATTACTGTCAGAATGATTATAGTTATCCTCTCACGTTCGGTGCTGGGACCAAGCTGGAAATCAAA
```

Clone 14H11 : SEQ ID NOs: 51-60
    heavy chain
    <----------FR1---------> CDR1     <-----FR2---->      CDR2       <
    EVQLVESGGGLVKPGGSLKLSCAVSGFTINNYGMSWVRQTPEKRLEWVATIIGGGSSTYYPDSLKG
    -----------FR3---------------> CDR3    <---FR4--->
    RFTISRDNAKNNLYLQMSSLRSEDTALYYCVRLYFGNSFAYWGQGTLVTVSA
    Nucleic acid sequence of heavy chain
```
   GAGGTGCAGCTGGTGGAGTCTGGGGGAGGCTTAGTGAAGCCTGGAGGGTCCCTGAAACTCTCCTGT
GCAGTCTCTGGATTCACTATCAATAACTATGGCATGTCTTGGGTTCGCCAGACTCCGGAGAAGAGGCTG
GAGTGGGTCGCAACCATTATTGGTGGTGGTAGTTCCACCTACTATCCTGACAGTTTGAAGGGGCGATTC
ACCATCTCCAGAGACAATGCCAAGAACAACCTGTACCTGCAAATGAGCAGTCTGAGGTCTGAGGACACG
GCCTTGTATTACTGTGTAAGACTCTACTTTGGTAACTCCTTTGCTTACTGGGGCCAAGGGACTCTGGTC
ACTGTCTCTGCA
```
    light chain
    <----------FR1-------->      CDR1      <-----FR2-----> CDR2  <---
    DIVMTQSPSSLTVTAGEKVTVSKSSQSLSNSGNQRNYLTWYQQKPGQPPKLLIYWASTRESGVPD
    -----------FR3------------->   CDR3   <--FR4--->
    RFTGSGSGTDFTLTISSVQAEDLAVYYQNNYFYPLTFGAGTKLELK
    Nucleic acid sequence of light chain
```
   GACATTGTGATGACTCAGTCTCCATCCTCTCTGACTGTGACAGCAGGAGAGAAGGTCACTGTGAGC
TGCAAGTCCAGTCAGAGTCTGTCAAACAGTGGAAATCAAAGGAACTACTTGACCTGGTACCAGCAGAAA
CCAGGGCAGCCTCCTAAACTGTTGATCTACTGGGCATCCACTAGGGAATCTGGGGTCCCTGATCGCTTC
ACAGGCAGTGGATCTGGAACAGATTTCACTCTCACCATCAGCAGTGTGCAGGCTGAAGACCTGGCAGTT
TATTACTGTCAGAATAATTATTTTTATCCGCTCACGTTCGGTGCTGGGACCAAGCTGGAGCTGAAA
```

Clone 15A7 : SEQ ID NOs: 61-70
    heavy chain
    <----------FR1---------> CDR1     <-----FR2---->      CDR2       <
    QVQLQQSGAELVKPGYSVKLSCKASGYTFTNFGINWVRQRPEKGLEWIGWIFPGDGTTKYNENFKG
    --------------FR3--------------> CDR3   <---FR4--->
    KATLTTDKSSSTAYMQLSRLTSEDSAVYFCARFYYGNSFVNWGQGTLVTVSA
    Nucleic acid sequence of heavy chain
```
   CAGGTTCAGCTGCAACAGTCTGGAGCTGAACTGGTCAAGCCTGGGTATTCAGTGAAGTTGTCCTGC
AAGGCTTCTGGCTACACCTTCACAAATTTTGGTATAAACTGGGTGAGGCAGAGGCCTGAAAAGGGACTT
GAGTGGATTGGATGGATTTTTCCTGGAGATGGCACTACTAAATACAATGAGAACTTCAAGGGTAAGGCC
ACACTGACAACAGACAAATCCTCCAGCACAGCCTACATGCAGCTCAGCAGGCTGACATCTGAAGACTCT
GCTGTCTATTTCTGTGCAAGGTTCTACTACGGTAACTCCTTTGTTAACTGGGGCCAAGGGACTCTGGTC
ACTGTCTCTGCAG
```
    light chain
    <----------FR1-------->      CDR1      <-----FR2-----> CDR2  <---
    DIVMTQSPSSLTVTAGEKVTLSCKSSQTLLNSGNQKNYLTWYQQKPGQPPKLLIHWASTRESGVPD
    -----------FR3-------------> CDR3   <--FR4--->
    RFTGSGSGTDFTLTISSVQAEDLAVYYQNNYFYPLTFGAGTKLEIK
    Nucleic acid sequence of light chain
```
   GACATTGTGATGACACAGTCTCCATCCTCCCTGACTGTGACAGCAGGAGAGAAGGTCACTCTGAGC
TGCAAGTCCAGTCAGACTCTGTTAAACAGTGGAAATCAAAAGAACTACTTGACGTGGTACCAGCAGAAA
CCGGGGCAGCCTCCTAAACTGTTGATCCACTGGGCATCCACTAGGGAATCTGGGGTCCCTGATCGCTTC
ACAGGCAGTGGATCTGGAACAGATTTCACTCTCACCATCAGCAGTGTGCAGGCTGAAGACCTGGCAGTT
TATTACTGTCAGAATAATTATTTTTATCCGCTCACGTTCGGTGCTGGGACCAAGCTGGAAATCAAA
```

-continued

```
    Clone 15D11 : SEQ ID NOs: 71-80
    heavy chain
    <----------FR1---------> CDR1    <-----FR2----->    CDR2        <
    QVQLQQSGPGLVAPSQSLSITCTVSGFSLTNYGVSWIRQPPGKGLEWLGAIWAGGNTNYNSALMSR
    -----------FR3--------------->   CDR3   <---FR4--->
    LSIRKDNSKSQVFLKMNSLQTDDTAMYYCARVGYGNSFANWGQGTLVTVSA
    Nucleic acid sequence of heavy chain
    CAGGTCCAGCTGCAGCAGTCAGGACCTGGCCTGGTGGCGCCCTCACAGAGCCTGTCCATCACTTGC
    ACTGTCTCTGGGTTTTCATTGACCAACTATGGTGTTTCCTGGATTCGCCAGCCTCCAGGAAAGGGTCTG
    GAGTGGCTGGGAGCAATATGGGCTGGTGGAAACACAAATTATAATTCGGCTCTCATGTCCAGACTGAGC
    ATCAGGAAAGACAATTCCAAGAGCCAAGTTTTCTTAAAAATGAACAGTCTCCAAACTGATGACACAGCC
    ATGTACTACTGTGCCAGAGTAGGGTATGGTAACTCGTTTGCTAACTGGGGGCCAAGGGACTCTGGTCACT
    GTCTCTGCA
    light chain
    <---------FR1-------->       CDR1          <-----FR2-----> CDR2 <---
    DIVMTQSPSSLTVTAGEKVTMSCKSSQSLLNSGNLRNYLTWYQQKPGRPPKLLIYWASTRESGVPD
    -----------FR3-------------->  CDR3    <--FR4--->
    RFTGSGSGTDFTLTISSVQAEDLAVYYCQNNYFYPLTFGAGTKLELK
    Nucleic acid sequence of light chain
    GACATTGTGATGACACAGTCTCCATCCTCCCTGACTGTGACAGCAGGAGAGAAGGTCACTATGAGC
    TGCAAGTCCAGTCAGAGTCTGTTAAACAGTGGAAATCTAAGGAACTACTTGACCTGGTACCAGCAGAAA
    CCAGGGCGGCCTCCTAAACTGTTGATCTACTGGGCATCCACTAGGGAATCTGGGGTCCCTGATCGCTTC
    ACAGGCAGTGGATCTGGGACAGATTTCACTCTCACCATCAGCAGTGTGCAGGCTGAAGACCTGGCAGTT
    TATTACTGTCAGAATAATTATTTTTATCCGCTCACGTTCGGTGCTGGGACCAAGCTGGAGCTGAAA Clone 15F9 : SEQ ID NOs: 81-90
    heavy chain
    <----------FR1---------> CDR1    <-----FR2----->    CDR2        <
    EIQLVQSGPELKKPGETVKISCKASGYTFTNYGINWVKQAPGKGLKWMGWINPNTGETTYAEEFKG
    --------------FR3-------------->   CDR3   <---FR4--->
    RFALSWKTSASTAYLQINNLKNEDTATYFCARLYYGNRFDYWGQGTTLTVSS
    Nucleic acid sequence of heavy chain
    GAGATCCAGTTGGTGCAGTCTGGACCTGAGCTGAAGAAGCCTGGAGAGACAGTCAAGATCTCCTGC
    AAGGCTTCTGGATATACCTTTACAAACTATGGAATAAACTGGGTGAAGCAGGCTCCAGGAAAGGGTTTA
    AAGTGGATGGGCTGGATAAACCCCAACACTGGAGAAACAACATATGCTGAAGAGTTCAAGGGACGGTTT
    GCCCTCTCTTGGAAAACCTCTGCCAGCACTGCCTATTTGCAGATCAACAACCTCAAAAATGAGGACACG
    GCTACATATTTCTGTGCAAGACTCTACTATGGTAATCGATTTGACTACTGGGGCCAAGGCACCACTCTC
    ACAGTCTCCTCA
    light chain
    <---------FR1-------->       CDR1          <-----FR2-----> CDR2 <---
    DIVMTQSPSSLTVTAGEKVTMSCKSSQSLLNSGNQRNYLTWYQQKPGQPPKLLIYWASTRESGVPD
    -----------FR3-------------->  CDR3    <--FR4--->
    RFTGSGSGTDFTLTISSVQAEDLAVYYCQNAYYYPLTFGAGTKLEIK
    Nucleic acid sequence of light chain
    GACATTGTGATGACACAGTCTCCCTCCTCCCTGACTGTGACAGCAGGAGAGAAGGTCACTATGAGC
    TGCAAGTCCAGTCAGAGTCTTATTAAACAGTGGAAATCAAAGGAACTATTTGACCTGGTACCAGCAGAAG
    CCAGGGCAGCCTCCTAAACTATTGATCTACTGGGCATCCACTAGGGAATCTGGGGTCCCTGATCGCTTC
    ACAGGCAGTGGATCTGGAACAGATTTCACTCTCACCATCAGCAGTGTGCAGGCTGAAGACCTGGCAGTT
    TATTACTGTCAGAATGCTTATTATTATCCGCTCACGTTCGGTGCTGGGACCAAGCTGGAAATCAAA Clone 18A9 : SEQ ID NOs: 91-100
    heavy chain
    <----------FR1---------> CDR1    <-----FR2----->    CDR2        <
    QVQLQQSGREVVRPGTSVKVSCKPSGYAFTNYLIDWVKQRPGQGLEWIGGINPGSGDTVYNEKFKA
    --------------FR3-------------->   CDR3   <---FR4--->
    KATLTADKSSMTANMQLSSLTSDDSAVYFCARRVRGNSGDSWGQGTLVTVSA
    Nucleic acid sequence of nucleic acid sequence
    CAGGTGCAGCTGCAGCAGTCTGGACGTGAGGTGGTAAGGCCTGGGACTTCAGTGAAGGTGTCCTGC
    AAGCCTTCTGGATACGCCTTCACTAATTACTTGATAGACTGGGTAAAACAGAGGCCTGGACAGGGCCTT
    GAGTGGATTGGAGGGATTAATCCTGGAAGTGGTGACACTGTGTACAATGGAAAGTTCAAGGGCCAAGGCA
    ACACTGACTGCAGACAAATCCTCCATGACTGCCAACATGCAGCTCAGCAGCCTGACATCTGATGACTCT
    GCGGTCTATTTCTGCGCAAGAAGGGTCCGTGGTAATTCGTTTGATTCCTGGGGCCAAGGGACTCTGGTC
    ACTGTCTCTGCA
    light chain
    <---------FR1-------->       CDR1          <-----FR2------> CDR2 <---
    DIVMSQSPSSLTVTAGEKVTMSCKSSQSLLNSGNQKNYLTWYQQKPGQPPKLLIYWASTRESGVPD
    -----------FR3-------------->  CDR3    <--FR4--->
    RFTGSGSGKDFTLTISSVQAEDLALYYCQNNYFYPLTFGAGTKLELK
    Nucleic acid sequence of light chain
    GACATTGTGATGTCACAGTCTCCATCCTCCCTGACTGTGACAGCAGGAGAGAAGGTCACTATGAGC
    TGCAAGTCCAGTCAGAGTCTGTTAAACAGTGGAAATCAAAAGAACTACTTGACCTGGTACCAGCAGAAA
    CCAGGGCAGCCTCCTAAATTGTTGATCTACTGGGCATCCACTAGGGAATCTGGGGTCCCTGATCGCTTC
    ACAGGCAGTGGATCTGGAAAAGATTTCACTCTCACCATCAGCAGTGTGCAGGCTGAAGACCTGGCACTT
    TATTACTGTCAGAATAATTATTTTTATCCGCTCACGTTCGGTGCTGGGACCAAGCTGGAGCTGAAA
```

-continued

```
    Clone 18G5 : SEQ ID NOs: 101-110
    heavy chain
    <----------FR1---------> CDR1    <-----FR2----->     CDR2       <
EVQLQQSGREWRPGTSVKVSCKPSGYAFTNYLIDWVKQRPGQGLEWIGGINPGSGDTVYNEKFKA
--------------FR3--------------->   CDR3   <---FR4--->
KATLTADKSSMTTNMQLSSLTSDDSAVYFCARRVRGNSFDSWGQGTLVTVSA
    Nucleic acid sequence of heavy chain
    GAGGTCCAGCTGCAGCAGTCTGGACGTGAGGTGGTAAGGCCTGGGACTTCAGTGAAGGTGTCCTGC
AAGCCTTCTGGATACGCCTTCACTAATTACTTGATAGACTGGGTAAAACAGAGGCCTGGACAGGGCCTT
GAGTGGATTGGAGGGATTAATCCTGGAAGTGGTGACACTGTGTACAATGAGAAGTTCAAGGCCAAGGCA
ACACTGACTGCAGACAAATCCTCCATGACTACCAACATGCAGCTCAGCAGCCTGACATCTGATGACTCT
GCGGTCTATTTCTGCGCAAGAAGGGTCCGTGGTAATTCGTTTGATTCCTGGGGCCAAGGGACTCTGGTC
ACTGTCTCTGCA
    light chain
    <----------FR1--------->      CDR1      <-----FR2-----> CDR2  <---
DIVMTQSPSSLTVRAGEKVTMTCKSSQSLFNSGNQRNYLTWYQQKPGQPPKLLLYWATARESGVPD
-----------FR3------------->   CDR3   <--FR4--->
RFTGSGSGTDFTLSISSVQAEDLAVYYCQNVYFYPLTFGAGTKLEIK
    Nucleic acid sequence of light chain
    GACATTGTGATGACACAGTCTCCATCCTCCCTGACTGTGAGAGCAGGAGAGAAGGTCACTATGACC
TGCAAGTCCAGTCAGAGTCTGTTTAACAGTGGAAATCAAAGGAACTACTTGACCTGGTACCAGCAGAAA
CCAGGGCAGCCTCCTAAACTTTTGCTCTACTGGGCAACCGCTAGGGAATCTGGGGTCCCTGATCGCTTC
ACAGGCAGTGGTTCTGGAACAGATTTCACTCTCTCCATCAGCAGTGTGCAGGCTGAAGACCTGGCAGTT
TATTACTGTCAGAATGTTTATTTTTATCCGCTCACGTTCGGTGCTGGGACCAAGCTGGAAATAAAA Clone 18D10 : SEQ ID NOs: 111-120
    heavy chain
    <----------FR1----------->   CDR1   <----FR2----->    CDR2
DVQLQESGPGLVKPSQSLSLTCTVTGYSITSNYAWNWIRQFPGNKLEWMGYINYSGNTNYNPSLKS
<-------------FR3------------->  CDR3   <---FR4--->
RISITRDTSKNQFFLQLNSVTAEDTATYYCATSYYGNSFIYWGQGTLVTVSA
    Nucleic acid sequence of heavy chain
    GATGTGCAGCTTCAGGAGTCGGGACCTGGCCTGGTGAAACCTTCTCAGTCTCTGTCCCTCACCTGC
ACTGTCACTGGCTACTCAATCACCAGTAATTATGCCTGGAACTGGATCCGACAGTTTCCAGGAAACAAA
CTAGAGTGGATGGGCTACATAAACTACAGTGGGAACACTAACTATAACCCATCTCTCAAAAGTGAATC
TCTATCACTCGAGACACATCCAAGAACCAGTTCTTCCTGCAGTTGAATTCTGTGACTGCTGAGGACACA
GCCACATATTATTGTGCAACCTCCTATTATGGTAATTCCTTTATTTACTGGGGCCAAGGGACTCTGGTC
ACTGTCTCTGCA
    light chain
    <----------FR1--------->      CDR1      <-----FR2-----> CDR2   <---
DIVMTQSPSSLTVTAGEKVTMSCKSSQSLLNSGNQKNYLTWYQQKPGQPPKLLIYWASTRESGVPD
-----------FR3------------->   CDR3   <--FR4--->
RFTGSGSGTDFTLTISSVQAEDLAVYYCQNAYSFPWTFGGGTKLEIK
    Nucleic acid sequence of light chain
    GACATTGTGATGACACAGTCTCCATCCTCCCTGACTGTGACAGCAGGAGAGAAGGTCACTATGAGC
TGCAAGTCCAGTCAGAGTCTGTTAAACAGTGGAAATCAAAAGAACTACTTGACCTGGTACCAGCAGAAA
CCAGGGCAGCCTCCTAAACTGTTGATCTACTGGGCATCCACTAGGGAGTCTGGGGTCCCTGATCGCTTC
ACAGGCAGTGGATCTGGAACAGATTTCACTCTCACCATCAGCAGTGTGCAGGCTGAAGACCTGGCAGTT
TATTACTGTCAGAATGCTTATAGTTTTCCGTGGACGTTCGGTGGAGGCACCAAGCTGGAAATCAAA Clone 19B2 : SEQ ID NOs:  121-130
    heavy chain
    <----------FR1--------->  CDR1    <-----FR2---->      CDR2        <
QVQLQQSGAELVKPGTSVKLSCKASGYSFTTYGLNWVRQRPKQGLEWIGWIFPGDGNVYNEKFQG
---------------FR3------------->  CDR3    <FR4>
QATLTTDKSSSTAYMQLSRLTSEDSAVYFCARFYYGNSLNYWGQGTLVTVSA
    Nucleic acid sequence of heavy chain
    CAGGTCCAGCTGCAGCAGTCTGGAGCTGAACTGGTAAAGCCTGGGACTTCAGTGAAGTTGTCCTGC
AAGGCTTCTGGCTACTCCTTCACAACCTATGGTCTAAACTGGGTGAGGCAGAGGCCTAAACAGGGACTT
GAGTGGATTGGATGGATTTTCCCTGGAGATGGTAATGTTAACTACAATGAGAAATTCAGGGCCAGGCC
ACACTGACTACAGACAAATCCTCCAGCACAGCCTACATGCAGCTCAGCAGGCTGACATCTGAGGACTCT
GCTGTCTATTTCTGTGCAAGGTTTTATTACGGTAACTCCTTAAATTACTGGGGCCAAGGGACTCTGGTC
ACTGTCTCTGCA
    light chain
    <----------FR1--------->      CDR1       <-----FR2-----> CDR2  <---
DIVMTQSPSSLTVTAGEKVTMSCKSSQSLLNSGNLRNYLTWYQQKPGRPPKLLIYWASTRESGVPD
-----------FR3------------->   CDR3   <--FR4--->
RFTGSGSGTDFTLTISSVQAEDLAVYYCQNNYFYPLTFGAGTKLEIK
    Nucleic acid sequence of light chain
    GACATTGTGATGACCCAGTCTCCATCCTCCCTGACTGTGACAGCAGGAGAGAAGGTCACTATGAGC
TGCAAGTCCAGTCAGAGTCTGTTAAACAGTGGAAATCTAAGGAACTACTTGACCTGGTACCAGCAGAAA
CCAGGGCGGCCTCCTAAACTGTTGATCTACTGGGCATCCACTAGGGAATCTGGGGTCCCTGATCGCTTC
ACAGGCAGTGGATCTGGAACAGATTTCACTCTCACCATCAGCAGTGTGCAGGCTGAAGACCTGGCAGTT
TATTACTGTCAGAATAATTATTTTTATCCGCTCACGTTCGGTGCTGGGACCAAGCTGGAAATCAAA Clone 25A5 : SEQ ID NOs: 131-140
    heavy chain
    <----------FR1--------->  CDR1    <-----FR2----->      CDR2          <
EVQLKESGPGLVAPSQSLSITCTVSGFSLTNYGVSWIRQPPGKGLEWLGAIWAGGNTNYNSALMSR
-----------FR3--------------->   CDR3   <-----FR4--->
```

```
                               -continued
LSIRKDNSKSQVFLKMNSLQTDDTAMYYCARVGYGNSFANWGQGTLVTVSA
     Nucleic acid sequence of heavy chain
     GAGGTCCAGCTGAAGGAGTCAGGACCTGGCCTGGTGGCGCCCTCACAGAGCCTGTCCATCACTTGC
ACTGTCTCTGGGTTTTCATTGACCAACTATGGTGTTTCCTGGATTCGCCAGCCTCCAGGAAAGGGTCTG
GAGTGGCTGGGAGCAATATGGGCTGGTGGAAACACAAATTATAATTCGGCTCTCATGTCCAGACTGAGC
ATCAGGAAAGACAATTCCAAGAGCCAAGTTTTCTTAAAAATGAACAGTCTCCAAACTGATGACACAGCC
ATGTACTACTGTGCCAGAGTAGGGTATGGTAACTCGTTTGCTAACTGGGGCCAAGGGACTCTGGTCACT
GTCTCTGCA
     light chain
     <----------FR1-------->        CDR1        <-----FR2-----> CDR2   <---
     DIVMTQSPSSLTVTAGEKVTMSCKSSQSLLNSGNQRNYLTWYQQKPGQPPKLLIYWASTRESGIPD
------------FR3-------------->  CDR3      <---FR4--->
RFIGSGSGTDFTLTISSVQAEDVSVYYCQNNYIFPLTFGAGTKLEIK
     Nucleic acid sequence of light chain
     GACATTGTGATGACACAGTCTCCATCCTCCCTGACTGTGACAGCAGGAGAGAAGGTCACTATGAGC
TGCAAGTCCAGTCAGAGTCTGTTAAACAGTGGAAATCAAAGGAACTACTTGACCTGGTACCAGCAGAAA
CCAGGGCAGCCTCCTAAACTGTTGATCTACTGGGCATCCACTAGGGAATCTGGGATCCCTGATCGCTTC
ATAGGCAGTGGATCTGGAACAGATTTCACTCTCACCATCAGCAGTGTGCAGGCTGAAGACGTGTCAGTT
TATTACTGTCAGAATAATTATATTTTTCCTCTCACGTTCGGTGCTGGGACCAAGCTGGAAATCAAA Clone 25F5 : SEQ ID NOs:  141-150
     heavy chain
     <----------FR1--------->  CDR1       <-----FR2---->         CDR2        <
     QVQLKQSGAELVKPGASLKLSCKASGYTFTTYGINVVRQRPEQGLEWIGWIFPGDATTMYNEKFKG
--------------FR3-------------->  CDR3    <---FR4--->
TATLTADKSSSTAYMQLSGLTSEDSAVYFCARFYYGNSFVDWGQGTLVTVSA
     Nucleic acid sequence of heavy chain
     CAGGTCCAGCTGAAGCAGTCTGGAGCTGAACTGGTCAAGCCTGGGGCTTCACTCAAGTTGTCCTGC
AAGGCTTCTGGCTACACCTTCACAACTTATGGTATAAACTGGGTGAGGCAGAGGCCTGAACAGGGACTT
GAGTGGATTGGATGGATTTTTCCTGGAGATGCAACCACTATGTACAATGAGAAATTCAAGGGCACGGCC
ACACTGACTGCAGACAAATCCTCCAGTACAGCCTACATGCAGCTCAGCGGGTTGACATCTGAGGACTCT
GCTGTCTATTTCTGTGCAAGGTTCTACTACGGTAACTCCTTTGTTGACTGGGGCCAAGGGACTCTGGTC
ACTGTCTCTGCA
     light chain
     <----------FR1-------->        CDR1        <-----FR2-----> CDR2    <---
     DIVMTQSPSSLTVTAGEKVTMSCKSSQSLLNSGNQKNYLTWYQQKPGQPPKLLIYWASTRESGVPD
------------FR3-------------->  CDR3      <---FR4--->
RFTGSGSGTDFTLTISSVQAEDLAVYYCQNAYYYPLTFGAGTKLEIK
     Nucleic acid sequence of light chain
     GACATTGTGATGACACAGTCTCCATCCTCCCTGACTGTGACAGCAGGAGAGAAGGTCACTATGAGC
TGCAAGTCCAGTCAGAGTCTGTTAAACAGTGGAAATCAAAAGAACTACTTGACCTGGTACCAGCAGAAG
CCAGGGCAGCCTCCTAAACTGTTGATCTACTGGGCATCCACTAGGGAATCTGGGGTCCCTGATCGCTTC
ACAGGCAGTGGATCTGGAACAGATTTCACTCTCACCATCAGCAGTGTGCAGGCTGAAGACCTGGCAGTT
TATTACTGTCAGAATGCTTATTATTATCCGCTCACGTTCGGTGCTGGGACCAAGCTGGAAATCAAA
```

The sequence fragments of the above heavy chain and light chain variable region were amplified by PCR, and the heavy chain variable region was cloned into the vector containing the human heavy chain constant region to express the complete IgG1 heavy chain in mammalian cells. Similarly, the light chain variable region was cloned into the vector containing the human light chain constant region to express the complete kappa light chain in mammalian cells. After correct sequencing, it was transfected into HEK293-6E mammalian cells, IgG1 was expressed and secreted into the culture medium, and the supernatant was combined and collected, purified after being filtered. The IgG was purified by Protein A chromatography, the culture supernatant was loaded on the Protein A column with suitable size, washed with 50 mM Tris-HCl pH8.0, 250 mM NaCl, and the bound IgG was eluted with 0.1M Glycine-HCl, pH3.0. The protein was ultrafiltered and concentrated by using a concentration tube (Millipore), OD280 was detected, and the concentration of IgG was determined by spectrophotometry. SDS-PAGE was used to analyze the purity of IgG.

The HEK293-Claudin 18.1 cells, HEK293-Claudin 18.2 cells and HEK293 cells at logarithmic growth phase were taken, after digesting, added at $5\times10^4$ cells/100 μL to the U-shaped 96-well plate, centrifuged at 1100 rpm for 3 minutes, the supernatant was discarded, the cells were gently patted and loosed, 50 μL of antibody diluted according to the series was added to each well (antibody concentration starts from 100 nM, 5 times dilution in 8 series), and incubate at 4° C. for 1 hour. After the incubation, 140 μL 0.5% BSA was added to each well to wash 3 times, the secondary antibody AlexaFluro647 anti-human IgG (Jackson ImmunoResearch, catalog number: 109-606-170) was added with 30 μL/well, and incubated at 4° C. for 40 minutes. After the incubation, 140 μL 0.5% BSA was added to each well to wash 3 times, and finally resuspended each well with 50 μL PBS for flow cytometry (iQue Screener) detection. The results are shown in FIG. 4 and Table 1. The flow cytometry (FACS) results of FIG. 4 showed that the obtained chimeric Claudin 18.2 IgG1 antibody only recognized the HEK293-Claudin 18.2 cells transfected with Claudin 18.2 (FIG. 4B), did not bind to HEK293 (FIG. 4A) and HEK293-claudin 18.1 (FIG. 4C).

TABLE 1

The Binding of Claudin 18.2 Antibody to Stable Transfected Cell Lines (N.B. No binding detected)

| mAb | Claudin 18.2 EC50 (nM) | Claudin 18.1 EC50 (nM) | HEK293 EC50 (nM) |
|---|---|---|---|
| 8C11 | 0.23 | N.B. | N.B. |
| 9A8 | 0.21 | N.B. | N.B. |
| 9C9 | 1.46 | N.B. | N.B. |
| 9D12 | 6.78 | N.B. | N.B. |
| 13A8 | 0.25 | N.B. | N.B. |
| 14H11 | 0.22 | N.B. | N.B. |
| 15A7 | 0.59 | N.B. | N.B. |
| 15D11 | 0.21 | N.B. | N.B. |
| 15F9 | 0.17 | N.B. | N.B. |
| 18A9 | 0.31 | N.B. | N.B. |
| 18G5 | 3.79 | N.B. | N.B. |

TABLE 1-continued

The Binding of Claudin 18.2 Antibody to Stable Transfected
Cell Lines (N.B. No binding detected)

| mAb | Claudin 18.2 EC50 (nM) | Claudin 18.1 EC50 (nM) | HEK293 EC50 (nM) |
|---|---|---|---|
| 18D10 | 0.37 | N.B. | N.B. |
| 19B2 | 0.20 | N.B. | N.B. |
| 25A5 | 0.19 | N.B. | N.B. |
| 25F5 | 2.14 | N.B. | N.B. |

Example 3. Endocytosis Experiment of Antibody

The cells at logarithmic growth phase were taken, washed once with pre-warmed medium, centrifuged at 1000 rpm for 3 minutes, the supernatant was discarded, serum-free medium was added to resuspend the cells to $1\times10^6$ cells/mL; the cells were pipetted into an EP tube (200 μL/tube), pre-cooled 500 μL 0.5% BSA/PBS was added, centrifuged at 1000 rpm for 3 minutes, the supernatant was discarded, 10 μg/mL antibody was added, and incubated at 37° C. for 15 minutes, 30 minutes, 60 minutes, 120 minutes, 180 minutes, and 240 minutes, after the primary antibody incubation at each time point is over, pre-cooling 500 μL of 0.5% BSA/PBS was added to wash twice, then the secondary antibody which was diluted at 1:300 was directly added and incubated for 45 minutes. After the incubation of secondary antibody, the cells were washed twice with 500 μL 0.5% BSA/PBS, and resuspended to 200 μL for FACS detection. The results are shown in FIG. 5. Antibodies such as 15D11, 15F9, 18A9 and 18D10 have the function of mediating cell endocytosis.

Example 4. Humanization of the Antibody Against Claudin 18.2

The selected variable region sequence of monoclonal antibody was aligned with the human germline antibody sequence, to find the sequence with high homology for CDRs grafting; then in silico homology modeling was performed, at the same time, amino acid sequences of the CDR region and its surrounding framework were analyzed, the form of their spatial stereoscopic combination was investigated. By calculating electrostatic force, van der Waals force, hydrophilicity, and entropy value, the key amino acid residues that may interact with the target and maintain the spatial framework in positive monoclonal antibody gene sequence were analyzed, and reverse mutation sites were designed on this basis. The affinity of HLA-DRs were analyzed and investigated to select human embryonic framework sequences with lower immunogenicity. Amino acid residues that may be modified during fermentation were analyzed, and mutations were designed to reduce the possibility of modification.

Different heavy chain derivatives and light chain derivatives were designed and obtained. After the light and heavy chain derivatives were respectively synthesized in full sequence, they were cloned into the vectors containing Ckappa of antibody kappa chain constant region or CH1-CH3 of human IgG1 constant region, the light and heavy chain derivative plasmids derived from the same maternal source were combined and matched, transfected into HEK293.6E cells for expression for 5-6 days, and the supernatant was collected and purified by Protein A column. The variable region sequence of the humanized antibody is as follows:

```
15F9VHv5 : SEQ ID NOs: 151-155
<----------FR1---------> CDR1   <-----FR2----->      CDR2        <
QIQLVQSGSELKKPGASVKVSCKASGYTFTNYGINWVRQAPGQGLEWMGWINPNTGETTYAEGFTG
---------------FR3-------------> CDR3   <---FR4--->
RFVLSWDTSVSTAYLQISSLKAEDTAVYFCARLYYGNRFDSWGQGTLVTVSS
    Nucleic acid sequence
    CAGATTCAGCTGGTGCAGTCTGGCAGCGAGCTGAAGAAACCTGGCGCCTCTGTGAAGGTGTCCTGC
AAGGCTAGCGGCTACACATTCACCAACTACGGCATCAACTGGGTCCGACAGGCTCCTGGACAGGGACTC
GAATGGATGGGCTGGATCAACCCCAACACCGGCGAGACAACATACGCCGAGGGCTTCACAGGCAGATTC
GTGCTGAGCTGGGATACCAGCGTCAGCACAGCTTACCTGCAGATCAGCAGCCTGAAGGCCGAGGATACC
GCCGTGTACTTCTGCGCCAGACTGTACTACGGCAACAGATTCGACTCTTGGGGCCAGGGCACACTGGTC
ACAGTCTCTTCT 15F9VHv5r1 : SEQ ID NOs:  156-160
<----------FR1---------> CDR1   <-----FR2----->      CDR2        <
QVQLVQSGSELKKPGASVKVSCKASGYTFTNYGINWVRQAPGQGLEWMGWINPNTGETTYAEEFKG
--------------FR3--------------> CDR3   <---FR4--->
RFVFSLDTSVSTAYLQISSLKAEDTAVYFCARLYYGNRFDSWGQGTLVTVSS
    Nucleic acid sequence
    CAGGTGCAGCTGGTGCAGTCTGGCAGCGAGCTGAAGAAACCTGGCGCCTCTGTGAAGGTGTCCTGC
AAGGCTAGCGGCTACACATTCACCAACTACGGCATCAACTGGGTCCGACAGGCTCCTGGACAGGGACTC
GAATGGATGGGCTGGATCAACCCCAACACCGGCGAGACAACATACGCCGAGGAGTTCAAGGGCAGATTC
GTGTTCAGCCTGGATACCAGCGTCAGCACAGCTTACCTGCAGATCAGCAGCCTGAAGGCCGAGGATACC
GCCGTGTACTTCTGCGCCAGACTGTACTACGGCAACAGATTCGACTCTTGGGGCCAGGGCACACTGGTC
ACAGTCTCTTCT 15F9VHv5r2 : SEQ ID NOs: 161-165
<----------FR1---------> CDR1   <-----FR2----->      CDR2        <
EVQLVQSGSELKKPGASVKVSCKASGYTFTNYGINWVRQAPGQGLEWMGWINPYTGETTYAEEFKG
--------------FR3--------------> CDR3   <---FR4--->
RFVFSLDTSVSTAYLQISSLKAEDTAVYFCARLYYGNRFDSWGQGTLVTVSS
    Nucleic acid sequence
    GAGGTGCAGCTGGTGCAGTCTGGCAGCGAGCTGAAGAAACCTGGCGCCTCTGTGAAGGTGTCCTGC
AAGGCTAGCGGCTACACATTCACCAACTACGGCATCAACTGGGTCCGACAGGCTCCTGGACAGGGACTC
GAATGGATGGGCTGGATCAACCCCTACACCGGCGAGACAACATACGCCGAGGAGTTCAAGGGCAGATTC
GTGTTCAGCCTGGATACCAGCGTCAGCACAGCTTACCTGCAGATCAGCAGCCTGAAGGCCGAGGATACC
GCCGTGTACTTCTGCGCCAGACTGTACTACGGCAACAGATTCGACTCTTGGGGCCAGGGCACACTGGTC
ACAGTCTCTTCT
```

-continued

```
    15F9VHv6 : SEQ ID NOs: 166-170
    <----------FR1---------> CDR1      <-----FR2----->      CDR2          <
    QIQLVQSGSELKKPGASVKVSCKASGYTFTNYGINWVRQAPGQGLEWMGWINPGTGETTYAEGFTG
    --------------FR3--------------->  CDR3      <---FR4--->
    RFVLSWDTSVSTAYLQISSLKAEDTAVYFCARLYYGNRFDSWGQGTLVTVSS
       Nucleic acid sequence
    CAGATTCAGCTGGTGCAGTCTGGCAGCGAGCTGAAGAAACCTGGCGCCTCTGTGAAGGTGTCCTGC
    AAGGCTAGCGGCTACACATTCACCAACTACGGCATCAACTGGGTCCGACAGGCTCCTGGACAGGGACTC
    GAATGGATGGGCTGGATCAACCCCGGCACCGGCGAGACAACATACGCCGAGGGCTTCACAGGCGAGGATTC
    GTGCTGAGCTGGGATACCAGCGtCAGCACAGCTTACCTGCAGATCaGcGCCTGAAGGCCGAGGATACC
    GCCGTGTACTTCTGCGCCAGACTGTACTACGGCAACAGATTCGACTCTTGGGGCCAGGGCACACTGGTC
    ACAGTCTCTTCT
```

```
    18A9VHv1 : SEQ ID NOs: 171-175
    <----------FR1---------> CDR1      <-----FR2----->      CDR2          <
    QVQLVQSGAEVKKPGSSVKVSCKPSGYAFTNYLIDWVRQAPGQGLEWMGGINPGSGDTVYNEKFQG
    ----------------FR3------------->  CDR3      <---FR4--->
    RVTLTADKSSMTAYMELSSLRSEDTAVYFCARRVRGNSFDSWGQGTLVTVSS
       Nucleic acid sequence
    CAGGTTCAGCTGGTTCAGTCTGGCGCCGAAGTGAAGAAACCTGGCAGCAGCGTGAAGGTGTCCTGC
    AAGCCTTCTGGCTACGCCTTCACCAACTACCTGATCGACTGGGTCCGACAGGCTCCTGGACAGGGACTT
    GAATGGATGGGCGGCATCAACCCTGGCAGCGGCGATACAGTGTATAACGAGAAGTTCCAGGGCAGAGTG
    ACCCTGACCGCCGACAAGTCTAGCATGACCGCCTACATGGAACTGAGCAGCCTGAGAAGCGAGGATACC
    GCCGTGTACTTCTGTGCCAGAAGAGTGCGGGGCAACAGCTTCGATTCTTGGGGCCAGGGAACCCTGGTC
    ACCGTTTCTTCT
```

```
    18A9VHv2 : SEQ ID NOs: 176-180
    <----------FR1---------> CDR1      <-----FR2----->      CDR2          <
    QVQLVQSGAEVKKPGSSVKVSCKPSGYTFTNYLIDWVRQAPGQGLEWMGGINPGSGDTVYNEKFQG
    ----------------FR3------------->  CDR3      <---FR4--->
    RVTLTADESTSTAYMELSSLRSEDTAVYFCARRVRGNSFDSWGQGTLVTVSS
       Nucleic acid sequence
    CAGGTTCAGCTGGTTCAGTCTGGCGCCGAAGTGAAGAAACCTGGCAGCAGCGTGAAGGTGTCCTGC
    AAGCCTTCTGGCTACACCTTCACCAACTACCTGATCGACTGGGTCCGACAGGCTCCTGGACAGGGACTT
    GAATGGATGGGCGGCATCAACCCTGGCAGCGGCGATACAGTGTACAACGAGAAGTTCCAGGGCAGAGTG
    ACCCTGACCGCCGACGAGTCTACCAGCACCGCCTACATGGAACTGAGCAGCCTGAGAAGCGAGGATACC
    GCCGTGTACTTCTGTGCCAGAAGAGTGCGGGGCAACAGCTTCGATTCTTGGGGCCAGGGAACCCTGGTC
    ACCGTTTCTTCT
```

```
    18A9VHv3 : SEQ ID NOs: 181-185
    <----------FR1---------> CDR1      <-----FR2----->      CDR2          <
    QVQLVQSGAEVKKPGSSVKVSCKPSGYTFTNYLIDWVRQAPGQGLEWMGGINPGSGDTVYNEKFQG
    ----------------FR3------------->  CDR3      <---FR4--->
    RVTLTADKSSMTAYMELSSLRSEDTAVYYCARRVRGNSFDSWGQGTLVTVSS
       Nucleic acid sequence
    CAGGTTCAGCTGGTTCAGTCTGGCGCCGAAGTGAAGAAACCTGGCAGCAGCGTGAAGGTGTCCTGC
    AAGCCTTCTGGCTACACCTTCACCAACTACCTGATCGACTGGGTCCGACAGGCTCCTGGACAGGGACTT
    GAATGGATGGGCGGCATCAACCCTGGCAGCGGCGATACAGTGTACAACGAGAAGTTCCAGGGCAGAGTG
    ACCCTGACCGCCGACAAGTCTAGCATGACCGCCTACATGGAACTGAGCAGCCTGAGAAGCGAGGATACC
    GCCGTGTACTACTGTGCCAGAAGAGTGCGGGGCAACAGCTTCGATTCTTGGGGCCAGGGAACCCTGGTC
    ACCGTTTCTTCT
```

```
    18A9VHv4 : SEQ ID NOs: 186-190
    <----------FR1---------> CDR1      <-----FR2----->      CDR2          <
    QVQLVQSGAEVKKPGSSVKVSCKASGYTFTNYLIDWVRQAPGQGLEWMGGINPGSGDTVYNEKFQG
    ----------------FR3------------->  CDR3      <---FR4--->
    RVTLTADKSSMTAYMELSSLRSEDTAVYFCARRVRGNSFDSWGQGTLVTVSS
       Nucleic acid sequence
    CAGGTTCAGCTGGTTCAGTCTGGCGCCGAAGTGAAGAAACCTGGCAGCAGCGTGAAGGTGTCCTGC
    AAGGCTTCTGGCTACACCTTCACCAACTACCTGATCGACTGGGTCCGACAGGCTCCTGGACAGGGACTT
    GAATGGATGGGCGGCATCAACCCTGGCAGCGGCGATACAGTGTACAACGAGAAGTTCCAGGGCAGAGTG
    ACCCTGACCGCCGACAAGTCTAGCATGACCGCCTACATGGAACTGAGCAGCCTGAGAAGCGAGGATACC
    GCCGTGTACTTCTGTGCCAGAAGAGTGCGGGGCAACAGCTTCGATTCTTGGGGCCAGGGAACCCTGGTC
    ACCGTTTCTTCT
```

```
    18A9VHv5 : SEQ ID NOs: 191-195
    Amino acid sequence
    <----------FR1---------> CDR1      <-----FR2----->      CDR2          <
    QVQLVQSGAEVKKPGSSVKVSCKPSGYTFTNYLIDWVRQAPGQGLEWMGGINPGSGDTVYNEKFQG
    ----------------FR3------------->  CDR3      <---FR4--->
    RVTITADESTSTAYMELSSLRSEDTAVYFCARRVRGNSFDSWGQGTLVTVSS
       Nucleic acid sequence
    CAGGTTCAGCTGGTTCAGTCTGGCGCCGAAGTGAAGAAACCTGGCAGCAGCGTGAAGGTGTCCTGC
    AAGCCTTCTGGCTACACCTTCACCAACTACCTGATCGACTGGGTCCGACAGGCTCCTGGACAGGGACTT
    GAATGGATGGGCGGCATCAACCCTGGCAGCGGCGATACAGTGTACAACGAGAAGTTCCAGGGCAGAGTG
    ACCATCACCGCCGACGAGTCTACCAGCACCGCCTACATGGAACTGAGCAGCCTGAGAAGCGAGGATACC
    GCCGTGTACTTCTGTGCCAGAAGAGTGCGGGGCAACAGCTTCGATTCTTGGGGCCAGGGAACCCTGGTC
    ACCGTTTCTTCT
```

-continued

```
   18A9VHv6 : SEQ ID NOs: 196-200
   <-----------FR1---------> CDR1      <-----FR2---->      CDR2         <
   QVQLVQSGAEVKKPGASVKVSCKPSGYAFTNYLIDWVRQAPGQGLEWMGGINPGSGDTVYNEKFQG
   ----------------FR3------------->  CDR3    <---FR4--->
   RVTLTADKSSSTAYMELSSLRSEDTAVYFCARRVRGNSFDSWGQGTLVTVSS
      Nucleic acid sequence
   CAGGTTCAGCTGGTTCAGTCTGGCGCCGAAGTGAAGAAACCTGGCGCCAGCGTGAAGGTGTCCTGC
   AAGCCTTCTGGCTACGCCTTCACCAACTACCTGATCGACTGGGTCCGACAGGCTCCTGGACAGGGACTT
   GAATGGATGGGCGGCATCAACCCTGGCAGCGGCGATACAGTGTACAACGAGAAGTTCCAGGGCAGAGTG
   ACCCTGACCGCCGACAAGTCTAGCAGCACCGCCTACATGGAACTGAGCAGCCTGAGAAGCGAGGATACC
   GCCGTGTACTTCTGTGCCAGAAGAGTGCGGGGCAACAGCTTCGATTCTTGGGGCCAGGGAACCCTGGTC
   ACCGTTTCTTCT 18A9VHv7 : SEQ ID NOs: 201-205
   <-----------FR1---------> CDR1      <-----FR2---->      CDR2         <
   QVQLVQSGAEVKKPGASVKVSCKPSGYTFTNYLIDWVRQAPGQGLEWMGGINPGSGDTVYNEKFQG
   ----------------FR3------------->  CDR3    <---FR4--->
   RVTLTADTSTSTVYMELSSLRSEDTAVYFCARRVRGNSFDSWGQGTLVTVSS
      Nucleic acid sequence
   CAGGTTCAGCTGGTTCAGTCTGGCGCCGAAGTGAAGAAACCTGGCGCCAGCGTGAAGGTGTCCTGC
   AAGCCTTCTGGCTACACCTTCACCAACTACCTGATCGACTGGGTCCGACAGGCTCCTGGACAGGGACTT
   GAATGGATGGGCGGCATCAACCCTGGCAGCGGCGATACAGTGTACAACGAGAAGTTCCAGGGCAGAGTG
   ACCCTGACCGCCGACACCTCTACCAGCACCGTCTACATGGAACTGAGCAGCCTGAGAAGCGAGGATACC
   GCCGTGTACTTCTGTGCCAGAAGAGTGCGGGGCAACAGCTTCGATTCTTGGGGCCAGGGAACCCTGGTC
   ACCGTTTCTTCT 18D10VHv1 : SEQ ID NOs: 206-210
   <-----------FR1---------> CDR1      <-----FR2---->      CDR2
   QVQLQESGPGLVKPSETLSLTCTVSGYSITSNYAWNWIRQPPGKGLEWIGYINYSGNTNYNPSLKS
   <-------------FR3--------------> CDR3    <---FR4--->
   RVTISRDTSKNQFSLKLSSVTAADTAVYYCATSYYGNSFIYWGQGTLVTVSS
      Nucleic acid sequence
   CAGGTTCAGCTGCAAGAGTCTGGACCTGGCCTGGTCAAGCCTAGCGAGACACTGAGCCTGACCTGT
   ACCGTGTCCGGCTACAGCATCACCAGCAACTACGCCTGGAACTGGATCAGACAGCCTCCTGGCAAAGGC
   CTCGAGTGGATCGGCTACATCAACTACAGCGGCAACACCAACTACAACCCTAGCCTGAAGTCCAGAGTG
   ACCATCAGCAGAGACACCAGCAAGAACCAGTTCTCCCTGAAGCTGAGCAGCGTGACAGCCGCCGATACA
   GCCGTGTACTACTGTGCCACAAGCTACTACGGCAACAGCTTCATCTACTGGGGCCAGGGCACACTGGTC
   ACCGTTTCTTCT 18D10VHv2 : SEQ ID NOs: 211-215
   <-----------FR1---------> CDR1      <-----FR2---->      CDR2
   QVQLQESGPGLVKPSETLSLTCTVSGGSISSNYAWNWIRQPPGKGLEWMGYINYSGNTNYNPSLKS
   <-------------FR3--------------> CDR3    <---FR4--->
   RITISRDTSKNQFSLKLSSVTAADTAVYYCATSYYGNSFIYWGQGTLVTVSS
      Nucleic acid sequence
   CAGGTTCAGCTGCAAGAGTCTGGACCTGGCCTGGTCAAGCCTAGCGAGACACTGAGCCTGACCTGT
   ACCGTGTCCGGCGGCAGCATCAGCAGCAACTACGCCTGGAACTGGATCAGACAGCCTCCTGGCAAAGGC
   CTCGAGTGGATGGGCTACATCAACTACAGCGGCAACACCAACTACAACC CCAGCCTGAAGTCCAGAATC
   ACCATCAGCAGAGACACCAGCAAGAACCAGTTCTCCCTGAAGCTGAGCAGCGTGACAGCCGCCGATACA
   GCCGTGTACTACTGTGCCACAAGCTACTACGGCAACAGCTTCATCTACTGGGGCCAGGGCACACTGGTC
   ACCGTTTCTTCT 18D10VHv3 : SEQ ID NOs: 216-220
   <-----------FR1---------> CDR1      <-----FR2---->      CDR2
   QVQLQESGPGLVKPSETLSLTCTVSGGSISSNYAWNWIRQPPGKGLEWIGYINYSGNTNYNPSLKS
   <-------------FR3--------------> CDR3    <---FR4--->
   RVTISRDTSKNQFSLKLSSVTAADTAVYYCATSYYGNSFIYWGQGTLVTVSS
      Nucleic acid sequence
   CAGGTTCAGCTGCAAGAGTCTGGACCTGGCCTGGTCAAGCCTAGCGAGACACTGAGCCTGACCTGT
   ACCGTGTCCGGCGGCAGCATCAGCAGCAACTACGCCTGGAACTGGATCAGACAGCCTCCTGGCAAAGGC
   CTCGAGTGGATCGGCTACATCAACTACAGCGGCAACACCAACTACAACCCTAGCCTGAAGTCCAGAGTG
   ACCATCAGCAGAGACACCAGCAAGAACCAGTTCTCCCTGAAGCTGAGCAGCGTGACAGCCGCCGATACA
   GCCGTGTACTACTGTGCCACAAGCTACTACGGCAACAGCTTCATCTACTGGGGCCAGGGCACACTGGTC
   ACCGTTTCTTCT 18D10VHv4 : SEQ ID NOs: 221-225
   <-----------FR1---------> CDR1      <-----FR2---->      CDR2
   QVQLQESGPGLVKPSETLSLTCTVSGGSISSNYAWNWIRQPPGKGLEWIGYINYSGYTNYNPSLKS
   <-------------FR3--------------> CDR3    <---FR4--->
   RVTISRDTSKNQFSLKLSSVTAADTAVYYCATSYYGNSFIYWGQGTLVTVSS
      Nucleic acid sequence
   CAGGTTCAGCTGCAAGAGTCTGGACCTGGCCTGGTCAAGCCTAGCGAGACACTGAGCCTGACCTGT
   ACCGTGTCCGGCGGCAGCATCAGCAGCAACTACGCCTGGAACTGGATCAGACAGCCTCCTGGCAAAGGC
   CTCGAGTGGATCGGCTACATCAACTACAGCGGCTACACCAACTACAACCCCAGCCTGAAGTCCAGAGTG
   ACCATCAGCAGAGACACCAGCAAGAACCAGTTCTCCCTGAAGCTGAGCAGCGTGACAGCCGCCGATACA
   GCCGTGTACTACTGTGCCACAAGCTACTACGGCAACAGCTTCATCTACTGGGGCCAGGGCACACTGGTC
   ACCGTTTCTTCT
```

-continued

```
    18D10VHv5 : SEQ ID NOs: 226-230
      <----------FR1---------> CDR1        <-----FR2----->      CDR2
    QVQLQESGPGLVKPSETLSLTCTVSGGSISSNYAWNWIRQPPGKGLEWIGYINYSGNTAYNPSLKS
    <-------------FR3-------------->    CDR3    <---FR4--->
    RVTISRDTSKNQFSLKLSSVTAADTAVYYCATSYYGNSFIYWGQGTLVTVSS
      Nucleic acid sequence
      CAGGTTCAGCTGCAAGAGTCTGGACCTGGCCTGGTCAAGCCTAGCGAGACACTGAGCCTGACCTGT
    ACCGTGTCCGGCGGCAGCATCAGCAGCAACTACGCCTGGAACTGGATCAGACAGCCTCCTGGCAAAGGC
    CTCGAGTGGATCGGCTACATCAACTACAGCGGCAACACCGCCTACAACCCCAGCCTGAAGTCCAGAGTG
    ACCATCAGCAGAGACACCAGCAAGAACCAGTTCTCCCTGAAGCTGAGCAGCGTGACAGCCGCCGATACA
    GCCGTGTACTACTGTGCCACAAGCTACTACGGCAACAGCTTCATCTACTGGGGCCAGGGCACACTGGTC
    ACCGTTTCTTCT 18D10VHv6 : SEQ ID NOs: 231-235
      <----------FR1---------> CDR1        <-----FR2----->      CDR2
    QVQLQESGPGLVKPSETLSLTCTVSGGSISSNYAWNWIRQPPGKGLEWIGYIYYSGNTNYNPSLKS
    <-------------FR3-------------->    CDR3    <---FR4--->
    RVTISRDTSKNQFSLKLSSVTAADTAVYYCATSYYGNSFIYWGQGTLVTVSS
      Nucleic acid sequence
      CAGGTTCAGCTGCAAGAGTCTGGACCTGGCCTGGTCAAGCCTAGCGAGACACTGAGCCTGACCTGT
    ACCGTGTCCGGCGGCAGCATCAGCAGCAACTACGCCTGGAACTGGATCAGACAGCCTCCTGGCAAAGGC
    CTCGAGTGGATCGGCTACATCTACTACAGCGGCAACACCAACTACAACCCCAGCCTGAAGTCCAGAGTG
    ACCATCAGCAGAGACACCAGCAAGAACCAGTTCTCCCTGAAGCTGAGCAGCGTGACAGCCGCCGATACA
    GCCGTGTACTACTGTGCCACAAGCTACTACGGCAACAGCTTCATCTACTGGGGCCAGGGCACACTGGTC
    ACCGTTTCTTCT 15F9VLv1 : SEQ ID NOs: 236-240
      <----------FR1-------->      CDR1          <-----FR2-----> CDR2  <---
    DIVMTQSPDSLAVSLGERATINCKSSQSLLNSGNQRNYLTWYQQKPGQPPKLLIYWASTRESGVPD
    -----------FR3------------->    CDR3   <--FR4--->
    RFSGSGSGTDFTLTISSLQAEDVAVYYCQNAYYYPLTFGGGTKVEIK
      Nucleic acid sequence
      GACATCGTGATGACACAGAGCCCTGATAGCCTGGCCGTGTCTCTGGGAGAGAGAGCCACCATCAAC
    TGCAAGAGCAGCCAGAGCCTGCTGAACAGCGGCAACCAGAGAAACTACCTGACCTGGTATCAGCAGAAG
    CCCGGCCAGCCTCCTAAGCTGCTGATCTACTGGGCCAGCACCAGAGAATCTGGCGTGCCCGATAGATTC
    AGCGGCAGCGGCTCTGGAACCGACTTCACCCTGACAATCAGCTCCCTGCAGGCCGAGGATGTGGCCGTG
    TACTACTGTCAGAACGCCTACTACTACCCTCTGACCTTCGGCGGAGGCACCAAGGTGGAAATCAAG 15F9VLv2 : SEQ ID NOs: 241-245
      <----------FR1-------->      CDR1          <-----FR2-----> CDR2  <---
    DIVMTQSPDSLAVSLGERATINCKSSQSLLNSGNQRNYLAWYQQKPGQPPKLLIYWASTRESGVPD
    -----------FR3------------->    CDR3   <--FR4--->
    RFSGSGSGTDFTLTISSLQAEDVAVYYCQQAYYYPLTFGGGTKVEIK
      Nucleic acid sequence
      GACATCGTGATGACACAGAGCCCTGATAGCCTGGCCGTGTCTCTGGGAGAGAGAGCCACCATCAAC
    TGCAAGAGCAGCCAGAGCCTGCTGAACAGCGGCAACCAGAGAAACTACCTGGCCTGGTATCAGCAGAAG
    CCCGGCCAGCCTCCTAAGCTGCTGATCTACTGGGCCAGCACCAGAGAATCTGGCGTGCCCGATAGATTC
    AGCGGCAGCGGCTCTGGAACCGACTTCACCCTGACAATCAGCTCCCTGCAGGCCGAGGATGTGGCCGTG
    TACTACTGTCAGCAGGCCTACTACTACCCTCTGACCTTCGGCGGAGGCACCAAGGTGGAAATCAAG 15F9VLv3 : SEQ ID NOs: 246-250
      <----------FR1-------->      CDR1          <-----FR2-----> CDR2  <---
    DIVMTQSPDSLAVSLGERATINCKSSQSLLYSGNQRNYLAWYQQKPGQPPKLLIYWASTRESGVPD
    -----------FR3------------->    CDR3   <--FR4--->
    RFSGSGSGTDFTLTISSLQAEDVAVYYCQQAYYYPLTFGGGTKVEIK
      Nucleic acid sequence
      GACATCGTGATGACACAGAGCCCTGATAGCCTGGCCGTGTCTCTGGGAGAGAGAGCCACCATCAAC
    TGCAAGAGCAGCCAGAGCCTGCTGTACAGCGGCAACCAGAGAAACTACCTGGCCTGGTATCAGCAGAAG
    CCCGGCCAGCCTCCTAAGCTGCTGATCTACTGGGCCAGCACCAGAGAATCTGGCGTGCCCGATAGATTC
    AGCGGCAGCGGCTCTGGAACCGACTTCACCCTGACAATCAGCTCCCTGCAGGCCGAGGATGTGGCCGTG
    TACTACTGTCAGCAGGCCTACTACTACCCTCTGACCTTCGGCGGAGGCACCAAGGTGGAAATCAAG 18A9VLv1 : SEQ ID NOs: 251-255
      <----------FR1-------->      CDR1          <-----FR2-----> CDR2  <---
    DIVMTQSPDSLAVSLGERATINCKSSQSLLNSGNQKNYLTWYQQKPGQPPKLLIYWASTRESGVPD
    -----------FR3------------->    CDR3   <--FR4--->
    RFSGSGSGKDFTLTISSLQAEDVAVYYCQNNYFYPLTFGGGTKVEIK
      Nucleic acid sequence
      GACATCGTGATGACACAGAGCCCTGATAGCCTGGCCGTGTCTCTGGGAGAGAGAGCCACCATCAAC
    TGCAAGAGCAGCCAGAGCCTGCTGAACAGCGGCAACCAGAAGAACTACCTGACCTGGTATCAGCAGAAG
    CCCGGCCAGCCTCCTAAGCTGCTGATCTACTGGGCCAGCACCAGAGAAAGCGGCGTGCCCAGATAGATTC
    AGCGGCAGCGGCTCTGGAAAGGACTTCACCCTGACAATCAGCTCCCTGCAGGCCGAGGATGTGGCCGTG
    TACTACTGCCAGAACAACTACTTCTACCCTCTGACCTTCGGCGGAGGCACCAAGGTGGAAATCAAG 18A9VLv2 : SEQ ID NOs: 256-260
      <----------FR1-------->      CDR1          <-----FR2-----> CDR2  <---
    DIVMTQSPDSLAVSLGERATINCKSSQSLLNSGNQKNYLAWYQQKPGQPPKLLIYWASTRESGVPD
    -----------FR3------------->    CDR3   <--FR4--->
    RFSGSGSGTDFTLTISSLQAEDVAVYYCQQNYFYPLTFGGGTKVEIK
    GACATCGTGATGACACAGAGCCCTGATAGCCTGGCCGTGTCTCTGGGAGAGAGAGCCACCATCAAC
```

```
-continued
TGCAAGAGCAGCCAGAGCCTGCTGAACAGCGGCAACCAGAAGAACTACCTGGCCTGGTATCAGCAGAAG
CCCGGCCAGCCTCCTAAGCTGCTGATCTACTGGGCCAGCACCAGAGAAAGCGGCGTGCCAGATAGATTC
AGCGGCAGCGGCTCTGGAACCGACTTCACCCTGACAATCAGCTCCCTGCAGGCCGAGGATGTGGCCGTG
TACTACTGCCAGCAGAACTACTTCTACCCTCTGACCTTCGGCGGAGGCACCAAGGTGGAAATCAAG 18D10VLv1 : SEQ ID NOs: 261-265
    <----------FR1-------->        CDR1         <-----FR2-----> CDR2   <---
    DIVMTQSPDSLAVSLGERATINCKSSQSLLNSGNQKNYLTWYQQKPGQPPKLLIYWASTRESGVPD
    -----------FR3------------->    CDR3   <--FR4--->
    RFSGSGSGTDFTLTISSLQAEDVAVYYCQNAYSFPWTFGQGTKVEIK
        Nucleic acid sequence
        GACATCGTGATGACACAGAGCCCTGATAGCCTGGCCGTGTCTCTGGGAGAGAGAGCCACCATCAAC
TGCAAGAGCAGCCAGAGCCTGCTGAACAGCGGCAACCAGAAGAACTACCTGACCTGGTATCAGCAGAAG
CCCGGCCAGCCTCCTAAGCTGCTGATCTACTGGGCCAGCACCAGAGAAAGCGGCGTGCCAGATAGATTC
AGCGGCAGCGGCTCTGGAACCGACTTCACCCTGACAATCAGCTCCCTGCAGGCCGAGGATGTGGCCGTG
TACTACTGTCAGAACGCCTACAGCTTCCCCTGGACATTCGGCCAGGGCACCAAGGTGGAAATCAAG 18D10VLv2 : SEQ ID NOs: 266-270
    <----------FR1-------->        CDR1          <-----FR2-----> CDR2   <---
    DIVMTQSPDSLAVSLGERATINCKSSQSLLNSGNQKNYLAWYQQKPGQPPKLLIYWASTRESGVPD
    -----------FR3------------->    CDR3   <--FR4--->
    RFSGSGSGTDFTLTISSLQAEDVAVYYCQQAYSFPWTFGQGTKVEIK
        Nucleic acid sequence
        GACATCGTGATGACACAGAGCCCTGATAGCCTGGCCGTGTCTCTGGGAGAGAGAGCCACCATCAAC
TGCAAGAGCAGCCAGAGCCTGCTGAACAGCGGCAACCAGAAGAACTACCTGGCCTGGTATCAGCAGAAG
CCCGGCCAGCCTCCTAAGCTGCTGATCTACTGGGCCAGCACCAGAGAAAGCGGCGTGCCAGATAGATTC
AGCGGCAGCGGCTCTGGAACCGACTTCACCCTGACAATCAGCTCCCTGCAGGCCGAGGATGTGGCCGTG
TACTACTGTCAGCAGGCCTACAGCTTCCCCTGGACATTCGGCCAGGGCACCAAGGTGGAAATCAAG
```

Example 5. Detection of Biological Activity of the Humanized Antibody Against Claudin 18.2

1) Affinity Determination of Humanized Antibody (EC50)

The cells at logarithmic growth phase were taken, blocked with 3% BSA for 30 minutes, plated at $5\times10^4$ cells/100 µL into a U-shaped 96-well plate, centrifuged at 1100 rpm for 3 minutes, the supernatant was discarded, the cells were gently patted and loosed, 50 µL of antibody diluted according to the series was added to each well (antibody concentration starts from 100 nM, 5 times dilution in 8 series), incubated at 4° C. for 1 hour. After the incubation, 140 µL of 0.5% BSA was added to each well to wash 3 times, AF 647 APC anti-human secondary antibody was added with 30 µL/well and incubated at 4° C. for 40 minutes. After the incubation, 140 µL of 0.5% BSA was added to each well to wash 3 times, and finally resuspended each well with 50 µL PBS for iQue (Intellicyt, USA) detection (shown in Table 2).

TABLE 2

| Antibody combination | VL | VH | EC50(nM) |
|---|---|---|---|
| 15F9 Chimera | 15F9 mVL | 15F9 mVH | 3.322 |
| h15F9.v15 | 15F9VLv1 | 15F9VHv5 | 1.672 |
| h15F9.v15r1 | 15F9VLv1 | 15F9VHv5r1 | 2.529 |
| h15F9.v15r2 | 15F9VLv1 | 15F9VHv5r2 | 1.649 |
| h15F9.v16 | 15F9VLv1 | 15F9VHv6 | 0.705 |
| h15F9.v25 | 15F9VLv2 | 15F9VHv5 | 0.773 |
| h15F9.v25r1 | 15F9VLv2 | 15F9VHv5r1 | 1.720 |
| h15F9.v25r2 | 15F9VLv2 | 15F9VHv5r2 | 1.614 |
| h15F9.v26 | 15F9VLv2 | 15F9VHv6 | 1.024 |
| h15F9.v35 | 15F9VLv3 | 15F9VHv5 | 0.951 |
| h15F9.v35r1 | 15F9VLv3 | 15F9VHv5r1 | 1.200 |
| h15F9.v35r2 | 15F9VLv3 | 15F9VHv5r2 | 0.879 |
| h15F9.v36 | 15F9VLv3 | 15F9VHv6 | 0.786 |
| 18A9 Chimera | 18A9 mVL | 18A9 mVH | 1.034 |
| h18A9.v11 | 18A9VLv1 | 18A9VHv1 | 0.645 |
| h18A9.v12 | 18A9VLv1 | 18A9VHv2 | 0.913 |
| h18A9.v13 | 18A9VLv1 | 18A9VHv3 | 0.761 |
| h18A9.v14 | 18A9VLv1 | 18A9VHv4 | 0.548 |
| h18A9.v15 | 18A9VLv1 | 18A9VHv5 | 1.407 |
| h18A9.v16 | 18A9VLv1 | 18A9VHv6 | 0.799 |
| h18A9.v17 | 18A9VLv1 | 18A9VHv7 | 1.425 |
| h18A9.v21 | 18A9VLv2 | 18A9VHv1 | 1.027 |

TABLE 2-continued

| Antibody combination | VL | VH | EC50(nM) |
|---|---|---|---|
| h18A9.v22 | 18A9VLv2 | 18A9VHv2 | 0.822 |
| h18A9.v23 | 18A9VLv2 | 18A9VHv3 | 1.170 |
| h18A9.v24 | 18A9VLv2 | 18A9VHv4 | 2.065 |
| h18A9.v25 | 18A9VLv2 | 18A9VHv5 | 0.964 |
| h18A9.v26 | 18A9VLv2 | 18A9VHv6 | 1.405 |
| h18A9.v27 | 18A9VLv2 | 18A9VHv7 | 0.646 |
| 18D10 Chimera | 18D10 mVL | 18D10 mVH | 2.068 |
| 18D10.V11 | 18D10VLv1 | 18D10VHv1 | 1.131 |
| 18D10.V12 | 18D10VLv1 | 18D10VHv2 | 1.678 |
| 18D10.V13 | 18D10VLv1 | 18D10VHv3 | 0.912 |
| 18D10.V14 | 18D10VLv1 | 18D10VHv4 | 1.744 |
| 18D10.V15 | 18D10VLv1 | 18D10VHv5 | 2.687 |
| 18D10.V16 | 18D10VLv1 | 18D10VHv6 | 2.313 |
| 18D10.V21 | 18D10VLv2 | 18D10VHv1 | 1.069 |
| 18D10.V22 | 18D10VLv2 | 18D10VHv2 | 1.897 |
| 18D10.V23 | 18D10VLv2 | 18D10VHv3 | 0.982 |
| 18D10.V24 | 18D10VLv2 | 18D10VHv4 | 1.926 |
| 18D10.V25 | 18D10VLv2 | 18D10VHv5 | 1.265 |
| 18D10.V26 | 18D10VLv2 | 18D10VHv6 | 1.874 |

2) ADCC Activity of Humanized Antibody Against Claudin 18.2 on Tumor Cells 30 mL of freshly drawn blood was taken, added to a 50 mL centrifuge tube, mixed with 15 mL 1×PBS, and 20 mL of Ficoll. Paque Plu was added to another 50 mL centrifuge tube, and then gently add the above-diluted 30 mL fresh blood to plate on the surface of Ficoll. Paque Plu, placed at 20° C. and centrifuged at 2000 rpm for 30 minutes. After centrifugation, the uppermost serum from the centrifuge tube was discarded with disposable pipettes and the second layer of white membrane layer (i.e., PBMC) from the four layers of liquid from top to bottom was pipetted into a 50 mL centrifuge tube, each tube contained 10 mL liquid. The separated PBMC was added to 1×PBS which in volume is 3 times larger than that of PBMC, mixed well, then centrifuged at 1300 rpm at 4° C. for 10 minutes, after the supernatant was discarded, 10 mL 1×PBS was added to resuspend and count.

The PBMC was placed in a 37° C. 5% $CO_2$ incubator for 2 hours, centrifuged at 1300 rpm for 10 minutes, the supernatant was removed, and resuspended in the pre-warmed 2.5% FBS/RPMI 1640 medium, the density of PBMC was adjusted to $8\times10^6$ cells/mL, 50 μL/well, that is, plated at $4\times10^5$ cells/well to U Type 96-well plate, then the diluted antibody was added (from 40 μg/mL, 2 times dilution in 6 series) at 25 μL/well, incubated in a 37° C. 5% $CO_2$ incubator for 30 minutes. After incubation for 30 minutes, 25 μL of diluted Kato III cells was added, that is, $8\times10^3$ cells/well, and placed in a 37° C. 5% $CO_2$ incubator for 4 hours. Thirty minutes before the detection, 2 μL of lysate (10×) was added to the well of the maximum target cell number and put back to continue culture. After 4 hours, the PBMC was centrifuged at 1000 rpm for 3 minutes, 50 μL of supernatant was taken to the black ELISA plate, 50 μL/well of LDH detection substrate was added, 25 μL/well of terminated solution was added after 10 minutes to stop the reaction, a microplate reader (Biotek) was used to perform reading.

The result is calculated as follows:

$$\text{Killing rate} = \frac{\text{Experiment well} - \text{Control well}}{\text{Maximum release well} - \text{Control well}} \times 100$$

The results are shown in FIG. 6. After the humanization, the antibodies 18D10, 18A9 and 15F9 all retained stronger ADCC activity.

3) CDC Cell Activity of Humanized Antibody Against Claudin 18.2 Against Tumor Cells Kato III cells at logarithmic growth phase were taken, washed with PBS and resuspended to a density of $1\times10^7$ cells/mL, a certain amount of CFSE (Sigma, 87444-5MG-F) was added and made its final concentration 1 μM. After incubating the cells at room temperature for 10 minutes, 3 times the volume of medium was supplemented to terminate, centrifuged at 1000 rpm at 4° C. for 5 minutes, medium was supplemented to adjust the cell density to $2\times10^6$ cells/ mL. The resuspended cells was plated into a 96-well plate with 50 μL/well and the diluted antibody was added respectively with 50 μL/well (antibody is diluted from 30 μg/mL 3 times in 5 gradients to 0.12 μg/mL), and finally the complement diluted to 30% with medium was added with 50 μL per well. After incubating for 2 hours in a 5% $CO_2$ incubator, the cells were taken out and centrifuged at 1000 rpm for 3 minutes, the supernatant was discarded, the PI diluted to 1:200 was mixed well with $5\times10^4$/well Sulfate latex (Invitrogen, S37227), and add to 96-well plate with 100 μL/well, incubated on ice for 10 minutes and then FACS detection was performed. The results are shown in FIG. 7. After humanization, the antibodies 18D10 and 15F9 both have stronger CDC effects.

4) Endocytosis of Humanized Antibody

10 μg/mL of polylysine solution was prepared with PBS, 0.5 mL of same was added to each well of 24-well plate, incubated at 37° C. for 15-30 minutes; seeded cells: $2\times10^4$ cells/well, 10 μg/mL of antibody solution was prepared with pre-warmed DMEM medium, the supernatant was pipetted from the well plate, 0.5 mL of the medium containing the corresponding antibody was added to each well, incubated in a 37° C. incubator for 30 minutes; the supernatant was gently discarded and 0.5 mL PBS was added, stood for 5 minutes, the above operation was repeated to wash three times; 10% formaldehyde was added to each well, stood for 20-40 minutes; the formaldehyde was gently discarded, 0.5 mL of 0.2% Triton-PBS was added, stood for 5 minutes, the above operation was repeated to wash three times; AF594-F(ab')2 goat-anti-hIgG(H+L) secondary antibody solution (1:300) was prepared with PBS, 100 μL of same was added to each well, incubated at room temperature for 45 minutes; the secondary antibody solution was gently discarded and 0.5 mL of 0.2% Triton-PBS was added, stood for 5 minutes, the above operation was repeated to wash three times; 8 μg/mL human Lamp-1/CD107a Mab wad prepared, 100 μL of same was add to each well, incubated at room temperature for 45 minutes; the antibody solution was gently discarded and 0.5 ml of 0.2% Triton-PBS was added, stood for 5 minutes, the above operation was repeated to wash three times; AF488-F(ab')2 goat anti-mIgG(H+L) solution (1:300) was prepared with PBS, 100 μL of same was add to each well, incubated at room temperature for 45 minutes; the supernatant solution was gently discarded, 0.5 mL of 0.1% Triton-PBS was added, stood for 5 minutes, the above operation was repeated to wash three times; 1 μg/mL of DAPI solution was prepared with PBS, stained at room temperature for 5 minutes, the supernatant solution was gently discarded, 0.5 mL of 0.1% Triton-PBS was added, stood for 5 minutes, the above operation was repeated to wash three times; sealed up with 90% glycerol, prepared to take pictures. The results were shown in FIG. 8. The humanized Claudin 18.2 antibody mainly binds to the cell membrane, and part of the antibody can enter the lysosome after endocytosis (as shown by the arrow).

The invention claimed is:

1. An antibody or antigen-binding portion thereof that binds to human Claudin 18.2, comprising:
- a heavy chain CDR1 of SEQ ID NO: 207 or 232,
- a heavy chain CDR2 of SEQ ID NO: 208, 223, 228 or 233,
- a heavy chain CDR3 of SEQ ID NO: 234;
- a light chain CDR1 of SEQ ID NO: 262 or 267,
- a light chain CDR2 of SEQ ID NO: 263, and
- a light chain CDR3 of SEQ ID NO: 264 or 269.

2. The antibody or antigen-binding portion thereof according to claim 1, comprising:
- a heavy chain variable region comprising the amino acid sequence of SEQ ID NO: 206, 211, 216, 221, 226, or 231, or a variant thereof having at least 80% identity to SEQ ID NO: 206, 211, 216, 221, 226, or 231; and
- a light chain variable region comprising the amino acid sequence of SEQ ID NO: 261 or 266, or a variant thereof having at least 80% identity to SEQ ID NO: 261 or 266.

3. The antibody or antigen-binding portion thereof according to claim 1, comprising:
- a heavy chain CDR1 of SEQ ID NO: 232;
- a heavy chain CDR2 of SEQ ID NO: 233;
- a heavy chain CDR3 of SEQ ID NO: 234;
- a light chain CDR1 of SEQ ID NO: 262;
- a light chain CDR2 of SEQ ID NO: 263; and
- a light chain CDR3 of SEQ ID NO: 264.

4. The antibody or antigen-binding portion thereof according to claim 1, wherein the antibody or antigen-binding portion thereof is humanized.

5. A pharmaceutical composition containing the antibody or antigen-binding portion thereof according to claim 1, or a conjugate comprising said antibody or antigen-binding portion thereof attached to a cytotoxic drug.

6. A method of treating gastric cancer in a mammal, comprising administering to the mammal in need thereof the antibody or antigen-binding portion thereof according to claim 1, or a conjugate comprising said antibody or antigen-binding portion thereof attached to a cytotoxic drug; optionally wherein the antibody kills cancer cells by ADCC or CDC effect.

7. The method according to claim 6, wherein the antibody or antigen-binding portion thereof comprises:
- a heavy chain variable region comprising the amino acid sequence of SEQ ID NO: 206, 211, 216, 221, 226 or 231, or a variant thereof having at least 80% identity to SEQ ID NO: 206, 211, 216, 221, 226, or 231; and
- a light chain variable region comprising the amino acid sequence of SEQ ID NO: 261 or 266, or a variant thereof having at least 80% identity to SEQ ID NO: 261 or 266.

8. The method according to claim 6, wherein the antibody or antigen-binding portion thereof comprises:

- a heavy chain CDR1 of SEQ ID NO: 232;
- a heavy chain CDR2 of SEQ ID NO: 233;
- a heavy chain CDR3 of SEQ ID NO: 234;
- a light chain CDR1 of SEQ ID NO: 262;
- a light chain CDR2 of SEQ ID NO: 263; and
- a light chain CDR3 of SEQ ID NO: 264.

9. The method according to claim 6, wherein the antibody or antigen-binding portion thereof is humanized.

10. The antibody or antigen-binding portion thereof according to claim 3, comprising:
- (i) a heavy chain variable region comprising the amino acid sequence of SEQ ID NO: 231, or an amino acid sequence having at least 80% identity thereto; and
- (ii) a light chain variable region comprising the amino acid sequence of SEQ ID NO: 261, or an amino acid sequence having at least 80% identity thereto.

11. The antibody or antigen-binding portion thereof according to claim 10, comprising a heavy chain variable region comprising the amino acid sequence of SEQ ID NO: 231, and a light chain variable region comprising the amino acid sequence of SEQ ID NO: 261.

12. The antibody or antigen-binding portion thereof according to claim 1, comprising:
- (i) heavy chain CDRs 1, 2 and 3 of SEQ ID NOs: 232, 233 and 234, respectively; and light chain CDRs 1, 2 and 3 of SEQ ID NOs: 267, 263 and 269, respectively;
- (ii) heavy chain CDRs 1, 2 and 3 of SEQ ID NOs: 207, 208 and 234, respectively; and light chain CDRs 1, 2 and 3 of SEQ ID NOs: 262, 263 and 264, respectively;
- (iii) heavy chain CDRs 1, 2 and 3 of SEQ ID NOs: 207, 208 and 234, respectively; and light chain CDRs 1, 2 and 3 of SEQ ID NOs: 267, 263 and 269, respectively;
- (iv) heavy chain CDRs 1, 2 and 3 of SEQ ID NOs: 232, 208 and 234, respectively; and light chain CDRs 1, 2 and 3 of SEQ ID NOs: 262, 263 and 264, respectively;
- (v) heavy chain CDRs 1, 2 and 3 of SEQ ID NOs: 232, 208 and 234, respectively; and light chain CDRs 1, 2 and 3 of SEQ ID NOs: 267, 263 and 269, respectively;
- (vi) heavy chain CDRs 1, 2 and 3 of SEQ ID NOs: 232, 223 and 234, respectively; and light chain CDRs 1, 2 and 3 of SEQ ID NOs: 262, 263 and 264, respectively;
- (vii) heavy chain CDRs 1, 2 and 3 of SEQ ID NOs: 232, 223 and 234, respectively; and light chain CDRs 1, 2 and 3 of SEQ ID NOs: 267, 263 and 269, respectively;
- (viii) heavy chain CDRs 1, 2 and 3 of SEQ ID NOs: 232, 228 and 234, respectively; and light chain CDRs 1, 2 and 3 of SEQ ID NOs: 262, 263 and 264, respectively; and
- (ix) heavy chain CDRs 1, 2 and 3 of SEQ ID NOs: 232, 228 and 234, respectively; and light chain CDRs 1, 2 and 3 of SEQ ID NOs: 267, 263 and 269, respectively.

13. The antibody or antigen-binding portion thereof according to claim 2, comprising:
- (i) a heavy chain variable region comprising the amino acid sequence of SEQ ID NO: 206, and a light chain variable region comprising the amino acid sequence of SEQ ID NO: 261;

(ii) a heavy chain variable region comprising the amino acid sequence of SEQ ID NO: 206, and a light chain variable region comprising the amino acid sequence of SEQ ID NO: 266;

(iii) a heavy chain variable region comprising the amino acid sequence of SEQ ID NO: 211, and a light chain variable region comprising the amino acid sequence of SEQ ID NO: 261;

(iv) a heavy chain variable region comprising the amino acid sequence of SEQ ID NO: 211, and a light chain variable region comprising the amino acid sequence of SEQ ID NO: 266;

(v) a heavy chain variable region comprising the amino acid sequence of SEQ ID NO: 216, and a light chain variable region comprising the amino acid sequence of SEQ ID NO: 261;

(vi) a heavy chain variable region comprising the amino acid sequence of SEQ ID NO: 216, and a light chain variable region comprising the amino acid sequence of SEQ ID NO: 266;

(vii) a heavy chain variable region comprising the amino acid sequence of SEQ ID NO: 221, and a light chain variable region comprising the amino acid sequence of SEQ ID NO: 261;

(viii) a heavy chain variable region comprising the amino acid sequence of SEQ ID NO: 221, and a light chain variable region comprising the amino acid sequence of SEQ ID NO: 266;

(ix) a heavy chain variable region comprising the amino acid sequence of SEQ ID NO: 226, and a light chain variable region comprising the amino acid sequence of SEQ ID NO: 261;

(x) a heavy chain variable region comprising the amino acid sequence of SEQ ID NO: 226, and a light chain variable region comprising the amino acid sequence of SEQ ID NO: 266; or (xi) a heavy chain variable region comprising the amino acid sequence of SEQ ID NO: 231, and a light chain variable region comprising the amino acid sequence of SEQ ID NO: 266.

14. A conjugate comprising the antibody or antigen-binding portion thereof of claim 1 attached to a cytotoxic drug.

15. The conjugate of claim 14, wherein the antibody or antigen-binding portion thereof comprises:

a heavy chain CDR1 of SEQ ID NO: 232;
a heavy chain CDR2 of SEQ ID NO: 233;
a heavy chain CDR3 of SEQ ID NO: 234;
a light chain CDR1 of SEQ ID NO: 262;
a light chain CDR2 of SEQ ID NO: 263; and
a light chain CDR3 of SEQ ID NO: 264.

16. The conjugate of claim 15, wherein the antibody or antigen-binding portion thereof comprises:

(i) a heavy chain variable region comprising the amino acid sequence of SEQ ID NO: 231, or an amino acid sequence having at least 80% identity thereto; and (ii) a light chain variable region comprising the amino acid sequence of SEQ ID NO: 261, or an amino acid sequence having at least 80% identity thereto.

17. The conjugate of claim 16, wherein the antibody or antigen-binding portion thereof comprises a heavy chain variable region comprising the amino acid sequence of SEQ ID NO: 231, and a light chain variable region comprising the amino acid sequence of SEQ ID NO: 261.

18. The method of claim 8, wherein the antibody or antigen-binding portion thereof comprises:

(i) a heavy chain variable region comprising the amino acid sequence of SEQ ID NO: 231, or an amino acid sequence having at least 80% identity thereto; and (ii) a light chain variable region comprising the amino acid sequence of SEQ ID NO: 261, or an amino acid sequence having at least 80% identity thereto.

19. The method of claim 18, wherein the antibody or antigen-binding portion thereof comprises a heavy chain variable region comprising the amino acid sequence of SEQ ID NO: 231, and a light chain variable region comprising the amino acid sequence of SEQ ID NO: 261.

20. The method of claim 6, wherein the mammal is a human.

* * * * *